United States Patent
Petersen et al.

(10) Patent No.: US 6,514,697 B1
(45) Date of Patent: Feb. 4, 2003

(54) METHODS FOR DETECTION OF CRYTOSPORIDIUM SPECIES AND ISOLATES AND FOR DIAGNOSIS OF CRYPTOSPORIDIUM INFECTIONS

(75) Inventors: Carolyn Petersen, San Diego, CA (US); Debra A. Barnes, Oakland, CA (US); Richard C. Nelson, Sausalito, CA (US); Jiri Gut, Novato, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/588,995

(22) Filed: Jun. 6, 2000

Related U.S. Application Data

(63) Continuation-in-part of application No. 08/827,171, filed on Mar. 27, 1997, now Pat. No. 6,254,869, and a continuation-in-part of application No. 08/928,361, filed on Sep. 12, 1997, now Pat. No. 6,071,518, which is a continuation-in-part of application No. 08/700,651, filed on Aug. 14, 1996, now Pat. No. 6,015,882, which is a continuation-in-part of application No. 08/415,751, filed on Apr. 3, 1995, now Pat. No. 5,643,772, which is a continuation of application No. 08/071,880, filed on Jun. 1, 1993, now abandoned, which is a continuation-in-part of application No. 07/891,301, filed on May 29, 1992, now abandoned.

(60) Provisional application No. 60/026,062, filed on Sep. 13, 1996, and provisional application No. 60/014,233, filed on Mar. 27, 1996.

(51) Int. Cl.⁷ .......................... C12Q 1/68; C07H 21/02; C07H 21/04; C12P 19/34; C07K 14/00
(52) U.S. Cl. ...................... 435/6; 435/91.2; 536/23.1; 536/24.3; 530/350
(58) Field of Search ............................ 435/6, 91.2, 7.1; 536/23.1, 24.3; 935/76, 77, 78; 530/350

(56) References Cited

U.S. PATENT DOCUMENTS

| | | | |
|---|---|---|---|
| 5,346,811 A | * | 9/1994 | Galindo-Castro et al. |
| 5,556,774 A | * | 9/1996 | Wiedenmann et al. |
| 5,591,434 A | * | 1/1997 | Jenkins et al. |
| 5,789,190 A | * | 8/1998 | Crabb et al. |
| 6,071,518 A | * | 6/2000 | Petersen |

OTHER PUBLICATIONS

Laxer et al., Am. J,. of Tropical Medicine and Hygiene 45(6) : 688–694 (Dec. 1991).*

Petersen, C., The Mature erythrocyte surface antigen of *Plasmodium falciparum* is not required for knobs or cytoadherence, Molecular and Biochemical Parasitology, 36:61–66, (1989).

Petersen, C., The gene product of the *Plasmodium falciparum* 11.1 locus is a protein larger than one megadalton, Molecular and biochemical Parasitology, 42:189–196, (1990).

Petersen, C., Identification and Initial Characterization of Five *Cryptosporidium parvum* Sporozoite Antigen Genes, Infection and Immunity, pp. 2343–2348, (Jun. 1992).

Petersen, C., Characterization of a >900,000–$M_r$ *Cryptosporidium parvum* Sporozoite Glycoprotein Recognized by Protective Hyperimmune Bovine Colostral Immunoglobulin, Infection and Immunity, pp. 5132–5138, (Dec. 1992).

Coppel, Ross, L., Antibody Screening of Expression Libraries, Methods in Molecular Biology, vol. 21: Protocols in Molecuar Parasitology, Chapter 21, pp. 277–296, (1993).

* cited by examiner

Primary Examiner—Ethan C. Whisenant
(74) Attorney, Agent, or Firm—Hana Verny

(57) ABSTRACT

Cryptosporidium GP900, P68 and cryptopain antigens, antibodies, DNA or RNA for detection of Cryptosporidium in biological and environmental samples. A method for diagnosis of cryptosporidiosis. Kits and assays for the detection of Cryptosporidium comprising antigens, antibody, DNA or RNA components for immunological detection of Cryptosporidium protein with antibody, or detection of Cryptosporidium DNA by PCR amplification with GP900, P68 or cryptopain primers and probes for hybridization.

34 Claims, 14 Drawing Sheets

Figure 4A:
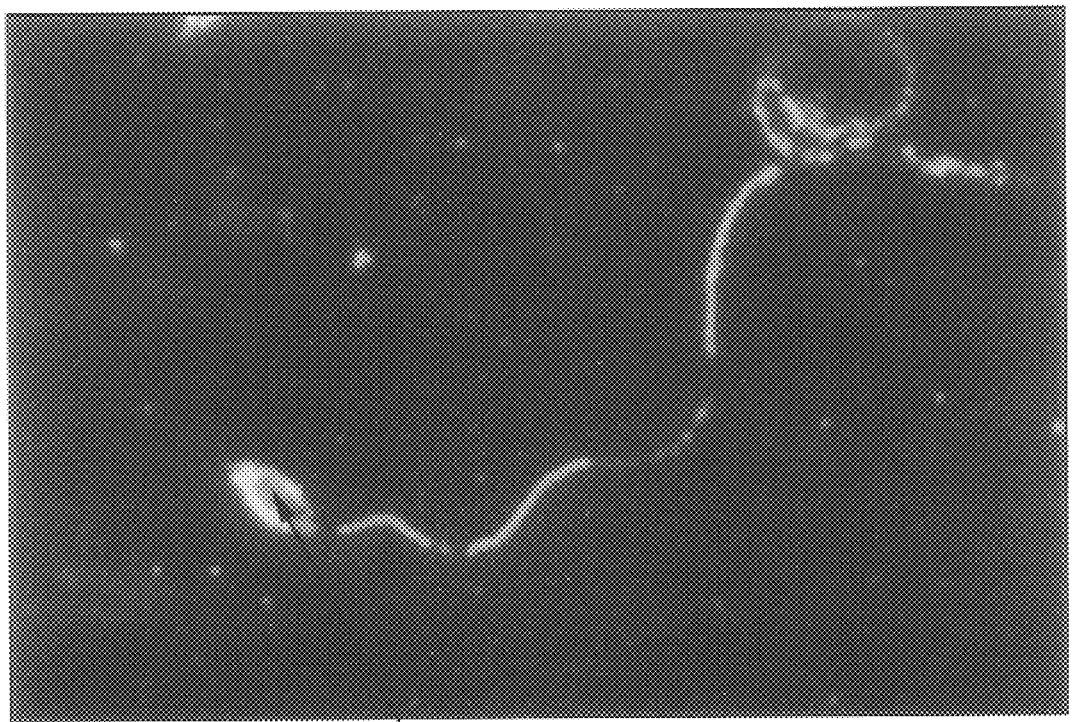

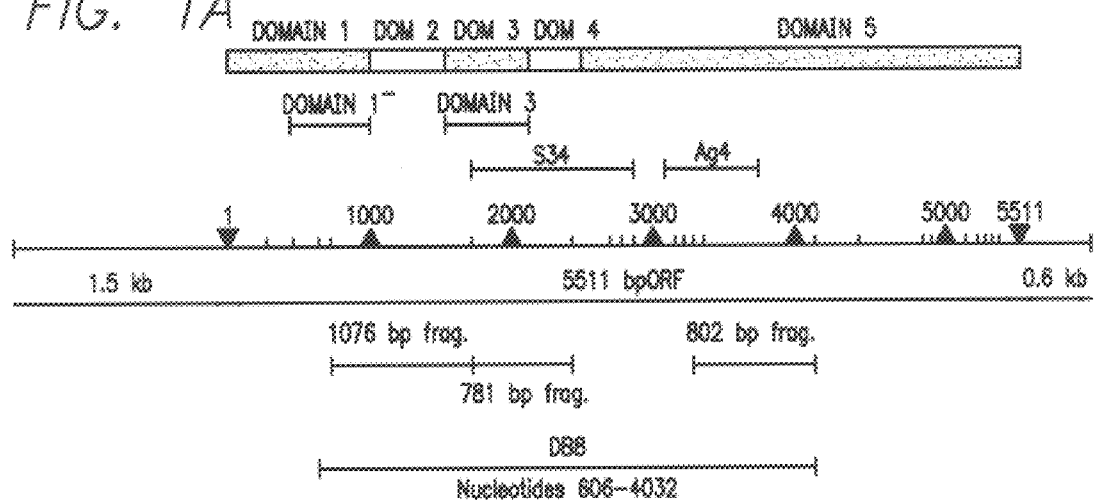
FIG. 1A
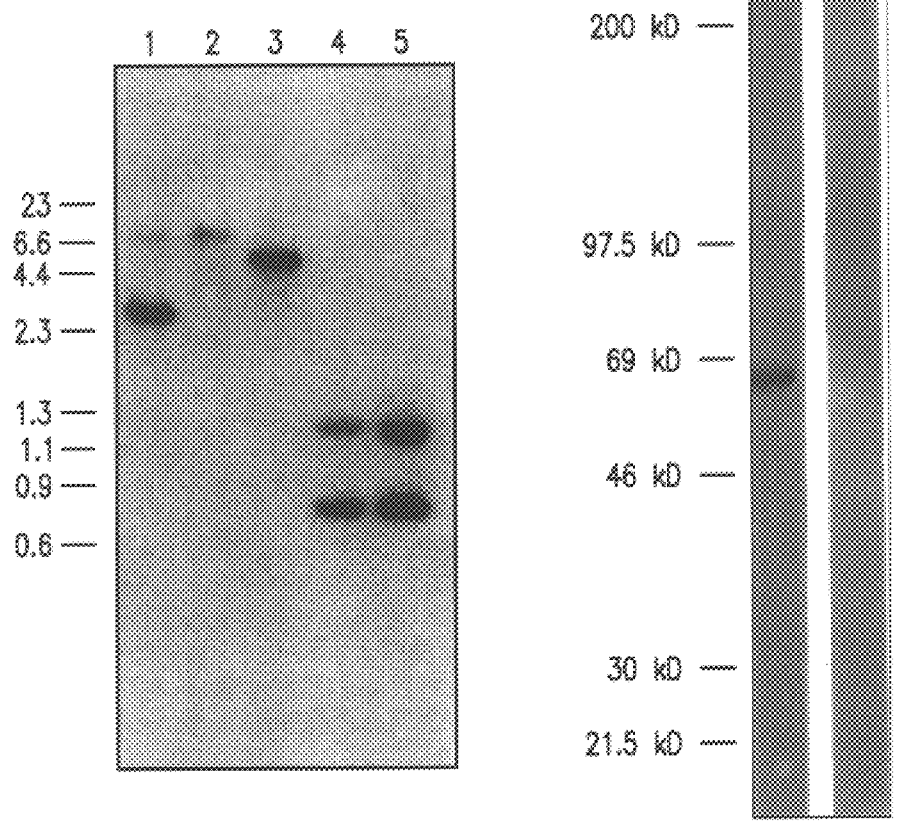
FIG. 1C
FIG. 5

FIG. 1B-1

Domain 1 (1-303), 303 aa

| | | | |
|---|---|---|---|
| MVNIKVSSSA | IALVAVIMNP | LFSLAFKSSN | RLEMRIESSG | 40
| AVSNEKFVIP | SLPSDLDPTT | FLLIDSTGKK | FSPYTGKHAD | 80
| ASTTSSAYSA | PFELDVSGVP | IEPNTRRMVD | PVSLMLFDNS | 120
| TGVMYDPNTN | SILEGSIAGI | RSES$\underline{C}$IVSEL | NFTSTTGFTT | 160
| DTSMNWPVSI | TSGELKDPNK | QATISGSRS$\underline{C}$ | GWKQGYSIDS | 200
| STGFRVDSIT | GLPTDPYPN$\underline{C}$ | PFNPVTGNLV | SRSTGKTIPN | 240
| TYAGVYRSNE | TKTTEPSANT | NFLLVDPKIN | AP$\underline{C}$NSENSFE | 280
| QVQIFDMGSK | VYIPYTK$\underline{C}$VG | VKH | | 303

Domain 2 (304-519), 216 aa

| | | | |
|---|---|---|---|
| TTTTTTTTTT | TTTTTTTTTT | TTTTTTTTTT | TTTTTTTTTT | 343
| TTTTTTTTTT | TTTTTTTTTT | TTTTTTTKKP | TTTTTTTTTT | 383
| TTTTTTTTTT | TTTTTTTTTT | TTTTTTTTTT | TTTKKPTTTT | 423
| TTTTTTTTTT | TTTTTTTTTT | TTTTTKKPTT | TTTTTTTTTT | 463
| TTTTTTTTTT | TTTTTTTTTT | TATTTTKKPT | TTTTTTTTTT | 503
| TKKPTTTTTA | TTTTTT | | | 519

Domain 3 (520-678), 159 aa

| | | | |
|---|---|---|---|
| SETESVIKPD | EW$\underline{C}$WLEKNGE | $\underline{C}$EAKGATYVG | VIGKDGRIEN | 559
| GMAFTMIPND | DTHVRFRFKV | KDVGNTISVR | $\underline{C}$GKGAGKLEF | 599
| PDRSLDFTIP | PVAGHNS$\underline{C}$SI | IVGVSGGGKI | HVSPYGSKDV | 639
| SLISAPIQP$\underline{C}$ | ELFNEVY$\underline{C}$DT | $\underline{C}$TAKYGAIHS | GYQTSADFV | 678

Domain 4 (679-790), 112 aa

| | | | |
|---|---|---|---|
| TTTTAKPTTT | TTGAPGQPTT | TTTGSPSKPT | TTTTTKATTT | 718
| TTILNPIITT | TTQKPTTTTT | TKVPGKPPIA | TTTTTLKPIV | 758
| TTTTTKATTT | TTTTVPTTTT | TTKRDEMTTT | TT | 790

Domain 5 (791-1832), 1042 aa

| | | | |
|---|---|---|---|
| PLPDIGDIEI | TPIPIEKMLD | KYTRMIYDYN | SGLLLDSNDE | 830
| PIPGSQAGQI | ADTSNLFPVQ | THKST$\underline{GLPID}$ | $\underline{PMVGLPFDPK}$ | 870
| SGNLVHPYTN | QTMSGLSVSY | LAAKNLTVDT | DETY$\underline{GLPIDT}$ | 910
| $\underline{LTGYPLDPVS}$ | LIPFNPETGE | LFDPISDEIM | NGTIAGIVSG | 950
| ISASESLLSQ | KSAPIDPATN | MVVGEFGGLL | NPATGVMIPG | 990
| SLGPSEQTPF | SPEIEDGGII | PPEVAAANAD | KFKLSIPPSV | 1030
| PESIPEKDQK | IDSISELMYD | IESGRLIGQV | SKRPIPGSIA | 1070
| GDLNPIMKTP | TQTDSVTGKP | IDPTT$\underline{GLPFN}$ | $\underline{PPTGHLINPT}$ | 1110
| NNNTMDSSFA | GAYKYAVSNG | IKTDNVY$\underline{GLP}$ | $\underline{VDEITGLPKD}$ | 1150
| PVSDIPFNST | TGELVDPSTG | KPINNYTAGI | VSGKR$\underline{GLPPI}$ | 1190
| $\underline{EDE}$NGNLFDP | STKLPIDGNN | QLVNPETNST | VSGSTSGSTK | 1230
| PKPGIPVNGG | GVVPDEEAKD | QADKGKDGLI | VPPTNSINKD | 1270
| PVTNTQYSNT | TGNIINPETG | KVIPGSLPGS | LNYPSFNTPQ | 1310
| QTDEITGKPV | DTVT$\underline{GLPYDP}$ | $\underline{ST}$GEIIDPAT | KLPIPGSVAG | 1350

FIG. 1B-2

```
DEILTEVLNI TTDEVTGLPI DLETGLPRDP VSGLPOLPNG  1390
TLVDPSNKKP IPGSHSGFIN GTSGEQSHEK DPSTGKPLDP  1430
NTGLPFDEDS GSLINPETGD KLQGSHSGTF MPVPGKPQGE  1470
GGGIMTPEQI LEALNKLPTS NEVNISPRPS SDAVPDRPTN  1510
TWWNKISGQT FQVDGKKTIP GSAASVIHTA LGTPTQTDPT  1550
TGLPSDPSTG LPFIPGFNVL VDPQTGEQIK GSVPYVSLYV  1590
KEKNIVTEAA YGLPVDPKTG FPIDPISYLP FAKNGELIDP  1630
ISGKYFSGSI AGFISGKAGS QSKSSDESGN PIDPSTNMPY  1670
DPKTGKLIDP ESGIAIDNSV SGVFATVPGT AAPKKGGVIP  1710
ESVAAEAAKK YFAANVEGEG EGEEVPPPPE SSSNIAIOAA  1750
GGASAAVGLV AAVGAWYASR NRQEGEDDDD YQMDLKQNMK  1790
KKRKKRVMKQ QMKLLLQLSV IHHSGTNLKR RKDFSNSKKF  1830
RI                                          1832
```

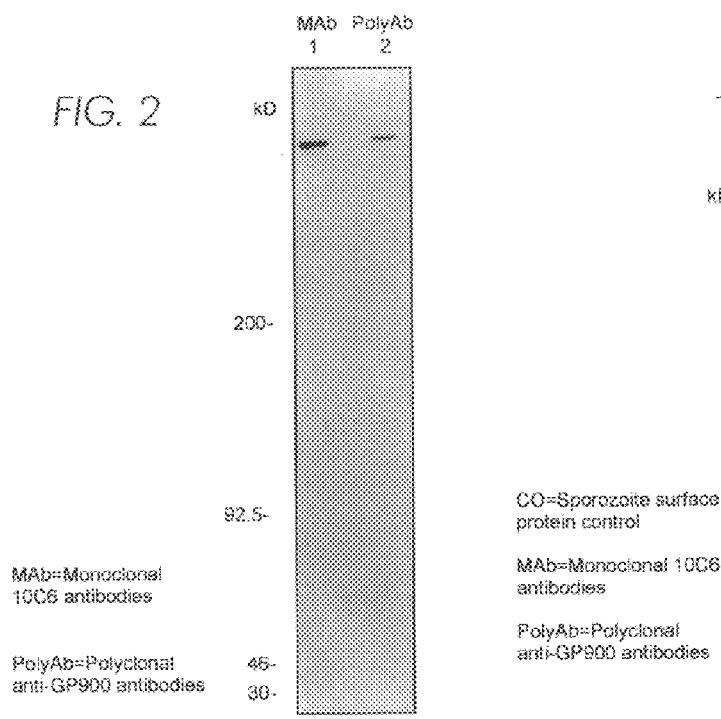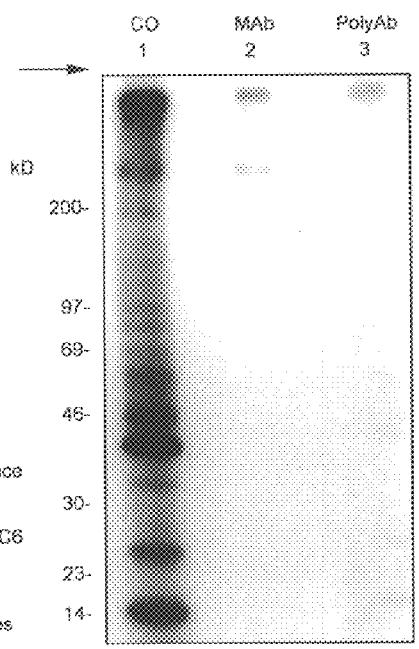

SHED
BP900          BP900

FIG. 6-1

```
                                                                        Alu I
                                                                        Sac I
                                                                        HgiA I
                                                                        Ecl136 I
                                                                        Bsp1286 I
              Bsr I                       Rsa I  Mse I                  Ban II
              Mse I                       Csp6 I                 Mnl I
              |   |                       |     |                |  ||
    AGTAAGGGTCAATTATTTAACCCAGTAAGTAAGTTGTGTGTACGACTTAAAGACAATGTTGTAGGTGGAGGAGCTCTGGT  80
    TCATTCCCAGTTAATAAATTGGGTCATTCATTCAACACACATGCTGAATTTCTGTTACAACATCCACCTCCTCGAGACCA
          *    |  *|     *               |     |  *           *          | *||       *
              17 22                      40    40 47                     68 71
                                               40                           71
                                                                            71
                                                                            71
                                                                            71
                                                                            71
                                                                            72

Mse I
                                            Ase I                                Mnl I
                      Bfa I                 Taq I                 Alu I      Bfa I
              Fok I   Alu I                 BstB I         Tth111 II Dde I   Alu I
              |       | |                   || ||            |    *  | |     | | |
    TTTGGATGATTGTCGTAAAGCTAGTGATGGAAGTGGATTATTCGAATTAATGCCAAACAATCAGCTCAGATTAGCTAGAG  160
    AAACCTACTAACAGCATTTCGATCACTACCTTCACCTAATAAGCTTAATTACGGTTTGTTAGTCGAGTCTAATCGATCTC
       |    *    |*|         *    *||   ||  *    |    *    ||    *   ||   | *
       84        99                121          134          145        153
                 101                122                      143        155
                                    126                                  158
                                    127

Ple I
                                          Hinf I
                        ScrF I            ScrF I
                        EcoR II           EcoR II
                        Dsa V             Dsa V   Nru I              Fnu4H I
                        BstN I            BstN I  BspW I       Dde I Bsr I
              Mse I     BstK I            BstK I  BstU I       Mse I Bbv I    BstX I
              |         |                 |    |  |||          |   |  |       |
    GTGGAAATCTATGCTTAACAAGTCCAGGAGATAAGCCAGGAGTCGCGAATGTTGCATTAAACTCAGCAGCCAGTTCCACA  240
    CACCTTTAGATACGAATTGTTCAGGTCCTCTATTCGGTCCTCAGCGCTTACAACGTAATTTGAGTCGTCGGTCAAGGTGT
        *   |   *   |       *         |   |  |||   *    |  *   |     |        | *
           175      184                196    204           217       226      236
                    184                196    205                     222 230
                    184                196    203                         226
                    184                196
                                       200
                                       200
                                                                               Mbo II
                    Sau96 I                                              Tfi I
                    Ava II                                               Hinf I
                    |                                                    | |
    AGTGTGGTTAGAACAGGTATTGAGAATGGTCCAGCAATGGCTGTTGATGGAAAGGATACATCATATTGGTTGTCAGATTC  320
    TCACACCAATCTTGTCCATAACTCTTACCAGGTCGTTACCGACAACTACCTTTCCTATGTAGTATAACCAACAGTCTAAG
         *           *       |*        *      *      *          *       | |*
```

FIG. 6-2

```
                      268                                                           326
                      268                                                           316
                                                                                    319
    ScrF I                                         Msp I
    EcoR II                                        Hpa II
    Dsa V                         Mse I            BsrF I
    BstN I      Tfi I             Hpa I            BsaW I                      EcoR V
    BstK I      Hinf I            Hinc II          Age I      Mae III   Mse I
       |          |                ||               ||          |         |    |
TTCAACTCCTGGTAAAGATTCTGCAAATGTTAACTTTTTGAGTGATACCGGTTCAGTTACAAAACTTAAAGATATCTTTA    400
AAGTTGAGGACCATTTCTAAGACGTTTACAATTGAAAAACTCACTATGGCCAAGTCAATGTTTTGAATTTCTATAGAAAT
   | *        | *       ||       *      || *       | *        | *|          *
   328        337       349             367        376        386
   328        337       349             367                   391
   328                  350             367
   328                                  368
   328                                  368
                           Ssp I
                           Mse I         Mse I
                            | |           |
TTGAGTGGAAATATCCTGCCATTGACTTTTAATATTGATTTAAGTGAAAATGGAAAGGAATATCAAACCCAAGTTTCTGTG    480
AACTCACCTTTATAGGACGGTAACTGAAATTATAACTAAATTCACTTTTACCTTTCCTTATAGTTTGGGTTCAAAGACAC
       *         *         ||       |*        *         *         *         *
                          428       439
                           430
                Hinc II
                Mse I
                Ase I                                                Apo I
                ||      |                                              |
AATAATAATGGATTAATGTCAACCACTTATTCATTAGAAGGAAAGAAAGCAAGATATGTCAAAATTCAAATGACAATTCC    560
TTATTATTACCTAATTACAGTTGGTGAATAAGTAATCTTCCTTTCTTTCGTTCTATACAGTTTTAAGTTTACTGTTAAGG
    * ||       | *        *         *         *         *         *|        *         *
       492
       493
           498
                                                                           Rsa I
                                                           Hph I           Csp6 I
    BsmA I                                 Tth111 II       Ssp I           Sca I   Mnl I
       |                                       |            |               ||       |
AAGCCAAGATGAGACAGGGAAATATGTGTATGGTATCAAACAGGTGAGAATATTCAGTAATACTATGAGAAGTACTGTTG    640
TTCGGTTCTACTCTGTCCCTTTATACACATACCATAGTTTGTCCACTCTTATAAGTCATTATGATACTCTTCATGACAAC
    *|        *         *         | *       | *        *         *|        |
     571                           597       609                   631      640
                                             603                            632
                                                                            632
                                              Ssp I           PflM I
                       Mse I                  BsmA I          Bsl I     Hph I
                         |                      | |             |         |
AGGATTGTAGTAGTGTTAAACAACATAATGATGGTAGAGACAAAATATTCCCACTCCCATATAATGGTGATAATTTTGCA    720
TCCTAACATCATCACAATTTGTTGTATTACTACCATCTCTGTTTTATAAGGGTGAGGGTATATTACCACTATTAAAACGT
        *          |    *         |  *       |*        *         | *        *
                  656                677              684        697
                                                                 697      706
```

FIG. 6-3

```
Msp I
 Hpa II
 ScrF I
 Nsi I
 Dsa V
 Bstk I
 Bcn I      Mse I                             Mse I         Alu I         Mae III
 ||          |                                 |             |             |
CCCGGATTATTGTTAAAGGCTCACGGAATTAGTGTAAAGAATAGATTAAATGAATTACAAGAGCTTTCTGGTAAGGTAAC  800
GGGCCTAATAACAATTTCCGAGTGCCTTAATCACATTTCTTATCTAATTTACTTAATGTTCTCGAAAGACCATTCCATTG
 ||    *    |    *         *              *    |  *        *  |    *    |   *
 721       733                                 766           782         796
 721
 721
 721
 721
  722
  722
                    Nla III
                    NspC I
                    Nsp7524 I
                    Nsp I
                    PpulO I
                    Nsi I
                    Fok I                   Mbo II         SfaN I
     Ssp I    Apo I SfaN I    Xmn I         Ear I    Mse I
       |       |   |||         |             |       |    |
TTCAATATTACCAAATTTGGATGCATGTAGAAAGACTTCTGATGGAAGAGATAACACATTAAAGATGCAGGCAACCAAAT  880
AAGTTATAATGGTTTAAACCTACGTACATCTTTCTGAAGACTACCTTCTCTATTGTGTAATTTCTACGTCCGTTGGTTTA
       |    *  |   ||  |        *        |    *     |*    |      *        *
      804     813 820  830              845         859
                   819                  845              864
                   821
                   821
                    823
                    823
                    823
                     824
                                                  Taq I
                                                  Xho I
                             Mme I                PaeR7 I              Alu I
                      Mse I                       Ava I           Bsl I    Mnl I
                        |     |                    ||               ||      |
TAGGATTTTTGTCAGAAAAATTGGAGAAATTAACTTCCGACTATAATCTCGAGTATAAGTTTACGAAGCCAGCTTTAGGA  960
ACCCTAAAAACAGTCTTTTTAACCTCTTTAATTGAAGGCTGATATTAGAGCTCATATTCAAATGCTTCGGTCGAAATCCT
           *          *        |   *  |           ||  *          |*|      |*
                              910    916         928              949     959
                                                 928                 951
                                                 928
                                                  929
```

FIG. 6-4

```
                                                                    Mbo II
                        ScrF I
                        EcoR II
                        Dsa V
                        BstN I                              Dde I
                        BstK I                              Ple I
Nla IV                  BsaJ I           Mse I              Hinf I
  |                       |                |                  | |
GGTTCCGAGTTATATCCAGGGGAAGATTGTGTTGCTATTAAGAATGATAAGACTCAGGAAGCCATTAGTGGTTTTTATTA  1040
CCAAGGCTCAATATAGGTCCCCTTCTAACACAACGATAATTCTTACTATTCTGAGTCCTTCGGTAATCACCAAAAATAAT
  |    *    |    *    |    *         |*          *| |    *         *         *
 961      976                       998          1011
          976                                    1011
          976                                         1013
          976
          976
          976
                    982
                                                                 Bsr I
                                                                   |
TGTTAGACCATTCTGTTCAACCAAACCATTGAGAGTTTACTGTGATATGAACACTGGAAATACAATCTATCCAATGGAAA  1120
ACAATCTGGTAAGACAAGTTGGTTTGGTAACTCTCAAATGACACTATACTTGTGACCTTTATGTTAGATAGGTTACCTTT
       *         *         *         *         *  |    *         *         *
                                                 1093
                                    Nla III
                          Mbo II
                BspW I    NspC I
                Alu I     Nsp7524 i
                Fnu4H I   Nsp I                              Mse I
  Mbo II   Bbv I   Eco57 I         Mme I                    Mse I
    |       | | |   | |              |    |                   |
TGAGTGTTCATTCTTCCAGAGCAGCTTCTTCAGCATGTGCAACTGTTGGATTAAAACCATTATTGTTAAGGGACAAAAAG  1200
ACTCACAAGTAAGAAGGTCTCGTCGAAGAAGTCGTACACGTTGACAACCTAATTTTGGTAATAACAATTCCCTGTTTTTC
   *|      *| | *|   ||    *     |   *|       *    |  *         *
    1132    1141 1148              1165              1186
            1141      1153            1171
            1143      1153
            1144      1153
               1147
                   1154
                                         Mse I
 Tfi I        Mbo II             Ase I             Mbo II           Ple I
 Hinf I       Mse I              Ssp I             Ear I            Hinf I
   |            | |               | ||               |                |
GAATCTGTTGTAGGTATTAAGAAGATGTTGAATATGATGAATATTAATGATAATAGAAGAGTTATTCCTTTGACTCACGA  1280
CTTAGACAACATCCATAATTCTTCTACAACTTATACTACTTATAATTACTATTATCTTCTCAATAAGGAAACTGAGTGCT
   |    *    | *|    *         | ||   *       | *       *  |    *
 1201      1217                1240              1256             1272
 1201         1221                1243           1256             1272
                                     1244
```

FIG. 6-5

```
                                                                    SfaN I
            SfaN I                                       Apo I     Fnu4H I
            Fok I                                        Mbo II    Bbv I
             ||                                            | |      | |
CTTTGGTTGTGATAATCCTAAAGGATGCAATTCACAATTTACACAGTTAGGCAGTGGTGTTGAAGAATTTGTTGCTGCAT  1360
GAAACCAACACTATTAGGATTTCCTACGTTAAGTGTTAAATGTGTCAATCCGTCACCACAACTTCTTAAACAACGACGTA
     *      * ||    *        *          *          * | |  *    | | *
            1303                                      1342      1354
             1304                                      1345      1354
                                                                  1357

Fnu4H I
           Bbv I
  Dde I    Alu I            HgiA I
  Mnl I    Fnu4H I           Bsp1286 I     Bsr I        Rsa I
  Bsu36 I  Bbv I             Bpm I         Xmn I        Csp6 I
   ||       | |               | |           | |          |
ACCCTCAGGCAGCAGCTTCAAACTCTACATCTGGAGCACTTCCAGAACTGGTTCTTTGCAGTACAAATACCAATTTGAAG  1440
GAGGAGTCCGTCGTCGAAGTTTGAGATGTAGACCTCGTGAAGGTCTTGACCAAGAAACGTCATGTTTATGGTTAAACTTC
   ||  *   | |   *         * | |    *     | |  *       * |     *         *
  1363    1372              1391        1405          1421
  1363    1372               1394        1407          1421
   1364    1374              1394
           1369
           1369

Tfi I
  Nla III                         Hinf I
   |                               |
CATGAAAGCAATGCAATTTCCTTGTCTTGTGAAAGCAGATTCTCTGATATGAAGGTATTTCATTTGGAT  1509
GTACTTTCGTTACGTTAAAGGAACAGAACACTTTCGTCTAAGAGACTATACTTCCATAAAGTAAACCTA
 |     *        *         *     | *         *          *
1441                            1478
                                 1478
```

FIG. 7-1

```
1/1                             31/11
CAA AAC TTC CTA ATT TCT CAA TGT ATT ACT AAT TAA TAG AAA GTT TGT TTT ATT TTC ATG
gln asn phe leu ile ser gln cys ile thr asn OCH AMB lys val cys phe ile phe met
61/21                           91/31
TGG ATA AAT GAA TTA TTT TCT CTA TAC CGG CAT TTG CAT GCA ATT TTG TAT GAC TAA AAT
trp ile asn glu leu phe ser leu tyr arg his leu his ala ile leu tyr asp OCH asn
121/41                          151/51
GTA AAT AAT TAT TTG CAT GCA ATT ATG TGG GCA TGT CAT AGT TTT TCA AGA ATA ATA ATA
val asn asn tyr leu his ala ile met trp ala cys his ser phe ser arg ile ile ile
181/61                          211/71
AGA TGA CAT GAC AAG ATA TTC AAA AAA ATT TGA TGA TTA TAT GTT GAA GTT AAT TGA ACT
arg OPA his asp lys ile phe lys lys ile OPA OPA leu tyr val glu val asn OPA thr
241/81                          271/91
AAA AAG TAA TTA AGT AAA ATG GAC ATA GGA AAC AAC GTG GAA GAA CAT CAG GAA TAT ATT
lys lys OCH leu ser lys met asp ile gly asn asn val glu glu his gln glu tyr ile
301/101                         331/111
TCT GGA CCA TAC ATT GCA TTA ATT AAT GGC ACT AAT CAA CAA AGG GAA CCG AAT AAA AAG
ser gly pro tyr ile ala leu ile asn gly thr asn gln gln arg glu pro asn lys lys
361/121                         391/131
TTG AAA AAC ATA ATA ATT GCA ACG TTG ATT GCA ATC TTT ATA GTT TTG GTT GTT ACT GTA
leu lys asn ile ile ile ala thr leu ile ala ile phe ile val leu val val thr val
421/141                         451/151
TCT TTG TAT ATT ACT AAT AAC ACC AGT GAC AAA ATT GAC GAT TTC GTA CCT GGT GAT TAT
ser leu tyr ile thr asn asn thr ser asp lys ile asp asp phe val pro gly asp tyr
481/161                         511/171
GTT GAT CCA GCA ACT AGG GAG TAT AGA AAG AGT TTT GAG GAG TTC AAA AAG AAA TAC CAC
val asp pro ala thr arg glu tyr arg lys ser phe glu glu phe lys lys lys tyr his
541/181                         571/191
AAA GTA TAT AGC TCT ATG GAG GAG GAA AAT CAA AGA TTT GAA ATT TAT AAG CAA AAT ATG
lys val tyr ser ser met glu glu glu asn gln arg phe glu ile tyr lys gln asn met
601/201                         631/211
AAC TTT ATT AAA ACA ACA AAT AGC CAA GGA TTC AGT TAT GTG TTA GAA ATG AAT GAA TTT
asn phe ile lys thr thr asn ser gln gly phe ser tyr val leu glu met asn glu phe
661/221                         691/231
GGT GAT TTG TCG AAA GAA GAG TTT ATG GCA AGA TTC ACA GGA TAT ATA AAA GAT TCC AAA
gly asp leu ser lys glu glu phe met ala arg phe thr gly tyr ile lys asp ser lys
721/241                         751/251
GAT GAT GAA AGG GTA TTT AAG TCA AGT AGA GTC TCA GCA AGC GAA TCA GAA GAG GAA TTT
asp asp glu arg val phe lys ser ser arg val ser ala ser glu ser glu glu glu phe
781/261                         811/271
GTT CCC CCA AAT TCT ATT AAT TGG GTG GAA GCT GGA TGC GTG AAC CCA ATA AGA AAT CAA
val pro pro asn ser ile asn trp val glu ala gly cys val asn pro ile arg asn gln
841/281                         871/291
AAG AAT TGT GGG TCA TGT TGG GCT TTC TCT GCT GTT GCA GCT TTG GAG GGA GCA ACG TGT
lys asn cys gly ser cys trp ala phe ser ala val ala ala leu glu gly ala thr cys
901/301                         921/311
GCT CAA ACA AAC CGA GGA TTA CCA AGC TTG AGT GAA CAG CAA TTT GTT GAT TGC AGT AAA
ala gln thr asn arg gly leu pro ser leu ser glu gln gln phe val asp cys ser lys
```

FIG. 7-2

```
961/321                         991/331
CAA AAT GGC AAC TTT GGA TGT GAT GGA GGA ACA ATG GGA TTG GCT TTT CAG TAT GCA ATT
gln asn gly asn phe gly cys asp gly gly thr met gly leu ala phe gln tyr ala ile
1021/341                        1051/351
AAG AAC AAA TAT TTA TGT ACT AAT GAT GAT TAC CCT TAC TTT GCT GAG GAA AAA ACA TGT
lys ans lys tyr leu cys thr asn asp asp tyr pro tyr phe ala glu glu lys thr cys
1081/361                        1111/371
ATG GAT TCA TTT TGC GAG AAT TAT ATA GAG ATT CCT GTA AAA GCC TAC AAA TAT GTA TTT
met asp ser phe cys glu asn tyr ile glu ile pro val lys ala tyr lys tyr val phe
1141/381                        1171/391
CCG AGA AAT ATT AAT GCA TTA AAG ACT GCT TTG GCT AAG TAT GGA CCA ATT TCA GTT GCA
pro arg asn ile asn ala leu lys thr ala leu ala lys tyr gly pro ile ser val ala
1201/401                        1231/411
ATT CAG GCC GAT CAA ACC CCT TTC CAG TTT TAT AAA AGT GGA GTA TTC GAT GCT CCT TGT
ile gln ala asp gln thr pro phe gln phe tyr lys ser gly val phe asp ala pro cys
1261/421                        1291/431
GGA ACC AAG GTT AAT CAT GGA GTT GTT CTA GTT GAA TAT GAT ATG GAT GAA GAT ACT AAT
gly thr lys val asn his gly val val leu val glu tyr asp met asp glu asp thr asn
1321/441                        1351/451
AAA GAA TAT TGG CTA GTA AGA AAT AGC TGG GGT GAA GCG TGG GGA GAG AAA GGA TAC ATC
lys glu tyr trp leu val arg asn ser trp gly glu ala trp gly glu lys gly tyr ile
1381/461                        1411/471
AAA CTA GCT CTT CAT TCT GGA AAG AAG GGA ACA TGT GGT ATA TTG GTT GAG CCA GTG TAT
lys leu ala leu his ser gly lys lys gly thr cys gly ile leu val glu pro val tyr
1441/481                        1471/491
CCA GTG ATT AAT CAA TCA ATA TAA GCA TTT CAG TGT TTG ACT AAG TAA TTC TAA TAT ATT
pro val ile asn gln ser ile OCH ala phe gln cys leu thr lys OCH phe OCH tyr ile
1501/501                        1531/511
TCA GCA TTC TCA GAG ATA ATT TTA GTT CAA ATG AAC AAT CTA TTC ATA TAT ATA AGC ATT
ser ala phe ser glu ile ile leu val gln met asn asn leu phe ile tyr ile ser ile
1561/521                        1591/531
CCA TAC TTA ATT ATT TAT TGA TTT TAA TAA AAT GTT TGG CTA AAG AAA GCA ATC AAG ATA
pro tyr leu ile ile tyr OPA phe OCH OCH asn val trp leu lys lys ala ile lys ile
1621/541                        1651/551
ATT TAT GGA CGT TCT ATT GTT CTT ACT TCA ATA ATA ATC CTT
ile tyr gly arg ser ile val leu thr ser ile ile ile leu            SEQ ID NO: 1
```

FIG. 8

```
met asp ile gly asn asn val glu glu his gln glu tyr ile ser
 1           5                    10                    15
gly pro tyr ile ala leu ile asn gly thr asn gln gln arg glu
             20                   25                    30
pro asn lys lys leu lys asn ile ile ile ala thr leu ile ala
             35                   40                    45
ile phe ile val leu val val thr val ser leu tyr ile thr asn
             50                   55                    60
asn thr ser asp lys ile asp asp phe val pro gly asp tyr val
             65                   70                    75
asp pro ala thr arg glu tyr arg lys ser phe glu glu phe lys
             80                   85                    90
lys lys tyr his lys val tyr ser ser met glu glu glu asn gln
             95                   100                   105
arg phe glu ile tyr lys gln asn met asn phe ile lys thr thr
             110                  115                   120
asn ser gln gly phe ser tyr val leu glu met asn glu phe gly
             125                  130                   135
asp leu ser lys glu glu phe met ala arg phe thr gly tyr ile
             140                  145                   150
lys asp ser lys asp asp glu arg val phe lys ser ser arg val
             155                  160                   165
ser ala ser glu ser glu glu phe val pro pro asn ser ile
             170                  175                   180
asn trp val glu ala gly cys val asn pro ile arg asn gln lys
             185                  190                   195
asn cys gly ser cys trp ala phe ser ala val ala ala leu glu
             200                  205                   210
gly ala thr cys ala gln thr asn arg gly leu pro ser leu ser
             215                  220                   225
glu gln gln phe val asp cys ser lys gln asn gly asn phe gly
             230                  235                   240
cys asp gly gly thr met gly leu ala phe gln tyr ala ile lys
             245                  250                   255
asn lys tyr leu cys thr asn asp asp tyr pro tyr phe ala glu
             260                  265                   270
glu lys thr cys met asp ser phe cys glu asn tyr ile glu ile
             275                  280                   285
pro val lys ala tyr lys tyr val phe pro arg asn ile asn ala
             290                  295                   300
ley lys thr ala leu ala lys tyr gly pro ile ser val ala ile
             305                  310                   315
gln ala asp gln thr pro phe gln phe tyr lys ser gly val phe
             320                  325                   330
asp ala pro cys gly thr lys val asn his gly val val leu val
             335                  340                   345
glu tyr asp met asp glu asp thr asn lys glu tyr trp leu val
             350                  355                   360
arg asn ser trp gly glu ala trp gly glu lys gly tyr ile lys
             365                  370                   375
leu ala leu his ser gly lys lys gly thr cys gly ile leu val
             380                  385                   390
glu pro val tyr pro val ile asn gln ser ile
             395                  400 403      SEQ ID NO: 4
```

METHODS FOR DETECTION OF CRYTOSPORIDIUM SPECIES AND ISOLATES AND FOR DIAGNOSIS OF CRYPTOSPORIDIUM INFECTIONS

This application is a continuation-in-part of U.S. application Ser. No. 08/827,171, filed on Mar. 27, 1997, now U.S. Pat. No. 6,254,869, which claims benefit of Ser. No. 60/014,233 filed Mar. 27, 1996 and of U.S. application Ser. No. 08/928,361, filed on Sep. 12, 1997, now U.S. Pat. No. 6,071,518 which claims benefit of Ser. No. 60/026,062 filed Sep. 13, 1996 and is a continuation-in-part of U.S. application Ser. No. 08/700,651, filed on Aug. 14, 1996, now U.S. Pat. No. 6,015,882 which is a continuation-in-part of the U.S. application Ser. No. 08/415,751 filed on Apr. 3, 1995 now U.S Pat. No. 5,643,772, which is a continuation of Ser. No. 08/071,880 filed on Jun. 1, 1993, now abandoned which is a continuation-in-part of Ser. No. 07/891,301 filed May 29, 1992 now abandoned.

This invention was developed partially with U.S. Government support under National Institutes of Health Grant Nos. AI-29882 and AI 30295, UARP Government No.: R94-SF-0555 and the University of California Academic Senate grant. The U.S. and California Governments may have certain rights in this invention.

BACKGROUND OF THE INVENTION

1. Field of the Invention

This invention concerns methods for detection of Cryptosporidium species or individual Cryptosporidium isolates and for diagnosis of prior or concurrent Cryptosporidium infections. The method for detection of Cryptosporidium species involves detection of a Cryptosporidium surface antigens GP900, p68 or cryptopain, GP900, p68 or cryptopain antibodies, and GP900, p68 or cryptopain DNAs and RNAs using PCR primers from regions flanking different domains of GP900, p68 or cryptopain. The method for detection of Cryptosporidium isolates involves PCR amplification of portions of GP900, P68, cryptopain and flanking regions with or without restriction fragment length polymorphism analysis which yield a fingerprint for each individual isolate. The method for diagnosis of Cryptosporidium infections involves detecting a presence of GP900, p68 or cryptopain antibodies, GP900, p68 or cryptopain antigen or the DNA or RNA encoding the GP900, p68 or cryptopain antigen in biological and environmental samples. The methods of the invention detect the Cryptosporidium antigen comprised of a protein with or without carbohydrates attached thereto, or the DNA or RNA encoding the Cryptosporidium antigen or DNA adjacent to it (flanking regions), or a mutant, variant, analog or fragment thereof. The invention additionally concerns methods for production of recombinant Cryptosporidium antigens suitable for development of diagnostic and detection tools and kits.

BACKGROUND AND RELATED DISCLOSURES

Cryptosporidium is an Apicomlexan protozoa which causes gastrointestinal disease in humans and other vertebrates. In immunocompetent host, the disease process ends when protective antibody develops. In immunocompromised hosts, the disease may become chronic resulting in wasting, diarrhea, electrolyte abnormalities, dehydration and death. There is no effective treatment for cryptosporidiosis.

The genus Cryptosporidium consists of Apicomplexan parasites that invade and develop within epithelial cells of the gastrointestinal, hepatobiliary and respiratory tracts of a wide variety of vertebrates including reptiles, birds and mammals. Cryptosporidium was recognized as a cause of animal disease for several decades before the first cases of human cryptosporidiosis were reported in 1976. However, it was not until 1982 that the magnitude of disease caused by this parasite in both AIDS patients and immunocompetent hosts began to be appreciated. Subsequently, Cryptosporidium has been found to be one of the most common causes of human diarrhea worldwide, and to be an increasingly recognized cause of diarrhea in children, animal care workers, and travelers. (*Cryptosporidium and Cryptosporidiosis in Humans*, Ed. Fayer, R., CRC Press, Boca Raton (1997)).

Large water-borne outbreaks of cryptosporidiosis caused by contaminated municipal water supplies in the US or in the UK have been noted in the last decade (*N. Engl. J. Med.*, 320:1372 (1989), and 33:161 (1994)). A large outbreak in Milwaukee in April 1993 involved 400,000 persons and led to the subsequent deaths of more than hundred immunocompromised persons. Like a number of other waterborne outbreaks, the Milwaukee outbreak appears to have been due to contamination from farm or abattoir run-off and was specifically connected to cryptosporidiosis infected cows and calves. Nosocomial transmission in hospitals from patients to staff, patient to patient, and contaminated ice to patients and staff have also been well documented (*J. Infect. Dis.*, 158:647 (1985)).

Waterborne and nosocomial spread uncovered a number of biological characteristics of oocysts. First, the infectious dose of a parasite is very low. The ID50 for human volunteers with normal immune systems is 132 oocysts (*N. Engl. J. Med.*, 332:855 (1995)). Second, infected hosts, for example calves, excrete large numbers of oocysts, on the order of $10^{10}$/day. Third, the oocysts are fully sporulated and ready to infect when excreted. Fourth, the oocysts are environmentally hardy. They remain infectious in cool, moist areas for 3–4 months and are not killed by chlorine levels achievable in drinking water. Fifth, the oocysts are quite small, 4–6 $\mu$m, and are thus difficult to filter.

The infective forms of Cryptosporidium, called sporozoites and merozoites, appear to adhere to the host cell and release the contents of anterior organelles (rhoptries, micronemes or dense granules) during the invasion process (*Parasitol. Today*, 8:28(1992)). Proteins involved in these events have in many instances been found to be the target of invasion blocking immunity in vitro and neutralization in vivo (*Infect. Immun.*, 56:2538(1988)).

While the actual interaction between Cryptosporidium and the host's immune system is poorly understood, it is known that disruption of either the cellular or the humoral components can result in protracted cryptosporidiosis (*Parasitol. Today*, 8:24 (1992)). Specific antibodies alone appear to be enough to neutralize the organism's infectivity. In vitro and in vivo observations indicate that antibodies to *Cryptosporidium parvum* inhibit invasion and intracellular development leading to protection in challenge experiments, or amelioration of infection in established disease (*Infect. Immun.*, 59:1172 (1991)).

One source of such antibodies is hyperimmune bovine colostrum (HBC) collected from cows immunized with Cryptosporidium oocysts. Calves challenged with Cryptosporidium oocysts are protected from the development of disease by the administration of HBC (*Infect. Immun.*, 61:4079 (1993)). Some immunocompromised AIDS patients infected with Cryptosporidium have also responded to HBC with a reduction in or disappearance of the symptoms of the disease (*Gastroenterology*, 98:486 (1990)). Immunoglobulin from HBC (HBC Ig) has been found to inhibit the ability of the sporozoite to invade and/or develop intracellularly in vitro and it has been used to immunoprecipitate at least 22 different surface radioiodinated proteins of Cryptosporidium sporozoites. Western blot analysis of proteins of whole oocysts which contain sporozoite indicates that HBC predominantly recognizes two proteins of sizes 250 KD and >900 KD (*Infect. Immun.*, 61:4079 (1993)).

Although a connection between Cryptosporidium from water, dairy animals, pets, children in day care and hospital environments and cryptosporidiosis has been made, the relative importance of water, food, pets, sexual or casual person-to-person contact in the transmission of the parasite has not been established. The epidemiology of Cryptosporidium, particularly transmission and reservoirs of the parasite have been difficult to study because the organism cannot be propagated in vitro for the development of serological or growth characteristics as a method of systematic identification of Cryptosporidium species and individual isolates.

Therefore, availability of Cryptosporidium specific antigen, DNA and antibody markers for species identification and for differentiation of strains/isolates within species would be greatly advantageous.

While, as described above, the Cryptosporidium infection can have serious and, in some cases, fatal consequences, only limited detection and diagnostic methods, tools and kits are available.

Currently available Cryptosporidium detection methods are microbiological immunological assays and limited PCR-based detections. The microbiological detections of the organism in the stool has a very low sensitivity of detection of about 1000 organisms in one gram of stool. Sensitivity of antibody detection methods is somewhat improved but these methods still can detect the presence of the organism only when at least 500 organisms are present in one gram of stool. Attempts to use monoclonal antibodies for detection of cryptosporidiosis resulted in very expensive and not overly sensitive kits which, so far, have not generally replaced the classical microbiological detection techniques.

Thus, better and more sensitive methods for detection of Cryptosporidium are needed.

It is a primary objective of this invention to provide methods for detection of Cryptosporidium species or isolates by 1) specific detection of GP900, P68 or cryptopain antigens, 2) specific detection of GP900, P68 or cryptopain DNA fragments, and 3) detection of the presence of anti-Cryptosporidium antibodies indicating that the host has been, in the past, or is currently infected with Cryptosporidium.

All patents, patent applications and publications cited herein are hereby incorporated by reference.

SUMMARY OF THE INVENTION

One aspect of this invention concerns methods and kits for detection of Cryptosporidium species or individual Cryptosporidium isolates and for diagnosis of prior or concurrent Cryptosporidium infections.

Another aspect of this invention concerns a method for detection of Cryptosporidium species involving detection of a Cryptosporidium antigen GP900, p68 or cryptopain, GP900, p68 or cryptopain antibodies, and GP900, p68 or cryptopain DNAs and RNAs using PCR primers from regions flanking different domains of GP900, p68 or cryptopain.

Still another aspect of this invention concerns a method for detection of Cryptosporidium isolates involving PCR amplification of DNA fragments which are different in different isolates, such as poly-threonine rich domains or different restriction sites which yield a fingerprint for each individual isolate differentiating it from another isolate.

Yet another aspect of this invention concerns a method for diagnosis of Cryptosporidium infections involving detection of the presence of GP900, p68 or cryptopain antibodies, GP900, p68 or cryptopain antigen or the DNA or RNA encoding the GP900, p68 or cryptopain antigen protein with or without carbohydrates attached thereto, or a mutant, variant, analog or fragment thereof in biological and environmental samples.

Still yet another aspect of this invention concerns methods for production of recombinant Cryptosporidium antigens suitable for development of diagnostic and detection tools and kits.

Another aspect of this invention concerns antibodies, antigens, DNAs and RNAs used in methods or kits for detection of Cryptosporidium species and isolates or diagnosis of prior or concurrent Cryptosporidium infections.

Another aspect of this invention concerns polyclonal or monoclonal antibodies directed against the Cryptosporidium antigen for use in a method and kits for detection of cryptosporidiosis.

Another aspect of this invention concerns the GP900, p68 or cryptopain Cryptosporidium antigen or fragments thereof.

Still another aspect of this invention concerns a DNA and RNA encoding the Cryptosporidium antigen and fragments thereof suitable for preparation of anti-Cryptosporidium antibodies.

Still yet another aspect of the invention is the use of the GP900, p68 or cryptopain antigen, antibody, DNA or RNA for Cryptosporidium diagnosis of prior or current infection in a human or animal host or for detection of Cryptosporidium parasite in the environment.

Still another aspect of this invention concerns a DNA and RNA encoding the Cryptosporidium protein or glycoprotein comprising Cryptosporidium antigen or fragments thereof for use in production of the protein or glycoprotein for development of agents used for diagnosis or detection of Cryptosporidium infection.

Another aspect of this invention concerns the DNA sequence of 7334 bp (SEQ ID NO: 1) nucleotides encoding the GP900 protein of Iowa isolate and its upstream (5') protein coding and regulatory elements and its 3' noncoding sequence.

Another aspect of this invention concerns the DNA sequence of 5511 bp (SEQ ID NO: 2) nucleotides encoding GP900 of the Iowa isolate, and its nucleotide and size variants.

Another aspect of this invention concerns an amino acid sequence of 1837 amino acids (SEQ ID NO: 5) of GP900 of Iowa isolate, a >900 kD glycoprotein present in or on the surface of sporozoites and merozoites, and its amino acid and size variants.

Another aspect of this invention concerns the DNA sequence of 5318 bp (SEQ ID NO: 3) nucleotides encoding the GP900 protein of NINC isolate comprised of partial ORF and 3' flanking region.

Another aspect of this invention concerns the DNA sequence of 5163 bp (SEQ ID NO: 4) nucleotides encoding GP900 of the NINC isolate comprised of the partial ORF.

Another aspect of this invention concerns an amino acid sequence of 1721 amino acids (SEQ ID NO: 6) of GP900 of NINC isolate.

Another aspect of this invention concerns the DNA sequence of 2380 nucleotides (SEQ ID NO: 25) encoding a protein portion of P68, its nucleotide and size variants and its upstream (5') protein coding and regulatory elements.

Another aspect of this invention concerns an amino acid sequence comprising 503 amino acids (SEQ ID NO: 26) of a protein portion of P68, a 50–100 kDa glycoprotein of sporozoites and merozoites, and its amino acid and size variants.

Another aspect of this invention concerns the DNA sequence of 1663 bp (SEQ ID NO: 27) of cryptopain comprised of 5' and 3' flanking sequences, its pre pro fragments (SEQ ID NO: 28) and mature enzyme (SEQ ID NO: 29).

Another aspect of this invention concerns an amino acid sequence of 401 amino acids (SEQ ID NO: 30) of cryptopain, cryptopain pre and pro fragments (SEQ ID NO: 31), and mature enzyme (SEQ ID NO: 32).

Still another aspect of this invention are PCR primers which are oligonucleotides of about 14 to about 35 bp in length synthesized using portions of the GP900, P68 or cryptopain DNA and which are used by enzymatic reactions leading to the amplification of DNA.

Yet another aspect of this invention is a DNA probe which is an oligonucleotide or a larger segment of DNA used for direct hybridization with complementary DNA or RNA sequences.

Still yet another aspect of this invention concerns a method for diagnosing Cryptosporidium infection of a subject, comprising steps:

(a) contacting a body specimen, fluid or tissue obtained from the subject with an anti-Cryptosporidium monoclonal or polyclonal antibody; and (b) detecting the formation of antibody-antigen complex wherein the presence of the complex indicates positive diagnosis of the presence of a Cryptosporidium organism in the subject and wherein the absence of the complex indicates negative diagnosis of Cryptosporidium infection.

Still yet another aspect of this invention concerns a method for detecting a presence of Cryptosporidium parasite in a biological or environmental sample, said method comprising steps:

(a) contacting a biological or environmental sample with an anti-Cryptosporidium monoclonal or polyclonal antibody; and (b) detecting the formation of antibody-antigen complex wherein the presence of the complex indicates presence of the Cryptosporidium parasite in the sample and wherein the absence of the complex indicates absence of Cryptosporidium parasite in the sample.

Still yet another aspect of this invention concerns a method for detecting anti-Cryptosporidium antibody in a subject, said method comprising steps:

(a) contacting a body specimen, fluid or tissue obtained from the subject with the GP900, p68 or cryptopain antigen; and (b) detecting a formation of antibody-antigen complex wherein the presence of the complex indicates positive diagnosis of the presence of a Cryptosporidium antibody in the subject and wherein the absence of the complex indicates negative diagnosis of Cryptosporidium infection.

Still another aspect of this invention is a Cryptosporidium diagnostic or detection kit comprising anti-Cryptosporidium specific monoclonal and polyclonal antibodies, Cryptosporidium GP900, P68 or cryptopain antigen according to the invention and a means for detection of an antibody-antigen complex.

BRIEF DESCRIPTION OF THE DRAWINGS

FIG. 1 is the GP900 gene locus.

FIG. 2 is an immunoblot of Cryptosporidium parvum oocyst/sporozoite proteins showing detection of the >900 sporozoite protein with monoclonal and polyclonal antibodies to GP900.

FIG. 3 is the immunoprecipitation of $^{125}$I surface label Cryptosporidium parvum sporozoite proteins using monoclonal and polyclonal antibodies to GP900.

FIG. 4 is the MAb 7B3 indirect immunofluorescence detection of GP900 present on the surface and shed from the surface of a motile sporozoite.

FIG. 5 is an immunoblot of Cryptosporidium parvum oocyst/sporozoite proteins identified by polyclonal antibodies to P68.

FIG. 6 is a restriction map of P68 ORF DNA.

FIG. 7 is the DNA sequence of cryptopain (SEQ ID NO: 27) comprising sequences encoding segments for the pre and pro regions (SEQ ID NO: 28) and for mature enzyme (SEQ ID NO: 29).

FIG. 8 is the protein sequence (SEQ ID NO: 30) of cryptopain comprising segments for the pre and pro regions (SEQ ID NO: 31) and for mature enzyme (SEQ ID NO: 32).

FIG. 9 is a genomic Southern analysis of Cryptosporidium DNA using the cryptopain probe.

FIG. 10 is the genomic Southern analysis of the GP900 gene fragment of Iowa and AUCP isolate DNA hybridized with DB8 DNA probe from NINC isolate.

DEFINITIONS

As used herein:

"Cryptosporidium species" means any organism belonging to the genus Cryptosporidium, such as, for example, *Cryptosporidium parvum* or *Cryptosporidium muris*, but also includes other currently less well characterized organisms such as, for example, Cyclospora. Cryptosporidium species comprise Apicomlexan parasites which primarily invade cells of the gastrointestinal tract and cause disease in a susceptible host.

"Cryptosporidium isolate" means a viable Cryptosporidium separated from the other isolates having a specific genetic characterization (fingerprint) different from other isolates which may be identified by its specific genetic characterization and distinguished from other isolates having a different fingerprint. *Cryptosporidium parvum* was identified and isolated from oocysts of the Iowa, NINC and AUCP-1 isolates of *Cryptosporidium parvum* passaged through neonatal calves, as described in Example 1, and tested for their interaction with specific anti-GP900, p68 or cryptopain antibodies. Proteins which were shown to be targets of GP900, p68 or cryptopain antibodies were prepared according to Example 2, and visualized by enzyme-linked immunosorbent assay (ELISA), chemiluminescence or with $^{125}$I labeled Protein A followed by autoradiography as described in Example 7.

"Antigen" means a protein isolated from Cryptosporidium identified as GP900, P68 or cryptopain with or without glycoprotein attached thereto, detected in micronemes of developing merozoites and sporozoites. Antigen is present on the surface of the sporozoites and is shed from the sporozoite surface in vivo in host cells.

"GP900 antigen" means a protein with or without a carbohydrate attached thereto which defines the capacity of Cryptosporidium sporozoites and merozoites to infect host cells. When deglycosylated, the GP900 core protein has a variable molecular weight of approximately 150–250 kD. GP900 protein comprises 1837 amino acids, mutants, variants, or analogs thereof and identified as SEQ ID NO: 5 of Mr greater than 900 kilodaltons (kDa) which may contain a covalently attached glycoprotein, said GP900 detected at the surface of sporozoites or merozoites or free in conditioned media. GP900 is the target of antibodies which are present and detectable in the tissue or fluids of the Cryptosporidium infected subject.

"P68" means an apical protein of sporozoites or merozoites represented by 503 amino acids and identified as SEQ ID NO: 26 of Mr between approximately 50 and 100 kilodaltons which is a target of antibodies which inhibit infection, invasion or adhesion of Cryptosporidium.

"Cryptopain" or "Cryptopain antigen" means a protein which is a cathepsin L-like cysteine proteinase having a function in invasion and infection of host cells by Cryptosporidium. Cryptopain is represented by a protein containing 401 amino acids and is identified as SEQ ID NO: 30 (FIG. 3) comprising a protein of Mr 45 kDa. Homology to other cathepsin L-like cysteine proteinases indicates that the mature active enzyme is cleaved after amino acid 175 one residue N-terminal to a conserved prolines and comprises a 25 kDa protein of 226 amino acids (SEQ ID NO: 33). Cryptopain also includes size and sequence variant proteins which maintain the same function.

"Detection" means establishing a priority evidence for the presence or prior presence of living or dead Cryptosporidium by detecting Cryptosporidium antigens, cryptopain or Cryptosporidium DNA or RNA in the host, in a host biological sample obtained from a specimen such as stool, urine, blood, plasma, biopsy, saliva and such other samples as appropriate or in environmental samples including water, soil, food, etc.

"Diagnosis" means establishment of the presence or prior presence of Cryptosporidium infection or disease by using the GP900, P68 or cryptopain antigen, antibody to GP900, P68 or cryptopain, GP900, P68 or cryptopain DNA or RNA as a component of a diagnostic assay according to the invention.

"Host" or "subject" means humans, or animals including birds and cattle.

"GP900 DNA" means the sequence of 5511 nucleotides identified as SEQ ID NO: 2 which encodes an amino acid portion of the protein sequence of GP900 protein (SEQ ID NO: 5) and any variant, 5' extension, mutation and fragment thereof, which corresponds to genes encoding the antigen. Variants include but are not limited to the partial sequence of GP900-NINC or Iowa.

"GP900 RNA" means the RNA sequence corresponding to GP900 DNA sequence (SEQ ID NO: 2) which encodes the amino acid sequence of GP900 protein (SEQ ID NO: 5) and any 5' extension, variant, mutation and fragment thereof.

The "structure" or "structural characteristics" of GP900, P68 or cryptopain defines a protein, glycoprotein, DNA and RNA encoding the GP900, P68 or cryptopain protein and includes all structural variations, mutations and fragments exhibiting the same function.

The "functionality" or "functional characteristics" of GP900, P68 or cryptopain is defined by the interaction of antibodies to GP900, P68 or cryptopain and structural variants described, such that the antibody inhibits infection, invasion or adhesion of Cryptosporidium.

"The gene" or "genes encoding" means DNA encoding a portion or all of the GP900, P68 or cryptopain protein. One or more of these portions with or without carbohydrates attached include the targets of GP900, P68 or cryptopain antibodies.

"Sporozoites or merozoites" means any life stage which may invade host cells and any variant or mutant of said sporozoites or merozoites.

"Antibodies" means proteins which structurally interact with the target antigen and are produced when the antigen is introduced into an animal, such that they stimulate the immune system. The term also includes antibodies produced in vitro, such as antibodies produced by hybridoma cell cultures and chimeric proteins, as well as hybridoma cells and chimeric constructs introduced into the host to provide an in vivo antibody. The GP900, P68 or cryptopain protein has been identified as a target of anti-GP900, P68 or cryptopain antibodies which inhibit Cryptosporidium infection, invasion or adhesion.

"Antibodies to GP900" means proteins which structurally interact with the target antigen GP900.

"Antibodies to P68" means proteins which structurally interact with the target antigen P68.

"Antibodies to cryptopain" means proteins which structurally interact with the target antigen cryptopain.

"Antibody-antigen complex" means a detectable complex of the anti-Cryptosporidium antibody bound to the Cryptosporidium antigen.

"Monoclonal antibodies" means the monovalent antibodies produced by B cells fused to immortalized cells producing antibody specific to GP900, P68 or cryptopain.

"Polyclonal antibodies" means antibodies directed at GP900, P68 or cryptopain which are not monovalent and are the products of multiple B cells in character.

DETAILED DESCRIPTION OF THE INVENTION

This invention is based on finding that cryptosporidiosis can be detected and diagnosed with a great sensitivity using methods and kits of the invention comprising specific Cryptosporidium antigens GP900, P68 and cryptopain, antibodies raised against these antigens, DNA or RNA probes or primers derived from DNA of these antigens and the mutants, variants, analogs, and fragments thereof.

The invention, therefore, primarily relates to methods for detection and diagnosis of cryptosporidiosis in human and animal subjects and the environment.

More specifically, the invention concerns detection of the presence of Cryptosporidium antigen or antibody for diagnosis of prior or current infection in humans and animals and for detection of Cryptosporidium in the environment.

Cryptosporidium antigens described herein, in particular, are suitable for diagnosis of current or prior *Cryptosporidium parvm* infection by virtue of detecting antibodies to Cryptosporidium.

Polyclonal or monoclonal antibodies to the Cryptosporidium antigens are suitable for detecting the presence of Cryptosporidium in biological samples of the host or in the environmental samples.

The method for detection of the Cryptosporidium antigen presence in the biological or environmental samples comprises detecting antibody-antigen complex using specific monoclonal or polyclonal anti-Cryptosporidium antibodies to detect the presence of the antigen or detecting the presence of anti-Cryptosporidium antibody with Cryptosporidium antigen.

This invention also provides DNA and RNA encoding the Cryptosporidium GP900, P68 or cryptopain molecule, or a mutant, variant, analog and fragment thereof, and methods for production of recombinant or fusion proteins for use in detection/diagnosis.

This invention additionally discloses methods for preparation of the recombinant GP900, P68 or cryptopain antigens, mutants, variants, analogs and fragments thereof for production of monoclonal or polyclonal antibodies or probes for use in detection/diagnosis.

I. Detection of Cryptosporidium and Diagnosis of Cryptosporidiosis

This invention primarily concerns methods and means for detection of Cryptosporidium in the biological and environmental samples or for diagnosis of prior or concurrent Cryptosporidium infection.

The current method provides DNA and antibody for species identification and also for differentiation of isolate within species. The antigen, DNA and antibody probes are for specific functionally important proteins and therefore may detect virulence differences as well as isolate differences.

A. Detection of Cryptosporidium in Biological and Environmental Samples

The Cryptosporidium organism which causes cryptosporidiosis cannot be grown in vitro. This fact severely limits its detection in biological samples and in the environment because regularly used microbiological methods, such as culture, cannot be used for detection of fairly virulent Cryptosporidium.

The invention described herein stems from the availability of DNA and protein sequences of the antigens GP900, P68 and cryptopain discovered previously and described in patent applications and patents by inventors, namely the U.S. Pat. Nos. 6,071,518, 6,015,882, 5,643,772, and patent applications Ser. No.: 08/827,171, filed on Mar. 27, 1997, Ser. No. 08/071,880 filed on Jun. 1, 1993, Ser. No. 07/891,301, filed May 29, 1992, hereby incorporated by reference in their entirety.

Cryptosporidium antigens GP900, P68 and cryptopain isolated from different Cryptosporidium species and isolates are differentiated by PCR amplification and/or restriction length polymorphism analysis which defines a fingerprint for each particular isolate. PCR primers from regions flanking different portions of GP900, P68 or cryptopain are used for this differentiation. For example, discovery that the polythreonine rich domains of GP900 differentiate between isolates in fingerprinting assays enabled development of a specific method for detection of the isolates.

Diagnosis of Cryptosporidium infection and detection of organisms in environmental samples uses the principle of hybridization of complimentary strands of DNA and RNA which allows detection of the presence of the organism in a sample, by virtue of its unique nucleotide sequences. Intact RNA is associated with viability of an organism. Thus, detection of RNA in an environmental sample is be useful for determining if the environmental sample is infectious. Hybridization is the basic principle of several types of detection procedures.

Direct Hybridization

For direct hybridization, a portion of a diagnostic sample or an environmental sample containing the target DNA or RNA, obtained from Cryptosporidium, is prepared for hybridization and denatured so that it interacts with and binds to a DNA probe. The DNA probe is a piece of DNA, occasionally as small as 14 bp, but more typically several hundred to several thousand basepairs in length, which is denatured and allowed to interact with the prepared sample under conditions which are experimentally determined for each probe but are well known within the art. The conditions include variations in salt concentrations, temperature and washing conditions. The annealed complementary sequence of DNA containing a single sequence from the sample and a single sequence from the probe is detected by virtue of the incorporation of a label in the probe prior to the hybridization procedure. The label may be radioactive phosphate, biotin and a variety of other tags that are commercially available and are generally linked to the probe via a chemical reaction. The labeled probe is then detected in the sample via the appropriate detection procedure, i.e., for the mentioned labels, exposure to film or other methods of detection of radioactivity, reaction with a fluorescent or enzyme-linked streptavidin for detection of biotin via chemiluminescence or colorimetric assay.

Amplification of Specific Nucleic Acids in a Sample

In this application of the principle of hybridization, smaller amount of DNA or RNA in a sample is amplified so that the signal for detection is increased and the sensitivity of the procedure is enhanced. Single stranded PCR primers, typically 14 to 35 bp in length, are synthesized using portions of the DNA of the invention. Two primers separated by a distance which may vary from less than 100 bp to more than 5 kbp, but would generally be within those limits, are selected such that they are in opposite orientations and will, when utilized in a PCR reaction, result in the detection and amplication of the DNA which lies between them. An alternate technique utilizing branched DNA may also be utilized for amplification of the signal according to methods known in the art.

Primers are typically prepared when the sequence of DNA is determined. They are single-stranded. They may be used in sequencing reaction and in PCR reactions for detection and occasionally as probes, called oligonucleotide probes, in a direct hybridization reaction. In the latter instance, however, a larger piece of double stranded DNA is typically used as a probe after it has been denatured (i.e., rendered single stranded so that it can anneal with a DNA sequence in the sample). Herein, DNA probe is defined as a DNA segment which is an oligonucleotide or a larger segment of DNA which is used to detect complementary DNA or RNA sequences. DNA primers are defined as oligonucleotides which are used in enzymatic reactions which lead to the amplification of DNA.

List of a number of oligonucleotides presented in Tables 1, 3, 4 and 5 represents primers which have already been synthesized from the DNA sequence of GP900, P68 and cryptopain. These oligonucleotides are examples of DNA which can be used as PCR primers or as hybridization probes for detection purposes. Any larger segment of DNA can be amplified by PCR from Cryptosporidium DNA and also used as a probe. In this invention all primers and probes which can be made from the DNA sequences of GP900, P68 and cryptopain and used to detect Cryptosporidium DNA in diagnostic samples or environmental samples by way of direct hybridization or amplification methods are intended to be within the scope of this invention.

The PCR and hybridization methods described herein are extremely sensitive and permits detection of even one parasite molecule per volume when the appropriate primers and conditions are used. With a small number of parasite and the specific primers, the presence of Cryptosporidium and fingerprinting of the isolate using environmental or biological sample permit using the method of the invention.

In another mode, the detection method for environmental samples comprises contacting such a sample with the antigen or antibody of the invention for purposes of detecting Cryptosporidium. The detection method in biological samples comprises contacting a tissue body fluid, biopsy or solid specimen, with the antigen or antibody of the invention for purposes of detecting the presence of Cryptosporidium. Examples of body solid specimens are stool or tissue biopsies obtained from a subject. Examples of body fluids are blood, plasma, serum, saliva, urine, and the like.

Methods for the preparation of the tissue sample and the body fluid are standard in the art and are described, for example in *Manual of Clinical Microbiology*, Chapter 8, "Collection, Handling and Processing of Specimens", 4th edition, Eds, Lennette, E. H., Balows, A., Hausler, W. J. and Shadorny, A. J., American Society for Microbiology, (1986)), and examples of environmental samples include water, soil and foods grown in the environment.

Methods for actual detection of the presence of Cryptosporidium in the biological or environmental samples include but are not limited to polymerase chain reaction (PCR) amplification of the parasite DNA and detection of such amplified DNA by hybridization with probes, immunoreaction with antibodies, direct immunofluorescence, staining, microbiological or by any other method suitable for the detection of DNA as known now in the art or will become known in the future.

B. Detection of Cryptosporidium Isolates

The invention also permits detection and identification of individual Cryptosporidium isolates based on their genetic characteristics, herein called "a fingerprint". Fingerprints from each individual isolate were discovered and are further described below.

Differences between isolates of Cryptosporidium at the DNA level were previously described in *J. Protozool* 38: 405–415 (1991).

The current identification of these differences and production of DNA probes which differentiate these isolates using a small amount of isolate DNA makes possible the detection of Cryptosporidium in water, food, pet, nosocomial and person-to-person nonsexual and sexual exposure. The development of isolate-specific Cryptosporidium probes also permits determination of a latent state of Cryptosporidium infection.

Conserved PCR primers selected to amplify a polymorphic region of Cryptosporidium DNA from gastrointestinal tissue specimens of asymptomatic person will discover the presence of an organism which may later cause chronic cryptosporidiosis. Isolate specific probes also allow the differentiation of isolates according to their specific attributes, such as virulence, infectivity or host preference, for example for man, domestic or wild animals.

Detection of Isolate Specific DNA

The description presented above describes the detection of DNA from Cryptosporidium in general and is general enough to detect all Cryptosporidium species and isolates.

There are however, differences in sequences of different isolates of Cryptosporidium which may be exploited in order to detect and "thumbprint" different isolates. For example, the DNA of GP900 from 5 isolates has been completely or partially sequenced and contain only a limited number of variants in DNA sequence leading to the presence of different restriction sites in domains 1, 3 and 5. There are also regions of variability in length within the sequence, primarily in the poly-threonine regions of domains 2 and 4. Using these two features isolate differences may be detected in the following way. PCR primers are chosen to amplify a portion of GP900 DNA, generally including one of the threonine-rich domains. PCR fragments will be generated in all cases in which the primers were designed from the homologous isolate, in this case Iowa. In different isolates, they may be absent or vary in length. To further refine the isolate pattern, the PCR fragment is cut with restriction enzymes which cut in different locations in different isolate genomes. Comparison of the pattern of fragments as detected by electrophoretic separation will differentiate between the isolates and create a fingerprint. This example describes known differences in isolate DNA for GP900. It can be combined with PCR fragment amplification and restriction from the 5' and 3' flanking regions of GP900 (often these noncoding regions are quite variable) or from the locus of P68 and/or cryptopain to provide great sensitivity in distinguishing isolates. In addition, primers may be synthesized in regions of known DNA polymorphisms between isolates which result in the appearance or disappearance of a restriction site. These primers may be used to further distinguish between isolates by restriction length polymorphism analysis.

The detection of Cryptosporidium isolates depends on availability of conserved PCR primers which encompass polymorphic regions but which are conserved across *C. parvum* isolates and allow amplification and identification of isolate specific DNA from biological or environmental samples and other sources containing minute amounts of parasite material.

For the purposes of this invention, the following isolates of *Cryptosporidium parvum* were obtained: isolates which are geographically distinct (8); isolates which are temporally distinct (2), namely Iowa-1 and Iowa-2 isolates or isolates surmised to have been passed from one HIV-positive person to another by direct contact in the health care setting (2), SF-1 and SF-2. The temporally distinct isolates were obtained as Iowa isolate originally isolated from a calf in Ames, Iowa. Iowa-1 isolate was obtained from the NIH after the original Iowa isolate was propagated in Arizona. The Iowa-2 isolate was collected after the original Iowa isolate was propagated sequentially through 70 animals in Washington state under conditions instituted to minimize contamination. The geographically distinct isolates were from Peru, Brazil, Florida, Mexico, New York, AUCP-1 (Auburn, Alabama, Byron Blagburn); Iowa-1/Iowa-2; and SF-1/SF-2. The Peru, Brazil, Florida, Mexico and New York isolates were the same as those described in *Infect. Immunol.*, 58: 2071–2075 (1990) in 2-D gel experiments and in *J. Protozool.*, in genomic Southerns with pV47-2. Aliquots of these distinct isolates were obtained from Michael Riggs and were subjected to PCR using primers which flanked the domains of GP900. This analysis showed different fragment sizes which appeared to be in domains 2 and 4 and which differentiated some but not all isolates. Additional restriction site polymorphisms were identified when the DNA sequences were compared. Taking both observations together, better differentiation of isolates is achieved.

An average of $5 \times 10^8$ oocysts ($2 \times 10^9$ sporozoites) of each isolate was available in a largely purified form. $10^9$ oocysts of Iowa-2 was provided by Dr. L. Perryman. AUCP-1 and Iowa-1 isolates are available in $>10^9$ oocysts quantities. SF1 and SF2 are available in semipurified form which has been roughly quantitated at >5×10⁸. Oocyts were purified and DNA isolated as previously described in *J. Protozool.*, 38: 725–735 (1991). Using these techniques, 50–100 mg of Cryptosporidium DNA from 5×10⁸ oocysts were routinely isolated.

C. Diagnosis of Cryptosporidiosis

For diagnostic detection of Cryptosporidium in a subject, the sample of the subject's tissue, body fluid or stool is obtained. The sample is then prepared to permit isolation of the parasite oocyst, for example by dissolving the stool (100 mg-3 g) in a buffer, such as TES buffer, centrifuging the suspension, separating the supernatant containing oocysts and recentrifuging to obtain oocyst pellet. After isolating the oocysts, the oocysts are then submitted to lysing conditions where the oocyst releases DNA into the lysate. Lysate is then submitted to PCR DNA amplification with specific primers prepared as 15–35 bp oligonucleotides from GP900, P68 or cryptopain gDNA, when the released DNA is amplified into sufficient quantity. The amplified DNA is subjected to one of the detecting methods as described above, i.e., hybridization with the specific probe, immunodetection with Cryptosporidium specific antibody, with direct immunofluorescence, etc. In the alternative, the amplified DNA is applied on a column or another stationary phase, such as microsphere, conjugated with antibody, as a mobile phase, and the antigen-antibody complex is formed and detected by fluorescence, staining, radioactivity, etc. The body fluid samples or tissue biopsies are treated similarly. Various kits and detection assays are known in the art and are commercially available. All and any may be used in practicing this invention by exchanging the primers, probes or antibodies of the kit or assay with the specific primers, probes or antibodies of the invention as described herein. The specific primers for GP900, P68 and cryptopain are listed in Tables 1, and 3–5 and the preparation of other primers as well as probes and antibodies against GP900, P68 or cryptopain are described below.

D. Kits for Detection of Cryptosporidium

Kits for the diagnosis/detection of Cryptosporidium are used for determination of the presence or prior presence of the Cryptosporidium infection and environmental contamination, The kits comprise the antigen, antibody, DNA or RNA from GP900, P68 or cryptopain and a means for detecting the interaction of the materials of the invention with Cryptosporidium antigen, antibody, DNA or RNA in a host sample or Cryptosporidium antigen, DNA or RNA in an environmental sample.

The kit is utilized for the detection of endogenous antibodies/antigens/DNA/RNA produced by a subject that is afflicted with cryptosporidiosis or for detection of Cryptosporidium antigens/DNA/RNA present in the environmental samples. Due to the extreme sensitivity of the method of the invention, even at the early stages where the parasite is commencing invasion of the subject's cells or when the parasite is extremely diluted, such as in water, some amount of the Cryptosporidium antigen DNA/RNA is detectable in stool or water samples using the kit of the invention. The kit may detect either 1) the antigen with the monoclonal or polyclonal antibodies; 2) the presence of the anti-Cryptosporidium antibody with the antigen; or 3) the presence of DNA/RNA by hybridization with DNA or RNA probe, PCR amplification with GP900, P68 or cryptopain primers or other techniques which augment a DNA/RNA presence. The reactions of antigen, antibody or DNA, RNA detected by the kit include staining, radiography, immunoprecipitation, hybridization or any other means used in the art and suitable for these purposes.

In addition to the above, the kits may also comprise additional control compounds, such as anti-antibodies, protein A/G labeled or nonlabeled, and the like, suitable for conducting the various assays referred to above.

II. Cryptosporidium Protein/Glycoprotein Antigens

Cryptosporidiosis is a parasitic disease for which there are currently no effective diagnostic or detection methods available. The current invention identifies several specific Cryptosporidium antigens and provide their DNA and amino acid sequences thereby permitting detection of the minute amount of the parasite DNA and enhancing sensitivity of detection by many folds.

During the development of this invention, it has been shown that a *Cryptosporidium parvum* comprises several highly pathogenic proteins which differ in their genetic make-up. These proteins were further identified as GP900, P68, cryptopain and other proteins of various sizes as described in the prior application Ser. No. 07/897,301, incorporated by reference. Of these proteins three, namely GP900, P68 and cryptopain were further identified, cloned, tested for their pathogenicity and antibodies against these proteins were prepared.

1. GP900 Protein, Glycoprotein, Recombinant Protein and DNA/RNA

A. Identification of Protein GP900 as Cryptosporidium Antigen

Cryptosporidium antigen identified as GP900 protein is a high molecular weight glycoprotein of a Mr greater than 900 kilodaltons (kD). The GP900 protein was detected in micronemes of developing merozoites and sporozoites of the invasive stages of Cryptosporidium by immunoelectronmicroscopy and has been shown to be accessible to surface radioiodination with $^{125}I$. It is present on the surface of the sporozoites and is shed from the sporozoite surface in vivo in host cells. When deglycosylated, the GP900 core protein has a variable molecular weight of approximately 150–250 kD.

The GP900 protein antigen has been identified as a target of anti-GP900 antibodies which bind to it and form antigen/antibody complex. The GP900 protein was found to be highly abundant and easily visualized by Coomassie blue staining of proteins on SDS-polyacrylamide gels (SDS-PAGE) and is Triton X-100 soluble and N-glycosylated.

GP900 proteins were identified and isolated from oocysts of the Iowa, AUCP-1, NINC or other isolates of *Cryptosporidium parvum*, as described in Example 1 and tested for their interaction with specific anti-GP900 antibodies. Proteins which were shown to be targets of GP900 antibodies were prepared according to Example 2, and visualized by enzyme-linked immunosorbent assay (ELISA), chemiluminescence or with $^{125}I$-labeled Protein A followed by autoradiography as described in Example 7.

B. GP900 Gene Cloning/Sequencing and Genomic Southern Analysis

The GP900 gene of *Cryptosporidium parvum* was isolated from a naturally infected neonatal calf (NINC) isolate. DNA from the calf isolate was used to prepare a gt11 expression library containing overlapping clones which described a partial open reading frame (ORF) for GP900 which comprises 5163 bp nucleotides.

The complete coding sequence of the Iowa isolate GP900 gene, which shows high homology to the NINC gene, was also cloned and sequenced. The sequence was established by PCR using sequencing primers from the NINC sequence and template DNA of the Iowa isolate with subsequent cloning of overlapping sequences in pFusTrx or Bluescript for sequencing. At least two independent clones were sequenced in both directions to identify and correct PCR errors. The 5' region was sequenced from a 2.2 kb BamH1 fragment cloned into Bluescript.

C. Structure of the GP900 Gene and its Encoded Protein

Sequences identified as SEQ ID NOs: 1–4 are nucleotide sequences of the GP900 gene or gene fragment of Iowa or NINC isolates. The sequence identified as SEQ ID NOs: 5 and 6 are the corresponding proteins.

GP900 ORF encodes a multidomain protein based on predicted structural differences as seen in FIG. 1. FIG. 1A is a schematic drawing of the sequenced 7.6 kb locus showing the position of the open reading frame, domains, expressed fragments, Hinf 1 restriction sites (Hf1) and fragment and the hybridization probe DB8. The protein domain structure and expression clones (S34, ag4, domain 1 and domain 3) are indicated above the 7.6 kb locus. The locus is divided into a 1.5 kb 5' flanking region, a 5511 bp open reading frame and a 0.6 kb 3' flanking region. Vertical marks indicate the position of 22 Hinf 1 restriction sites within the open reading frame. Triangles mark each 1000 bp of DNA sequence. Inverted triangles mark the proposed methionine initiation site and the termination of the open reading frame. Three Hinf 1 restriction fragments and the hybridization probe DB8 are indicated below the 7.6 kb locus. FIG. 1B is deduced amino acid sequence and domains of the GP900 open reading frame. The five cysteines of domain 1 and the seven cysteines of domain 3 are underlined. The LDV motif of domain 1 is in bold print. In domain five representative 8-mer amino acid repeats and tandem repeats are underlined. A region containing the putative transmembrane segment is in bold print and underlined at amino acids 1745–1769. FIG. 1C is genomic Southern analysis of the GP900 locus using DB8 as the hybridization probe. Lanes 1–4 contain digested Iowa isolate DNA, lane 5 contains AUCP-1 isolate DNA. The restriction enzymes are: lane 1, Eco R1; lane 2, Bgl II; lane 3, Hin D III; lanes 4 and 5, Hinf 1.

Figure 4B:
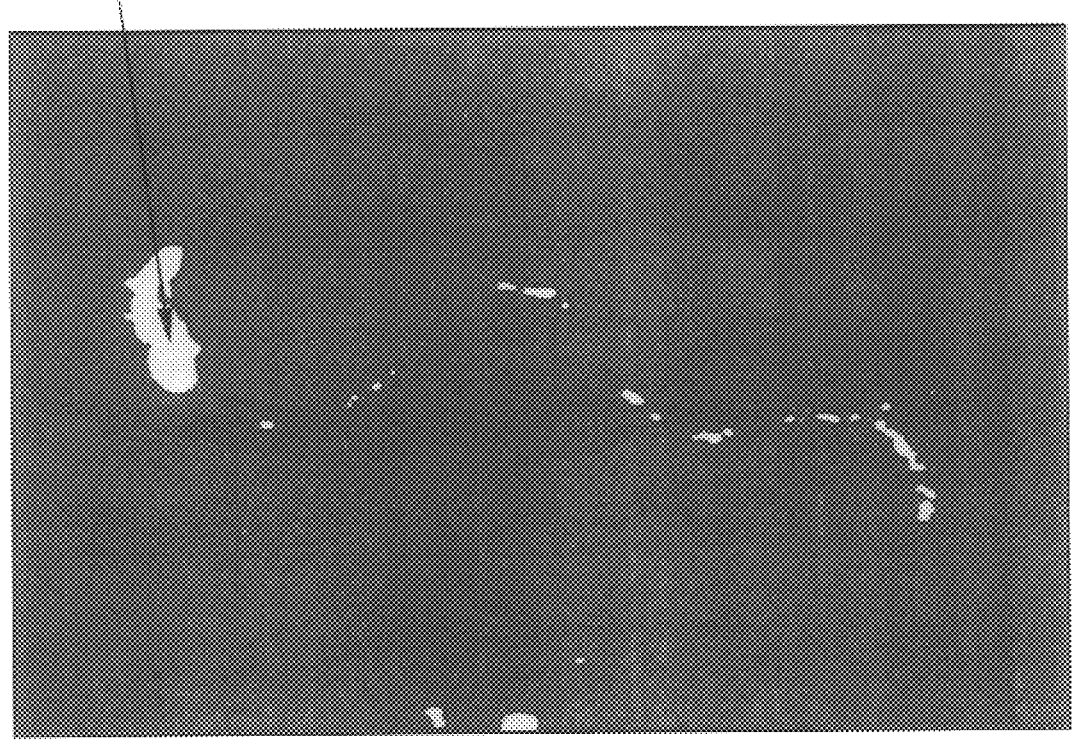

The predicted sequence GP900 open reading frame contains 5 structurally distinct polythreonine domains (SEQ ID NOs: 7–11) as seen in FIG. 4B.

Domains 1 (SEQ ID NO: 7) and 3 (SEQ ID NO: 9) of the protein are cysteine rich domains. Domains 2 (SEQ ID NO: 8) and 4 (SEQ ID NO: 10) are mucin-like domains containing large numbers of threonines.

Domain 1 (SEQ ID NO: 7) contains 5 cysteine residues in the Iowa isolate. Domain 3 has 7 cysteines in the Iowa isolate (SEQ ID NO: 9) but only 6 cysteines in the NINC isolate (SEQ ID NO: 6). Neither domain 1 or domain 3 is highly homologous to any known sequence in GenBank or Swiss Protein Bank.

Domain 2 (SEQ ID NO: 8) and domain 4 (SEQ ID NO: 10) are composed largely of threonine residues. Both domains also contain repeats of the sequence lysine-lysine-proline or lysine-proline. Variants of domain 2 (SEQ ID NOs: 6 and 12–20) consisting of two NINC isolates variants and eight Iowa isolates variants indicate that size and sequence variants are frequent in this domain. When the deduced protein sequence was analyzed by searches of the GenBank and Swiss Protein Bank, the greatest similarities were found between the threonine-rich regions of GP900 and other glycoproteins with either proven or putative 0-linked glycosylation including a variety of gastrointestinal mucins.

Domain 5 (SEQ ID NO: 11) is composed of a degenerate 8-mer repeat and contains a putative membrane spanning region and a cytoplasmic domain.

GP900 is both N- and O-glycosylated. GP900 has been shown to be susceptible to treatment with N-glycosidase F (N-glycanase) which cleaves high mannose and complex structures.

The presence of abundant cysteines on a surface protein of Cryptosporidium which is functionally homologous to the circumsporozoite protein of malaria strongly suggests that these cysteines participate in binding phenomena and may comprise new binding motifs. Numerous apicomplexan parasite proteins, such as Plasmodium, CSP, Duffy binding protein, EBA and PFEMPI have binding domains which contain cysteine rich regions. N- or O- linked carbohydrate moieties may also participate in binding to adjacent cells.

D. Expression of GP900 Recombinant Proteins

Recombinant GP900 protein useful in the method for diagnosis and detection of Cryptosporidium was cloned and expressed using methods described in Example 10.

Briefly, the S34 insert was subcloned into the glutathione-S transferase vector, expressed as a soluble protein and purified according to supplier's instructions.

Domain 3 (amino acids 520–678) and domain 1 (amino acids 164–303) corresponding to the terminal 139 amino acids of domain 1 which appeared to be a DNA duplication of domain 3 were expressed as thioredoxin fusion proteins in the vector pTrusFux according to supplier's protocols (Invitrogen).

Sense and anti-sense PCR amplification oligonucleotides, which allowed the amplification from Iowa genomic Cryptosporidium DNA of domain 1 or domain 3 with Kpn 1 and Xba I sequences at the 5' and 3' ends respectively, were synthesized. The sense oligonucleotides were: 5'-CAGGTACCCATGAATTGGCCGGTAAGTATC-3' (SEQ ID NO: 21) for domain 1 and 5'-CAGGTACCCTCTGAAACTGAGAGTGTAATT-3' for domain 3 (SEQ ID NO: 22). The antisense oligonucleotides were: 5'-CCTCAGATTAGTGTTTCACTCCAACACA-3' for domain 1 (SEQ ID NO: 45) and 5'-CCTCTAGATTATACGAAATCAGCTGAAGT-3' for domain 3 (SEQ ID NO: 46).

Amplified fragments were digested with Kpn I and Xba I, purified and introduced in a directional manner into the polylinker region of pTrxFus. Ligation products were transformed into G1724 *E. coli* and ampicillin resistant colonies were screened by hybridization of colony replicas with $^{32}$P-labeled domain 1 and domain 3. Purified colonies were grown in 1 ml aliquots for analysis. The identity of foreign DNA was verified by sequence analysis. Growth conditions were varied with respect to time and the bacteria lysed for evaluation of soluble and insoluble proteins. Domain 1 and domain 3 were wholly soluble. Yields were maximal at 3 hours of bacterial growth. Domains 1 and 3 were purified by heat treatment and their purity and concentration determined on Coomassie stained gels. Concentration was also determined using the Bradford reagent and UV detection at 595 nm.

E. Oligonucleotide Primers

Oligonucleotide primers suitable for PCR detection of GP900 antigen or a portion thereof are nucleotide sequences of about 14 to about 35 bp flanking the GP900 antigen or a portion thereof. The portion of the antigen may be any of its domains disclosed herein or a fragment thereof. The primer thus may be any 14–35 bp sequence flanking the whole GP900 antigen, any of its domain or any of its fragment.

The exemplary primers which were prepared are listed in Table 1.

TABLE 1

Sense primers 1. 5'-CAGGTACCCA TGAATTGGCC GGTAAGTATC-3'  SEQ ID NO: 21
2. 5'-CAGGTACCCT CTGAAACTGA GAGTGTAATT-3'  SEQ ID NO: 22
3. 5'-GGAAGGTTCA ATTGCAGG-3'  SEQ ID NO: 23
4. 5'-CCATTCAACC CTGTCACTGG AA-3'  SEQ ID NO: 24
5. 5'-GTCCATTCAA CCTGTC-3'  SEQ ID NO: 25
6. 5'-CAACTTATGT TGGTGTTATC GG-3'  SEQ ID NO: 26
7. 5'-CACTCTGGAT ATCAAACTTC A-3'  SEQ ID NO: 27
8. 5'-GGTTCCAGGT AAGCCACCAA T-3'  SEQ ID NO: 28
9. 5'-CAGGAATTTC TGCAAGTGAG TC-3'  SEQ ID NO: 29
10. 5'-ATGATATTGA GTCAGGTAGA CT-3'  SEQ ID NO: 30
11. 5'-CCCAATAATG AAGACACC-3'  SEQ ID NO: 31
12. 5'-TCAATCCACC AACTGGC-3'  SEQ ID NO: 32
13. 5'-CCAACAGCAC TGTCTCAGGA TC-3'  SEQ ID NO: 33
14. 5'-AACTTCAGGT ACTACAAAAC C-3'  SEQ ID NO: 34
15. 5'-CAGTCAATGG TGGAGGTG-3'  SEQ ID NO: 35
16. 5'-CTACTGGTAA CATTATTAAC CC-3'  SEQ ID NO: 36
17. 5'-AACTAATTAC CAATTCCAGG-3'  SEQ ID NO: 37
18. 5'-CAGATGAAGT AACAGGTTTG-3'  SEQ ID NO: 38
19. 5'-CAAGAGATCC AGTATCAGGA-3'  SEQ ID NO: 39
20. 5'-CAATTCCAGG TTCACATTC-3'  SEQ ID NO: 40
21. 5'-GATCACATTC TGGTACATTA T-3'  SEQ ID NO: 41
22. 5'-GGTCAAACCT ACCAGG-3'  SEQ ID NO: 42
23. 5'-CCAATTGATC CAATTAGTTA C-3'  SEQ ID NO: 43
24. 5'-GACTATAACA GTGGTTTATT A-3'  SEQ ID NO: 44

Antisense Primers 25. 5'-CCTCTAGATT AGTGTTTCAC TCCAACACA-3'  SEQ ID NO: 45
26. 5'-CCTCTAGATT ATACGAAATC AGCTGAAGT-3'  SEQ ID NO: 46
27. 5'-GATACAATGC AAGATTCGCT TCTAATACC TGC-3'  SEQ ID NO: 47
28. 5'-CCACAAGATC TTGAACCAGA AAT-3'  SEQ ID NO: 48
29. 5'-ATAGTGACCA GAGGGTTG-3'  SEQ ID NO: 49
30. 5'-CACTAGGCTC AGTGGTCTTA GT-3'  SEQ ID NO: 50
31. 5'-ATGTGTGCCT TGCTGCCC-3'  SEQ ID NO: 51
32. 5'-AAATCCAAAC TTCTATCTGG G-3'  SEQ ID NO: 52
33. 5'-AGTTGGTTTG CTTGGACTTC C-3'  SEQ ID NO: 53
34. 5'-TTTCGTCTCT CTTGGTA-3'  SEQ ID NO: 54
35. 5'-ACCGATAAAC CAGACATTG TT-3'  SEQ ID NO: 55
36. 5'-AGTCTACCTG ACTCAATATC AT-3'  SEQ ID NO: 56
37. 5'-ATTGGCTTTC CTGTTGAT-3'  SEQ ID NO: 57
38. 5'-TGGGTTAATA ATGTTACCAG TA-3'  SEQ ID NO: 58
39. 5'-GGATCATATG GCAAACCAG-3'  SEQ ID NO: 59
40. 5'-AATGTGAACC TGGAATTGGT T-3'  SEQ ID NO: 60
41. 5'-CTTCATTACT TGTTGGC-3'  SEQ ID NO: 61
42. 5'-GTCCTGTTGT TGGATCAG-3'  SEQ ID NO: 62
43. 5'-CACTGAAATA TTTACCAGAG-3'  SEQ ID NO: 63

It is to be understood that the primers listed in Table 1 are exemplary only and that any and all primers which meet conditions stated above are intended to be within the scope of this invention.

F. Production and Assay of GP900 Antibodies

Expressed portions of the GP900 loci are targets of polyclonal and monoclonal antibodies able to detect Cryptosporidium invasion. The expression, identification and isolation of these recombinant proteins allows production of recombinant proteins and antibodies to these proteins for the purpose of detection of Cryptosporidium in hosts or the environment and for diagnosis of prior or current Cryptosporidium infection in a suitable host.

Monoclonal antibodies, which are specific for GP900, have been made according to Example 2. Three of six antibodies, namely 10C6, 7B3, and E6, made from a single fusion event in which the immunogen was an oocyst containing sporozoites, were specific to GP900, suggesting that GP900 is a highly immunogenic molecule of sporozoites. Three of eight antibodies, namely M2, M15 and M24 made from a second fusion event, in which the immunogen consisted of meronts, were also specific to GP900, suggesting that GP900 is a highly immunogenic molecule of merozoites.

Antibodies, for the purposes of this invention, are not used as therapeutic agents but only as a tool for identification of GP900 proteins or glycoproteins and as a control component of the diagnostic kit.

Polyclonal antibodies against SDS solubilized GP900 and MAb 10C6, prepared according to Example 4, which were previously shown to detect GP900, were used for detection of molecular species which are immunoprecipitable with both mono and polyclonal antibodies. A Western blot probe of oocyst/sporozoite proteins is seen in FIG. 2. Immunoprecipitation of sporozoite surface labeled proteins with mono and polyclonal antibodies as seen in FIG. 3.

FIG. 2 shows an immunoblot of *Cryptosporidium parvum* oocyst/sporozoite proteins of the AUCP-1 isolate separated by SDS-PAGE. FIG. 2, lane 1 shows the MAb 10C6 culture supernatant, lane 2 shows the polyclonal anti-GP900 in 1:5000 dilution.

As seen in FIG. 2, a single molecular species, namely protein GP900, was identified at ~900 kD by both monoclonal and polyclonal antibodies. Cross-immunoprecipitation studies confirmed that the same protein of approximately 900 kD size, was detected by both antibodies. At prolonged periods of detection, a less prominent ladder of bands between the 200 and 92 kD markers was observed.

FIG. 3 shows immunoprecipitation of $^{125}$I radiolabelled *Cryptosporidium parvum* sporozoite surface proteins of the AUCP-1 isolate separated by 5–15% SDS-PAGE. FIG. 3, lane 1 shows radiolabelled *Cryptosporidium parvum* sporozoite surface protein control ($10^7$ sporozoites/lane). Lane 2 shows radiolabelled *Cryptosporidium parvum* sporozoite surface proteins immunoprecipitated with polyclonal anti-GP900.

As seen in FIG. 3, lane 2, immunoprecipitation of $^{125}$I labeled sporozoites with polyclonal anti-GP900 revealed that polyclonal anti-GP900 only detects one protein, GP900, at the surface of sporozoites. Polyclonal anti-GP900 antibody is thus an appropriate antibody for GP900.

In order to prepare reagents for specific portions of GP900 to assay their effects on sporozoite adhesion, invasion and intracellular development in vitro and infection in vivo, polyclonal antibodies were made to purified wild type β-galactosidase, and thioredoxin; Ag4-β-galactosidase and S34-β-galactosidase fusion proteins; and domain 1 thioredoxin, and domain 3 thioredoxin fusion proteins according to Examples 5 and 6.

In order to further define the antigen and S34 antibodies by removing the reactivity to β-galactosidase, affinity purified antibodies to the Ag4 and S34 portions of their fusion proteins were prepared according to Example 5. These various antibody preparations were used to probe an immunoblot of proteins from Cryptosporidium parvum oocysts/sporozoites as described in Example 7.

G. In vitro and In Vivo Assessment of Activity of Anti-GP900 and Anti-Recombinant GP900 Antibodies Since some antigens localized in the apical complex and extruded from it have been found to be adhesion molecules and the targets of inhibitory antibodies for other Apicomplexan parasites and to be suitable vaccine targets (*Cell*, 70:1021 (1992); *J. Immunol.*, 149:548 (1992)), antibodies to fusion proteins of four expression clones were prepared from the GP900 locus, domain l(amino acids 164–303), domain 3 (amino acids 520–678), S34 (amino acids 598–964) and Ag4 (amino acids 1030–1226) incorporated within SEQ ID NO: 5.

Immunoglobulin from unimmunized rabbits and rabbits immunized with domain 1 thioredoxin and domain 3 thioredoxin was affinity purified on protein A. Antibodies to S34 were more highly purified on a recombinant S34 affinity column and only antibodies to S34 were present in the final preparation.

Clearly, the clone S34 encodes a Cryptosporidium antigen and the antibodies specifically raised against this antigen are able to detect Cryptosporidium infection in vivo.

Thus antibodies against the recombinant S34 protein are able to detect Cryptosporidium infection in vitro and in vivo indicating the usefulness of the anti-S34 antibody for both anti-Cryptosporidium detection and diagnosis of a human or animal host.

H. GP900 Proteins, Variants and Oligonucleotide Sequences

Twenty-four sequences of GP900 identified as SEQ ID NO: 1–24 are disclosed. These sequences were prepared according to methods described in patent 6,071,518.

SEQ ID NO: 1 is the 7334 bp DNA sequence of the Iowa isolate comprised of the open reading frame and 3' and 5' flanking regions.

SEQ ID NO: 2 is the 5511 bp DNA sequence of the GP900 NINC Iowa isolate and is comprised of the ORF.

SEQ ID NO: 3 is the 5318 bp partial DNA sequence GP900 NINC isolate comprised of the partial ORF and 3' flanking region.

SEQ ID NO: 4 is a 5163 bp DNA sequence of GP900 NINC isolate and is comprised of the partial ORF.

SEQ ID NO: 5 is the deduced 1837 aa sequence of GP900 of the Iowa isolate.

SEQ ID NO: 6 is the deduced 1721 partial amino acid sequence GP900 of the NINC isolate.

SEQ ID NO: 7 is an amino acid sequence of domain 1 of GP900 of the Iowa isolate having 303 amino acids.

SEQ ID NO: 8 is an amino acid sequence of domain 2 of GP900 of the Iowa isolate having 216 amino acids.

SEQ ID NO: 9 is an amino acid sequence of domain 3 of GP900 of the Iowa isolate having 159 amino acids.

SEQ ID NO: 10 is an amino acid sequence of domain 4 of GP900 of the Iowa isolate consisting of 112 amino acids.

SEQ ID NO: 11 is an amino acid sequence of domain 5 which consisting of 1042 amino acids.

Sequences 12–19 are size and sequence variants comprising domain 2 of Iowa isolate.

SEQ ID NO: 12 is an Iowa isolate variant sequence comprising domain 2 (95 aa domain 2 and conserved flanking amino acids), consisting of 128 amino acids.

SEQ ID NO: 13 is an Iowa isolate variant sequence comprising domain 2 (97 aa domain 2 and conserved flanking amino acids), consisting of 130 amino acids.

SEQ ID NO: 14 is an Iowa isolate variant sequence comprising domain 2 (97 aa domain 2 and conserved flanking amino acids), consisting of 130 amino acids.

SEQ ID NO: 15 is an Iowa isolate variant sequence comprising domain 2 (105 aa domain 2 and conserved flanking amino acids), consisting of 138 amino acids.

SEQ ID NO: 16 is an Iowa isolate variant sequence comprising domain 2 (91 aa domain 2 and conserved flanking amino acids), consisting of 124 amino acids.

SEQ ID NO: 17 is an Iowa isolate variant sequence comprising domain 2 (142 aa domain 2 and conserved flanking amino acids), consisting of 175 amino acids.

SEQ ID NO: 18 is an Iowa isolate variant sequence comprising domain 2 (117 aa domain 2 and conserved flanking amino acids), consisting of 150 amino acids.

SEQ ID NO: 19 is an Iowa isolate variant sequence comprising domain 2 (58 aa domain 2 and conserved flanking amino acids), consisting of 91 amino acids.

SEQ ID NO: 20 is a NINC isolate variant sequence comprising domain 2, consisting of 249 amino acids.

SEQ ID NO: 21 is a sense oligo for domain 1 (216 aa domain 3 and conserved flanking amino acids), consisting of 30 bp.

SEQ ID NO: 22 is a sense oligo for domain 3 consisting of 30 bp.

SEQ ID NO: 23 is an antisense for domain 1, consisting of 28 bp.

SEQ ID NO: 24 is an antisense oligo for domain 3 consisting of 29 bp.

I. Variants and Mutants

Table 2 comprises an alignment of domain 2 protein variants. These consist of 8 variants (SEQ ID NOs: 12–19) of the Iowa sequence (SEQ ID NO: 5) and 1 variant (SEQ ID NO: 20) of the NINC sequence.

As seen in Table 2, domain 2 polymorphism of the GP900 contains variable numbers of threonine lysine and proline amino acids. Those are encoded by extensive trinucleotide repeats of the DNA end Sequence (SEQ ID NO: 6). Similar trinucleotide repeat regions occur and have been characterized in the genes responsible for a number of inheritable genetic diseases of man including fragile X syndrome. Insertions and deletions in these trinucleotide repeat regions are reflected in the translated protein which is functionally different. In addition, decreased amount of protein translation has been shown to occur if the repeats are extensive. DNA insertion and deletion are thought to be related to impaired function of DNA repair enzymes and polymerases in regions of perfect repeats. Domain 2 variants reported have from 91 to 216 amino acids in length. However, even longer variants are predicted by PCR of domain 2, including a large number of variants with a domain 2 size of 1.1 kb. These data suggest that domain 2 DNA is a "hot spot" for DNA recombination/mutation.

A method of producing amplified mutants and variants is described in Example 20. Specific variants or mutants Iowa isolate compared to NINC isolate domain 2 of the SEQ ID NO: 5 are shown in Table 2.

TABLE 2

Conservatively Modified Mutants and Variants of SEQ ID NO: 5

```
Var 2  MGSKVYIPYT KCVGVKH..T TTTTTTTTTT TTTTTTTTTT T.........TSEQ ID NO: 12
Var 3  MGSKVYIPYT KCVGVKHTTT TTTTTTTTTT TTTTTTTTTT T.........TSEQ ID NO: 13
Var 12 MGSKVYIPYT KCVGVKHTTT TTTTTTTTTT TTTTTTTTTT T.........TSEQ ID NO: 14
Var 1  MGSKVYIPYT KCVGVKHTTT TTTTTTTTTT TTTTTTTTTT TTTTTTTTTTSEQ ID NO: 15
Var 4  MGSKVYIPYT KCVGVKHTTT TTTTTTTTTT TTTTTTTTTT T..........SEQ ID NO: 16
Var 11 MGSKVYIPYT KCVGVKHTTT TTTTTTTTTT TTTTTTTTTT TTTTTTTTTTSEQ ID NO: 17
Var 9  MGSKVYIPYT KCVGVKHTTT TTTTTTTTTT TTTTTTTTTT TTTTTTTTTTSEQ ID NO: 18
Var 10 MGSKVYIPYT KCVGVKH... .......... .......... ..........SEQ ID NO: 19
NINC   MGSKVYIPYT KCVGVKHTTT TTTTTTTTTT TTTTTTTTTT TTTTTTTTTTSEQ ID NO: 20

Var 2  .......... .......... .......... .......TTT T..........
Var 3  .......... .......... .......... .......TTT T..........
Var 12 .......... .......... .......... .......TTT T..........
Var 1  .......... .......... .......... .......TTT T..........
Var 4  .......... .......... .......... .......... ..........
Var 11 TTTTTTTTTT TTTTTTTTTT TTTTTTTTTT TTTTKKPTTT T..........
Var 9  TTTTTTTTTT AT........ .......... .......TTT T..........
Var 10 .......... .......... .......... .......... ..........
NINC   TTTTTTTTTT TTTTTTTTTT TTTTTTTTTT TTTTTTTTTT TTTTTTTTTT

Var 2  .......... .......... .......... .......... ..........
Var 3  .......... .......... .......... .......... ..........
Var 12 .......... .......... .......... .......... ..........
Var 1  .......... .......... .......... .......... ..........
Var 4  .......... .......... .......... .......... ..........
Var 11 .......... .......... .......... .......... ..........
Var 9  .......... .......... .......... .......... ..........
Var 10 .......... .......... .......... .......... ..........
NINC   TTTTTTTTTT TTTTTTTTTT TTTTTTTTTT TTTTTTTTTT TTTTTTTTTT

Var 2  .......... .....TTTTT TTTTTTTTTT TTTTTTTTTT TTTTTTTTTT
Var 3  .......... .....TTTTT TTTTTTTTTT TTTTTTTTTT TTTTTTTTTT
Var 12 .......... .....KPTTT TTTTTTTTTT TTTTTTTTTT TTTTTTTTTT
Var 1  .......... .....TTTTT TTTTTTTTTT TTTTTTTTTT TTTTTTTTTT
Var 4  .......... ......TTTT TTTTTTTTTT TTTTTTTTTT TTTTTTTTTT
Var 11 .......... .....TTTTT TTTTTTTTTT TTTTTTTTTT TTTTTTTTTT
Var 9  .......... .....TTTTT TTTTTTTTTT TTTTTTTTTT TTTTTTTTTT
Var 10 .......... .......... ..TTTTTTTT TTTTTTTTTT TTTTTTTTTT
NINC   TTTTTTTTTT TTKKPTTTTT TTTTTTTTTT TTTTTTTTTT TTTTTTTTTT

Var 2  TTTKKPTTTT TTTTTTTTKK PTTTTTATTT TTTSETESVI KPDEWCWLCE
Var 3  TTTKKPTTTT TTTTTTTTKK PTTTTTATTT TTTSETESVI KPDEWCWLCE
Var 12 TTTKKPTTTT TTTTTTTTKK PTTTTTATTT TTTSETESVI KPDEWCWLCE
Var 1  TTTKKPTTTT TTTTTTTTKK PTTTTTATTT TTTSETESVI KPDEWCWLCE
Var 4  TTTKEPTTTT TTTTTTTTKK PTTTTTATTT TTTSETESVI KPDEWCWLCE
Var 11 TTTKKPTTTT TTTTTTTTKK PTTTTTATTT TTTSETESVI KPDEWCWLCE
Var 9  TTTKKPTTTT TTTTTTTTKK PTTTTTATTT TTTSETESVI KPDEWCWLCE
Var 10 TTT...TTTT TTTTTTTTKK PTTTTTATTT TTTSETESVI KPDEWCWLCE
NINC   TTTTKPTTTT TTTTTTTTKK PTTTTTATTT TTTSETESVI KPDEWCWLCE
``` wherein
F = phe        W = trp        I = ile
L = leu        R = arg        T = thr
S = ser        g = gly        P = pro
Y = tyr        E = glu        H = his
Z = OCH or AMB a = asp        Q = gln
C = cys        A = ala        N = asn
Z = OPA        V = val        K = lys
               M = met The NINC sequence seen in the Table 2, corresponds to amino acids 192–392 of the SEQ ID NO: 6. Iowa variant domain 2 sequences (SEQ ID NOs. 12–19) as seen in Table 2 correspond to amino acids 309–524 of SEQ ID NO: 5. Mutations or variations of the GP900 protein thus occur between isolates and within a given isolate.

2. P68 Protein, Recombinant Protein and DNA/RNA

A. Identification of Protein P68 as Cryptosporidium Antigen

The second antigen protein, designated P68 was identified. The P68 Cryptosporidium antigen is a smaller protein. The P68 protein was partially sequenced at the DNA level. The 3' sequence and 3' flanking regions for P68 are documented. Two P68 DNA sequences were established. SEQ ID NO: 64 comprising 1509 bp encodes a portion of P68. SEQ ID NO: 65 comprising 2380 bp encodes a portion of P68 and includes 3' flanking region. The deduced partial sequences of encoded protein P68 (SEQ ID NO: 66) were established.

A Cryptosporidium antigen designated P68 is an apical protein of sporozoites and merozoites. The protein has a size of between about 50–100 kDa. The P68 protein consists of 503 amino acids and its amino acid sequence is depicted as SEQ ID NO: 26. The P68 protein is derived from the gene S19. The DNA sequences encoding the P68 protein are depicted as SEQ ID NO: 65.

B. Cloning/Sequencing and Genomic Southern Analysis of the Gene for P68

The purification and initial characterization of the S19 clone and the description of the restriction fragment genomic expression library from which it was isolated have been described in (*Infect. Immun.*, 60:5132–5138 (1992)). A recombinant eluted antibody from the clone identified a dominant 68 kDa protein on Western blot of oocyst sporozoite proteins and was localized to the anterior end of the sporozoite by indirect fluorescent antibody analysis.

FIG. 5 is an immunoblot of AUCP isolate oocyst/sporozoite proteins. Lane 1 was detected with polyclonal anti-sporozoite/oocyst antibodies which had been affinity purified on the S19 fusion protein (Sl9-REA). As seen in FIG. 5, an immunoblot with the antibody identified the protein 68 kDa of Mr less than 69 kDa marker, known as protein. Lane 2 is REA prepared on wild type β-galactosidase as a negative control.

The S19 insert was subcloned into Bluescript and sequenced. The insert was used as a molecular probe to identify λgt11 expression library clones which extended 5' and 3' from S19. A 2380 bp locus was defined. The defined portion of the locus has 1509 bp of open reading frame which remains open at the 5' end.

C. Structure of the Gene and its Encoded Protein

FIG. 6 shows a restriction map of P68 open reading frame (ORF) DNA.

The sequences of the P68 gene fragment are shown in SEQ ID NOs: 64 and 65. The sequence of the corresponding protein is given in SEQ ID NO: 66.

D. Oligonucleotide Primers

Oligonucleotide primers suitable for PCR detection of P68 antigen or a portion thereof are nucleotide sequences of about 14 to about 35 bp flanking the P68 antigen or a portion thereof. The portion of the antigen may be any of its domain disclosed herein or a fragment thereof. The primer thus may be any 14–30 bp sequence flanking the whole GP900 antigen, any of its domain or any of its fragment.

The exemplary primers which were prepared are listed in Table 3.

Oligonucleotide primers for detection of P68 are listed in Table 3.

TABLE 3

P68 Oligonucleotide Primers

| | | |
|---|---|---|
| 1. | 5'-TAAGGGTCAA TTATTTAACC C | SEQ ID NO: 67 |
| 2. | 5'-TAATCCACTT CCATCACTAG | SEQ ID NO: 68 |
| 3. | 5'-CTAATTCCGT GAGCCTTTAA C | SEQ ID NO: 69 |
| 4. | 5'-CCTGGACTTG TTAAGCATAGAT | SEQ ID NO: 70 |
| 5. | 5'-TAATCCACTT CCATCACTAG | SEQ ID NO: 71 |
| 6. | 5'-CCCAGTAAGT AAGTTGTGTG | SEQ ID NO: 72 |
| 7. | 5'-CACATTAAAG ATGCAGGCAA CC | SEQ ID NO: 73 |
| 8. | 5'-CAGCATGTGC AACTGTTGGA | SEQ ID NO: 74 |
| 9. | 5'-TCAGCATGTG CAACTGTTGG AT | SEQ ID NO: 75 |
| 10. | 5'-TCTAGAAGAC TAGCTACTGG | SEQ ID NO: 76 |
| 11. | 5'-TTATGATGAT GAGATAATTA T | SEQ ID NO: 77 |
| 12. | 5'-AGAAGCAAGT ATTTCATACTC | SEQ ID NO: 78 |
| 13. | 5'-GAAAGCAGAT TCTCTGATAT | SEQ ID NO: 79 |
| 14. | 5'-ATTAGATCTC TTCTACATCA | SEQ ID NO: 80 |
| 15. | 5'-CCTAAGTGTT TCTTGCCCAA | SEQ ID NO: 81 |
| 16. | 5'-CCAGTTCTGG AAGTGCTCCA | SEQ ID NO: 82 |
| 17. | 5'-CTTGCTTCTT TATTATAATT | SEQ ID NO: 83 |
| 18. | 5'-CATCTTCTTA ATACCTACAA CA | SEQ ID NO: 84 |
| 19. | 5'-AATCCCCTTC AGCCTTTTG | SEQ ID NO: 85 |
| 20. | 5'-CAATGGTTTG GTTGAACAGA | SEQ ID NO: 86 |
| 21. | 5'-AGTAGGATTT GATGCGCGTA | SEQ ID NO: 87 |

Table 3 lists 21 exemplary sequences of primers suitable for detection of P68 antigen according to the invention.

It is to be understood that the primers listed in Table 3 are exemplary only and that any and all primers which meet conditions stated above are intended to be within the scope of this invention.

E. Production of P68 Recombinant Proteins

Using essentially the same methods as described for GP900 and for clones S34 and Ag4, S19 was subcloned into the pGEX expression vector to yield the expression clone GST-S19, a recombinant protein fused to glutathione S transferase. Antibodies were raised to GST-S19 in two rabbits and to the native GST, according to methods described in Examples 4 and 5.

E. In Vitro and In Vivo Assessment of Activity of Anti-P68 Antibody

Antibodies were assayed in vitro and in vivo as described in U.S. Pat. No. 6,071,518, incorporated by reference.

3. Cryptopain—*Cryptosporidium Parvum* Antigen

Cryptopain is cathepsin L-like cysteine proteinase.

A. Cryptopain Gene Cloning, Sequencing and Genomic Southern Analysis

In order to provide consistently the same antigen for production of antibodies or vaccines, and for recombinant production of fusion proteins and other agents useful for prophylactic therapeutic and diagnostic purposes, cryptopain was cloned, sequenced and genomic Southern analysis was performed to determine whether there was one or more cysteine proteinase similar to cryptopain.

Degenerative oligonucleotides were synthesized from the sequences encoding the active sites of papain like cysteine proteinases centered around the active site cysteine and histidine and around the active site arginine. The conserved cysteine and histidine residues are involved in the active site, and the cysteine residues are apparently involved in disulfide bridges. For cryptopain, the conserved cysteine is C-24, the conserved histidine is H-164. The proposed disulfide bridges are 21–65, 56–103 and 158–210.

Oligonucleotides specific for the *Plasmodium vinckei* cysteine proteinase were found to be suitable for and were therefore used to amplify a fragment of genomic DNA from Iowa isolate *Cryptosporidium parvum* oocysts.

The fragment was sequenced using methods described below and known in the art and found to encode a 459 bp portion DNA residues 869–1326 of a cysteine proteinase gene seen in FIG. 7. Protein sequence of cryptopain is shown in FIG. 8. The fragment (869–1326) was hybridized to an Iowa isolate genomic Southern blot which indicated that the cysteine proteinase was a single copy gene. Results are seen in FIG. 9.

Figure 9:
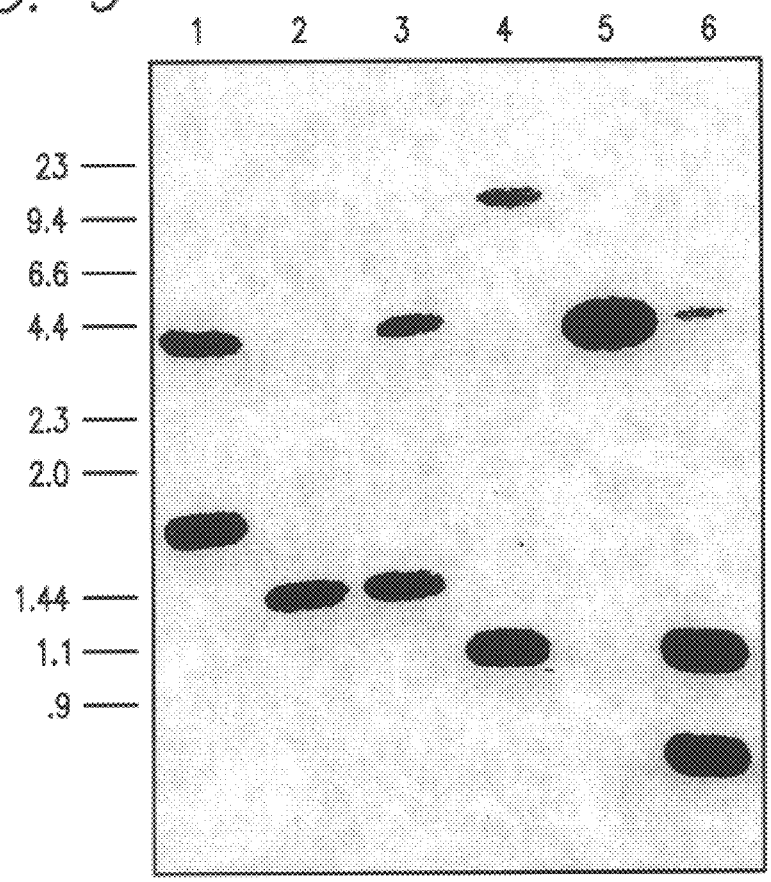
Figure 10:
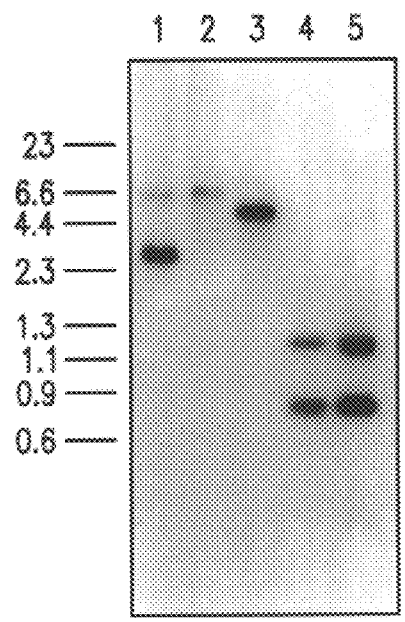

FIG. 9 is a genomic Southern analysis of Cryptosporidium DNA using the cryptopain probe. In FIG. 9, lane 1, the probe hybridizes to two Hind III fragments. These fragments are of approximate size 1.5 and 4 kb. In lane 2, the probe hybridizes with a Hae III fragment of 1.2 kb. In lane III the probe hybridizes to fragments of 1.2 and 4 kb of a Hind III/Hae III digest. In lane 4, the probe identifies fragments of 10 and 1 kb in an NsiI digest. In lane 5, the probe identifies a single band of 4 kb in an ScrII digest and in lane 6 it identifies fragments of 1.0, 0.5 and 4 kb in an NsiI/ScrII digests. The presence of 1 or 2 bands greater than the size of the probe in all digests indicates that the cysteine proteinase is a single copy gene.

The 459 bp Iowa fragment was then used to identify naturally infected neonatal calf (NINC) according to *Infect. Immun.*, 61:40 (1993) library clone which encoded the entire gene and 5' and 3' flanking regions. The sequence of this clone appears in FIG. 8 and is identified as (SEQ ID NO: 94). The sequence of the open reading frame was determined.

The corresponding sequences of the NINC clone and the 459 bp sequence of the Iowa cysteine proteinase isolate are identical indicating that cryptopain is highly conserved in these isolates and that its function is essential for Cryptosporidium.

SEQ ID NO: 88 is the DNA sequence of the Cryptosporidium cryptopain. The sequence (SEQ ID NO: 88) comprises 1663 base pairs and comprises 5' and 3' flanking sequences, pre, pro (SEQ ID NO: 89) and mature enzyme (SEQ ID NO: 90) sequences.

SEQ ID NO: 91 is the amino acid sequence of the cryptopain. The cryptopain contains 401 amino acids and contains pre and pro fragments (SEQ ID NO: 92), and mature enzyme (SEQ ID NO: 93).

Sequence ID NO: 96 is 459 bp residue representing a sequence of cryptopain probe.

Sequences identified as SEQ ID NOs: 95–106 are primer sequences.

Sequences SEQ ID NOS: 111–113 represent amino acid fragments of cryptopain.

Sequence SEQ ID NO: 116 represents a 1206 fragment of cryptopain DNA.

C. Structure of the Cryptopain Gene and Its Encoded Protein

The function of cryptopain is highly correlated with the structure of the protein which is determined by the corresponding sequence. In addition, regulation of the function is, at least in part, dependent upon the presence of the pro sequence.

Sequence identified as SEQ ID NO: 88 (FIG. 7) is a DNA sequence of cryptopain. Sequence identified as SEQ ID NO: 91 (FIG. 8) is its corresponding protein. Search of the Gene Bank and Swiss Protein Bank revealed that these sequences were highly homologous to cathepsin L-like sequences of various organisms.

D. oligonucleotide Primers

Oligonucleotide primers suitable for PCR detection of cryptopain antigen or a portion thereof are about 14 to about 35 bp nucleotide sequences flanking the cryptopain antigen or a portion thereof. The portion of the antigen may be any of its domain disclosed herein or a fragment thereof. The primer thus may be any 14–35 bp sequence flanking the whole GP900 antigen, any of its domain or any of its fragment.

Oligonucleotide primers for amplification of cryptopain are listed in Table 4.

TABLE 4

| Cryptopain Oligonucleotide Primers | |
|---|---|
| 1. 5'-GTTGAAGTTA ATTGAAC | SEQ ID NO: 95 |
| 2. 5'-GGTCCGAGAA ATATATTCC | SEQ ID NO: 96 |
| 3. 5'-CAAAGATACA GTAACAACC | SEQ ID NO: 97 |
| 4. 5'-GATTCACAGT ACATATAAAA GATTCC | SEQ ID NO: 98 |
| 5. 5'-GAGACTCTAC TTGACTTAAA TACC | SEQ ID NO: 99 |
| 6. 5'-ACAAACCGAG GATTACC | SEQ ID NO: 100 |
| 7. 5'-AACAAATTGC TGTTCACTCA AGC | SEQ ID NO: 101 |
| 8. 5'-ACTCGTTTGG CTAAGTATGG ACC | SEQ ID NO: 102 |
| 9. 5'-ATGCTCCTTG TGGAACCAAG | SEQ ID NO: 103 |
| 10. 5'-GCTAGTTTGA TGTATCC | SEQ ID NO: 104 |
| 11. 5'-GATTGATTAA TCACTGGATA C | SEQ ID NO: 105 |
| 12. 5'-GGTATATTGG TTGAGCC | SEQ ID NO: 106 |

The sense and antisense 7B1 and 7B2 primers are listed in Table 5.

TABLE 5

| Sense primers | | |
|---|---|---|
| 1. | AAAGGATCCT GC/TGGIA/TG/CITG C/TTGGGCITT | SEQ ID NO: 107 |
| 2. | TTTGAATTCC CAIG/CA/TA/GTTIC/T T/GIAC/TIATCCA A/GTA | SEQ ID NO: 108 |
| Antisense primers | | |
| 3. | CCAGGTACCA TGGACATAGG AAAC | SEQ ID NO: 109 |
| 4. | CCTCTAGATG CTTATATTGA TTG | SEQ ID NO: 110 |

Primers SEQ ID NO: 109 and 110 are 7B1 sense primers. Primers SEQ ID NO: 111 and 112 are 7B2 antisense primers for amplification of cryptopain or its fragments. These primers are degenerate primers for active site of cysteine proteinases used to identify the first cryptopain fragment in a library.

The active site cysteine shown at site 200 is embedded in a 7 amino acid all three enzymes and was one of the sites chosen to make degenerate oligonucleotides primers in Table 4. The conserved arginine at 392 is embedded in an amino acid fragment YWL/IVRNSW (SEQ ID NO: 112). Nonetheless, the degenerate oligonucleotide 782 containing sequence for VRNSW (SEQ ID NO: 113) and the active site cysteine oligonucleotide 781 were specific enough to amplify the 457 bp fragment (SEQ ID NO: 94).

D. Production of Cryptopain Recombinant Protein

Recombinant cryptopain proteins are useful as antigens for preparing antibodies which will inactivate cysteine proteinase and provide antibody probes to detect the presence of the organism in the environmental and clinical diagnostic setting. Their recombinant production is therefore important.

Recombinant proteins of the invention were produced. Generally, the 1203 bp cryptopain open reading frame (ORF) is engineered for in frame expression as a thioredoxin fusion protein in the Invitrogen vector pTrxFus, or any other suitable vector. The vector is used to create C-terminal fusions to E. coli thioredoxin. There is a multiple cloning site which allows in frame fusion of foreign protein with thioredoxin. Between the thioredoxin and the foreign protein there is an enterokinase cleavage site. Enterokinase treatment permits the release of thioredoxin from the protein. pTrxFus DNA is digested with for example KPNI and XbaI and the intervening fragment is removed for example, by gel purification.

Primers 7B1 and 7B2 were used to amplify the pre pro enzyme sequence from Iowa Cryptosporidium DNA. The primer 7B1 has a KpN1 site and the primer 7B2 has an XbaI site engineered into the 5' end of the oligonucleotides. These enzymes are used to digest the amplified DNA so that it could be inserted directionally and in frame into the KpnI/XbaI restriction digested pTrxFus. Then, the vector, such as pTrxFus, containing the sequence for the pre pro enzyme, is used to transform competent E. coli cells. Ampicillin resistant transformants are then analyzed for plasmid DNA by restriction with KpNI-XbaI and by sequence for the presence, orientation and reading frame of the gene. Clones containing the same gene are induced for expression of cryptopain and expression of the fusion protein, such as for example cryptopain-thioredoxin, at 57 kD, was analyzed by SDS-PAGE followed by immunoblot with antithioredoxin antibody.

Conditions of the actual preparation of recombinant cryptopain using vector pTrxFus described in application Ser. No. 08/827,171, incorporated by reference.

Fusion protein may be purified by osmotic shock or heat treatment of cell lysates to produce highly purified fusion protein. The fusion protein is advantageously cleaved with enterokinase at a cleavage site comprising 4 asparagine and 1 lysine sequence.

Production of cryptopain may be accomplished in multiple procaryotic or eukaryotic cells, including baculovirus, insect cells, yeast and mammalian cells. Cryptopain is purified by any suitable method known in the art, such as incorporation of histidine and purification by nickel chromatography, heat treatment of fluoredoxin fusion protein with subsequent harvesting of soluble protein.

UTILITY

The current invention provides a method and a means for detection of the Cryptosporidium parasite and diagnosis of infection. The following examples describe procedures used to prepare the antigens and antibodies of the invention and methods used for their detection. They are illustrative only and any modification using methods known in the art is intended to be included. The following examples are not to be considered in any way limiting.

EXAMPLE 1

*Cryptosporidium parvum* Parasites

This example illustrates the protocol used for isolation of *Cryptosporidium parvum* parasites.

Oocysts of the Iowa, NINC, AUCP-1 or other isolates of *Cryptosporidium parvum* described above were passaged through neonatal calves at the Animal Resources Services, University of California, Davis or obtained from a commercial source (Pat Mason) and the oocysts were purified and encysted. The detailed protocol is described in Infect. Immun., 61:4079 (1993). Oocysts containing sporozoites were solubilized, resolved by SDS-PAGE and subjected to immunoblotting, according to Infect. Immun., 60:5132 (1992).

EXAMPLE 2

Preparation of Murine Anti-Sporozoite Monoclonal Antibodies

This example describes the procedure used for preparation of murine anti-sporozoite monoclonal antibodies.
Polyclonal Antibodies 10 week-old female BALB/c mice were immunized four times intraperitoneally with approximately $5\times10^5$ sonicated $10^5$ *Cryptosporidium parvum* oocysts. The polyclonal antibody fraction of the ascites which was shown to react with the *Cryptosporidium parvum* sporozoite surface, the oocyst surface, and/or with internal antigens of the oocysts, was assessed by an IFA as described in Infect. Immun., 60:5132 (1992).

Monoclonal Antibodies

For monoclonal antibody production, mice treated as above were immunized intravenously with the supernatant from sonicated *Cryptosporidium parvum* oocysts three days before fusion as described in J. Immunol., 123:1548 (1979) and J. Parasitol., 68:1029 (1982). Hybridoma supernatants were used as the source of antibodies.

Six sporozoite monoclonal antibodies were obtained. The 10C6, 7B3 and E6 monoclonal antibodies were determined to react with GP900. The supernatants of the corresponding hybridoma cultures were used for immunofluorescence assay (IFA) studies and Western blots.

Using the same protocol, infected MDCK cells were used to immunize mice and 3 MAbs to GP900, namely M2, M10, M24 were produced.

Polyclonal and monoclonal antibodies against antigen P68 and cryptopain are prepared in the same way and/or as described in the application Serial No. 08/827,171 or U.S. Pat. Nos. 6,071,518, 6,015,882 and 5,643,772, incorporated by reference.

EXAMPLE 3

Detection of Traits of GP900 Deposited on Poly-L-lysine

This example illustrates detection of GP900 traits.

In order to determine whether GP900 was shed by the Cryptosporidium sporozoite in the absence of a specific antibody, living sporozoites were allowed to glide on poly-L-lysine coated microscopic slides. Slides were fixed in formalin and GP900 detected by incubation with MAb 7B3 followed by fluorescein labeled anti-mouse second antibody. MAb 7B3 had previously (data not shown) been shown to detect only one protein, GP900, in sporozoites.

The sporozoites were shown to be surrounded by GP900 which was shed posteriorly as the sporozoites glided on the poly-L-lysine coated slides. This reaction occurred in the absence of specific antibody which was added only for detection purposes after fixation of the sporozoites.

EXAMPLE 4

Production of Polyclonal Anti-GP900

This example describes the procedure used for preparation of anti-GP900 polyclonal antibodies.

The Triton X-100 (1%) soluble fraction of $2\times10^8$ oocysts was immunoprecipitated with MAb 10C6. A >900 kD MW species was identified in gels stained with Coomassie blue in water and excised. Frozen gel containing $2\times10^7$ oocyst/sporozoites was pulverized and emulsified in 150 µl PI of PBS and 150 µl complete Freund's adjuvant (CFA) for intraperitoneal (IP) immunization of mice.

Subsequently, the mice were immunized (IP) three times with the same antigen dissolved in incomplete Freunds adjuvant (ICFA) at approximately 2 week intervals. The anti-GP900 antibody at a dilution of 1:5000 recognized GP900 on Western blots.

Anti-P68 and anticryptopain polyclonal antibodies were prepared in substantially the same way and/or as described in the application Ser. No. 08/827,171 or U.S. Pat. Nos. 6,071,518, 6,015,882and 5,643,772, incorporated herein by reference.

EXAMPLE 5

Production of Polyclonal Antibody Against Ag4 and S34 Fusion Proteins

This example describes the procedure used for preparation of the anti-Ag4 and anti-S34 fusion protein polyclonal antibodies.

Lysogens were produced from the Ag4 and S34 gt11 clones. Cell lysates and purified protein were made using a protocol and reagents obtained from Promega. Purified fusion protein were emulsified in CFA and injected into rabbits. These injections continued at two week intervals with the substitution of ICFA. Rabbits were sacrificed at the end of 3 months and the antibody was assayed by Western analysis to verify that the antibody recognized a protein >900 kD.

The β-galactosidase and Ag4-β-galactosidase fusion proteins were purified essentially as described by Promega except that the buffering system used was phosphate buffered saline (PBS) pH 7.4. The purified fusion proteins were then coupled to CNBR sepharose using standard techniques. The antibodies to Ag4-β-galactosidase were depleted by passaging serum over a CNBR sepharose column coupled to β-galactosidase alone. The flow through fraction was applied to a CNBR sepharose column coupled to the purified Ag4 fusion protein. Antibodies directed against the Ag4 portion of the fusion protein were eluted in 0.1 M glycine at a pH of 2.4 and immediately neutralized in 200 µl of 2M Tris, pH 7.4. All affinity purified antibodies reacted with the fusion protein and the respective Cryptosporidium protein but not other E. coli proteins.

S34 was subcloned in GST and coupled to a column CNBR sepharose. Antibodies to S34-β-galactosidase were passed over this column. Antibodies directed against the S34 portion of the fusion protein were eluted in 1M Na thiocyanate and desalted and concentrated.

Anti-P68 and anti-cryptopain polyclonal antibodies were produced in substantially the same way and/or as described in the application Ser. No. 08/827,171 or U.S. Pat. Nos. 6,071,518, 6,015,882 and 5,643,772, incorporated herein by reference.

EXAMPLE 6

Production and Affinity Purification of Polyclonal Antibody Against GP900 Domain 1 and Domain 3 Fusion Proteins and Control Antibody This example describes production and purification of antibodies against GP900 domains 1 and 3 fusion proteins.

Purified domain 1 and domain 3 thioredoxin were prepared. Two to three µg of fusion protein after purification were emulsified in CFA or ICFA and injected at two week intervals. Rabbits were sacrificed at 3 months and the antibodies were assayed by immunoblot analysis to verify that they recognized GP900.

Polyclonal rabbit antisera from an unimmunized rabbit was evaluated for reactivity against Cryptosporidium antigens at a 1:1000 dilution on immunoblot and found to be free of reactivity. One ml of polyclonal rabbit antisera, anti-domain 1 or anti-domain 3 antisera was diluted with an equal volume of 100 mM Tris (pH 8.0) and passed through a 1 ml protein A bead column 2 times. After washing with 100 mM and 10 mM Tris (pH 8.0), the column was eluted with 100 mM glycine (pH 3.0) in a stepwise fraction. Aliquots of 500 µl were collected into 50 µl of 1.0 M Tris, pH 6.0. Antibody concentration was determined by absorbance at 280 nm and integrity of the Ig was verified by SDS-PAGE. Positive control antibody, HBC Ig 40529 has been previously described in Infect. Immunol., 61:(10); 4079 (1993).

EXAMPLE 7

Western Analysis

This example describes the Western analysis method used to identify the molecular targets of antibodies.

Oocysts ($10^6$ lane) were solubilized in denaturing sample buffer containing 5% βME (β-mercaptoethanol), resolved by SDS-PAGE and subjected to immunoblotting according to Infect. Immunol., 60:532 (1992). Proteins were visualized after incubation with primary antibody with $^{125}$I anti-rabbit or anti-mouse IgG conjugated with horseradish peroxidase or alkaline phosphatase followed by calorimetric or chemiluminescent development.

EXAMPLE 8

Southern Hybridization and Northern Blot Analysis

This example describes the Southern hybridization and Northern blot methods used for analysis of GP900 used for detection of Cryptosporidium.

A. Southern Hybridization

DNA was purified from 1×109 Cryptosporidium parvum oocysts as described in Example 1. DNA was digested with the restriction enzymes according to procedures provided by the manufacturer Promega. Digested DNAs were subjected to electrophoresis in 0.8% agarose gels in 1×TAE or 0.5× TBE. The gel was blotted to a nylon membrane (Hybond N+, Amersham) per manufacturer's instructions. The probe was labeled with $^{32}$P-ATP and hybridized to the membrane by methods known in the art. Results are seen in FIG. 6 where Lanes 1–4 show Iowa isolate DNA and Lane 5 shows AUCP isolate DNA. Lane 1, EcoRI digest; Lane 2, Bgl II digest; Lane 3, Hinf III digest; Lanes 4 and 5, Hinf I digest.

B. Northern Blot Analysis mRNA was purified from MDCK cells, or MDCK cells infected with sporozoites at a ratio of 1 oocyst/1 MDCK cell, harvested at 24 and 48 hours using guanidinium thiocyanate and oligo-dT cellulose isolation (Ambion mRNA purification kit, Albion, Inc., Austin, Tex.). Ten µg of poly-A RNA was separated on a formamide gel, transferred and hybridized as described for Southern hybridization. The Northern blot was probed with $^{32}$P-αdATP labeled domain 3 DNA and washed under stringent conditions.

EXAMPLE 9

Surface Radioiodination and Immunoprecipitation of Cryptosporidium Sporozoite Proteins This example describes the methods used for surface radio-iodination and immunoprecipitation of Cryptosporidium sporozoite proteins.

Oocysts were bleached, encysted and separated from sporozoites prior to iodination of the sporozoite surface and immunoprecipitation of surface proteins as previously described in Infect. Immun. (1993).

A membrane pellet was prepared by centrifuging 1.1×107 sporozoites per ml NETT (0.15 M NaCl, 5 mM EDTA, 0.5 M Tris, 0.5% Triton X-100, pH 7.4) at 100,000×g for 1 hour at 40° C. An aliquot of membrane proteins in 2% SDS 5% p-sample buffer was prepared for total sporozoite surface protein analysis. Aliquots of membrane proteins extracted in 2% SDS were diluted with 9 volumes NETT plus 1% high quality bovine serum albumin (BSA) obtained from Sigma; 1 volume 1% Triton X-100; proteinase inhibitors and either MAb 10C6 or anti-GP900 were added for overnight incubation. Protein A Sepharose 4B beads were added to immobilize the immunoprecipitated proteins. Parasite proteins were solubilized in 2% SDS sample buffer containing β-mercaptoethanol. Samples were boiled 5 minutes and separated by 5–15% gradient SDS-PAGE.

EXAMPLE 10

Cloning and Sequencing of a GP900 Locus

This example illustrates the procedure used for cloning and sequencing of a GP900 locus.

The purification and initial characterization of the S34 clone and the description of the restriction fragment genomic expression library of the NINC isolate from which it was isolated have been described in (*Infect. Immunol.*, 60:2343 (1992)). The Ag4 clone was isolated from the same library as an expression clone which reacted with polyclonal anti-GP900 antibody. The inserts of the S34 and Ag4 clones were subcloned into BlueScript obtained from Stratagene and sequenced in both directions using Sequenase Version 2.0 DNA Sequencing Kit (UBC) or cycle sequencing (New England Biolabs).

DB8, a 3154 bp insert, which contained the sequences of both S34 and Ag4 was identified by a double of screen of the library using these DNA inserts. PCR amplification products generated from the ends of DB8 and subsequent clones were used to screen the library to identify new clones which extend the sequence of the NINC isolate GP900 3' and 5'.

The Iowa sequence was established. The complete encoding sequence of the Iowa isolate GP900 gene, which shows high homology to the NINC gene, was also cloned and sequenced. The sequence was established by PCR using sequencing primers form the NINC sequence and template DNA of the Iowa isolate with subsequent cloning of overlapping sequences in pFusTrx or BlueScript for sequencing. At least 2 independent clones were sequenced in both directions to identify and correct PCR errors. The 5' region was sequenced from a 2.2 kb BamH1 fragment cloned into BlueScript.

The GP900 reading frame was verified by the inframe expression of S34 and Ag 4 as β-galactosidase fusion proteins and domains 1 and 3 as thioredoxin fusion proteins. All 4 fusion proteins elicited antibodies to GP900 when used to immunize animals (Data not shown). The FastA and blastp programs of GenBank were used to perform homology searches of the Swiss Protein database and showed homology of GP900 to mucin-like proteins.

P68 and cryptopain antigens were cloned and sequenced in substantially the same way or as described in the application Ser. No. 08/827,171 or U.S. Pat. Nos. 6,071,518, 6,015,882 and 5,643,772.

EXAMPLE 11

Purification of Recombinant GP900 Proteins

This example describes the purification procedure for GP900 proteins.

Iowa oocysts ($5\times10^8$) were excysted at 37° C. for two hours and pelleted at 4,000×g for 10 minutes at 4° C. The supernatant was aspirated and proteinase inhibitors were added to it to a concentration of pefabloc (AEBSF) 1 nM, leupeptin 20 μM, iodoacetamide 10 mM, PMSf 2 mM. The supernatant was concentrated by ultrafiltration to 350 μl (14.2×) (Centricon 10, Amicon). Silver stained SDS-PAGE gel of 10 and 20 μl aliquots revealed equal amounts of 47 kD, 120 kD and >900 kD proteins. The >900 kD protein was purified by ultrafiltration and (Centricon 100) and the concentration determined by silver stain and comparison to transferrin standards.

The substantially same procedure is used for purification of recombinant P68 and cryptopain, as described in the application Ser. No. 08/827,171 or U.S. Pat. Nos. 6,071,518, 6,015,882 and 5,643,772, incorporated herein by reference.

EXAMPLE 12

Preparation of Mutant and Variants of GP900

This example illustrates the method used to prepare mutant or variant products.

Genomic DNA from the Iowa and several other strains was subjected to PCR amplification using primers which were situated outside of domain 2, in the distal region of domain 1 and the proximal region of domain 3. Three prominent bands of different sizes were observed when the PCR products were visualized by ethidium staining of a gel in all of these strains. As a control for TAC polymerase, DB8 DNA was also amplified by the polymerase chain reaction. Only a 700 bp amplification product from DB8 was detected indicating that the multiple bands were a product of amplification of sequences present in the genomic DNA, and were not an artifact of the PCR process.

Two of the amplification product bands were cloned into sequencing vectors and 4 clones from each of the products were sequenced to determine their relationship to the NINC domain 2 sequence (Table 1). All 8 sequences had an open reading frame indicating that they were portions of DNA which could be the blueprint for a GP900 protein. All 8 sequences appeared to have in-frame (multiples of 3) DNA deletions with respect to the NINC sequence. All 8 coded for a domain 2 which had conservation of the threonine rich regions, but all 8 differed from each other. The DNA data indicate that mutation in domain 8 is common. The conservation of threonines and the in-frame nature of all 8 clones indicate that there are selection pressures acting at the level of the protein (presumably production of a functional protein which will allow for invasion and propagation) which determine which genotypic variants are maintained in a strain. Results show that there are mutants of GP900 which are maintained in an isolate's gene pool, presumably as variant alleles at a single locus in haploid stages of the organism.

Using a similar procedure, polymorphism of P68 and cryptopain is determined.

EXAMPLE 13

Preparation of Recombinant Domain 1 and Domain 3

This example describes the preparation of recombinant S34, Ag4, domains 1 and 3.

The oligonucleotide primers were synthesized at the Biomedical Research Center, University of California, San Francisco. A sense oligonucleotide (SEQ ID NOs: 21 and 22) are comprised of a KpnI restriction enzyme recognition site at the 5' end followed by coding sequence for the 5' end of the domain 1 sequence. The sense oligonucleotide for domain 3 is comprised of a KpnI restriction site at the 5' end followed by coding sequence for the 5' end of the domain 3 sequence. The anti-sense oligonucleotide for domain 1 is comprised of an Xbal sequence at the 5' end followed by the antisense coding sequence of the 3' end of the domain 1 sequence. The antisense Oligonucleotide for domain 3 is comprised of an Xbal sequence of the 5' end followed by the anti-sense coding sequence of the 3' end of the domain 1 sequence. When used as a pair of PCR amplification oligonucleotides, these oligonucleotides allowed the amplification from genomic Cryptosporidium DNA of the entire domain 1 and domain 3 sequences with Kpn 1 and Xba I sequences at the 5' and 3' ends, respectively.

The oligonucleotide sequences were designed so that after Kpnl and Xba I digestion of the amplification product, the resultant fragment could be introduced in a directional manner into pTrxFus which was cut with Kpnl/XbaI. Amplified and restricted DNA was visualized on a 0.8% agarose-1XTAE gel using ethidium bromide. The amplified and endonuclease restricted band was excised from the gel and purified using a glass bead technique (Gene-Clean).

pTrxFus was also digested with the enzymes KpnI and Xba I, enzymes uniquely present in the sequence in the poly linker, and the small intervening sequence was removed by gel purification as noted above. pTrxFus and domain 1 or domain 3 DNA, prepared in this manner, at 1:1 and 1:5 molar ratios were ligated overnight at 14° C. in the presence of ligation buffer and T4 DNA ligase at a concentration of 50–250 ng insert DNA/10 µl.

G1724 chemically competent cells were made as described by Invitrogen. Three to five µl of ligation mixes and control mixes were introduced into separate tubes of competent cells and the tubes were incubated on ice for 30 minutes. Tubes were incubated in a 42° C. heating block for 90 seconds and placed on ice for 2 minutes. Eight hundred µl of room temperature of enriched tryptone containing broth medium was added to each tube and the tube was incubated with shaking at 30° C. for 60 minutes. Twenty-five and 100 µl of each transformation mix was plated on RMG-Ampicillin transformation plates and the plates were incubated at 30° C., overnight.

Nitrocellulose membrane replicas of colonies were prepared from the transformation plates, the adherent cells lysed in alkaline solution and the DNA fixed to the membranes. Nitrocellulose membranes were hybridized with domain 1 and DNA 3 and positive colonies were purified. DNA was extracted from the relevant bacteria and the identity of the foreign DNA verified by restriction analysis and sequence analysis.

Purified colonies were grown in 1 µl aliquots for analysis. Growth conditions were varied with respect to time (2, 3, 4 hours) and the bacteria lysed for evaluation of soluble and insoluble proteins.

EXAMPLE 14

Detection of cryptosporidium in Stool Samples Using Monoclonal Anti-Cryptosporidium Antibody This example describes immunodetection of Cryptosporidium in stool samples.

After vigorous mixing, a 10-mL aliquot of stool was diluted 1:4 with 10% buffered formalin (Fisher Scientific, Pittsburgh). The diluted sample was agitated until complete suspension was achieved. A 5-µL aliquot was removed, placed in a defined area of a glass slide, and allowed to air dry. The slide was incubated with a fluorescein isothiocyanate-labeled monoclonal antibody M10 or 10C6 to GP900 Cryptosporidium oocysts antigen in a modified kit purchased from Meridian Diagnostics, Cincinnati. Positive and negative control reagents supplied with the kits were included in each test. Oocysts in 10×40 fields (2.5% of the sample area) were counted by fluorescence microscopy. If no organisms were seen, the entire slide was examined using a ×20 objective, and all oocysts were counted.

Each specimen was assayed on 3 separate days. The mean of triplicate counts in the 5-µL aliquot was standardized to the number of oocysts per milliliter of stool, taking into account the 1:4 dilution in preservative. Total oocyst excretion per specimen was calculated by multiplying the mean concentration (oocysts/milliliter) by stool weight (grams). Total daily oocyst excretion was the sum of oocysts in each specimen in a 24-h period.

EXAMPLE 15

Detection of Cryptosporidium in Biopsy

This example describes the procedure for detection of Cryptosporidium in tissue biopsy samples.

Duodenal biopsy specimens were obtained at the time of upper gastrointestinal endoscopy. The samples were homogenized and homogenate was solubilized by subjecting the portion of homogenate to β-mercaptocthanol or sodium hydroxide. The suspension was treated similarly to the stool sample and reacted with the specific antibody 7B3 to GP900. Additionally, the second fluorescein conjugated antibody E6, M2 or M24 is added and the formation of fluorescence for antigen-antibody complex is detected.

EXAMPLE 16

PCR Assay for Detection of Cryptosporidium DNA in Feces

This example describes conditions for PCR assay for detection of DNA from Cryptosporidium.

DNA extraction of oocyst from stool was performed as follows. One-gram portions of fecal material were mixed with 40 ml of 0.35% sodium hydrochloride until suspension was formed. Twenty milliliters of the suspension was shaken for ½ min and centrifuged at 1,600×g for 15 min. The pellet, resuspended in 15 ml of deionized water, was layered over a two-layer sodium chloride gradient (specific gravities, 1.1 and 1.05) interface and was diluted with 10 ml of deionized water, and half of this suspension was filtered through a 3-µm-millipore filter. The filter was washed with 3 ml Tris HCl (pH 8). Recovery of the oocysts was completed by shaking the filters for 30 seconds in the tubes with Tris HCl. After discarding the filters, the samples were centrifuged at 16,000×g for 3–5 min and the final pellet was recovered in 50 µl of 10 mM Tris HCl (pH 8) were lysed for DNA extraction, as described in Example 10.

The PCR amplification of Cryptosporidium Iowa isolate domain 3 was performed as follows. For each sample analyzed, 10 µl of lysate was used as a template in 50-µl reaction mixtures containing 75 mM Tris (pH9), 20 mM $(NH_4)_2SO_4$, 0.1% (wt/vol) Tween 20, 2 mM $MgCl_2$, 0.2 mM (each) dGTP, dATP, and dCTP, 0.6 mM dUTP, 50 pmol (each) of primers 5'-CAGGTACCCA TGAATTGGCCGGTAAGTATC-3' SEQ ID NO: 21, 5'-CAGGTACCCT CTGAAACTGAGAGTGTAATT-3' SEQ ID NO: 22, 5'-CCTCTAGATTA GTGTTTCACTCCAACACA-3' SEQ ID NO: 45, 5'-CCTCTAGATTATACGAAATC AGCTGAAGT-3' SEQ ID NO: 46, 0.5 U of uracil-N-glycosylase (UNG; Boheringer Mannheim), and 1 U of Taq DNA polymerase (Eurogentec). Reaction mixtures were incubated for 10 min at 22° C. and after denaturation at 94° C. for 10 min, the samples were subjected to 50 cycles of 1 min at 94° C., 90 seconds at 56° C., and 90 seconds at 72° C., followed by a 5-min extension at 72° C. PCR products were then suspended in the sample buffer containing 1.2 M urea, 3.4% saccharose, 10 mM EDTA, and 0.002% bromophenol blue, and 10 µl was analyzed on horizontal agarose gels in TAE buffer (40 mM Tris acetate, 2 mM $Na_2$ EDTA-$2H_2O$). Each amplification run contained a negative control (extraction buffer) and a positive control (genomic DNA from Iowa isolated domain 3).

EXAMPLE 17

Detection of Cyclosporidium in Stool

This example describes the techniques used for detection of Cryptosporidium in stool samples using specific anti-GP900 antibodies.

Fresh fecal specimens were obtained for detection of Cryptosporidium antibodies. Fecal samples were diluted one in three (weight by volume) with distilled water and thoroughly mixed using a vortex mixer.

From each of the fecal samples, a sample of 10 μl was separated and smeared on marked areas of 1 cm² on glass microscope slides. Three smears were prepared from each of the ten samples, and these were stained with either Mab 10C6, M2 or M10. Examination was performed at ×400 magnification under bright-field microscopy, and fluorescence microscopy. Total and average numbers of oocysts were recorded for every ten fields in each smear. Negative control smears were prepared from samples which were not inoculated with oocysts.

EXAMPLE 18

Preparation of Probes and Primers

This example describes the procedure used for the preparation of probes and primers.

Preparation DNA Probe

The probe were prepared by the modified method described in *Am. J. Trop. Med. Hyg.*, 45: 688–699 (1991).

Purified Cyclosporidium genomic DNA of GP900, PG8 cryptopain or fragment thereof was digested to completion with the restriction enzyme Hind III, and the resultant fragments ligated into PUC18 plasmid vectors. These vectors were used to transform the DH5 α strain *Escherichia coli* host bacteria, which were plated on Luria-Bertani (LB) agar supplemented with ampicillin (50 μg/ml), 20 mm isopropyl β-D-thio-galactopyranoside (IPTG), and 5-bromo-4-chloro-3-indolyl β-D-galactopyranoside (X-gal) (80 μg/ml), and incubated overnight.

A colony hybridization procedure was performed and filters were screened with $^{32}$P-labeled, genomic Cyclosporidium DNA obtained from GP900, P68 or cryptopain Cryptosporidium antigens. Duplicate filters were screened by the same method using genomic DNA from *G. lamblia*, *P. falciparum*, *Toxoplasma gondii*, and *Trichomonas vaginalis*.

Individual colonies that hybridized only with Cyclosporidium DNA were grown overnight in 5 ml of LB medium, and the DNA was extracted by the mini-prep procedure according to method described in *Molecular Cloning: A Laboratory Manual*, 2$^{nd}$ Ed, Cold Harbor Spring Laboratory Press (1989). One clone designated GP900 as defined above, was selected and sequenced by the Sanger dideoxy chain termination method using a Sequenase® (United States Biochemicals, Cleveland, Ohio.) kit. Sequence data were analyzed with MicroGenie software (Beckman Instruments, Palo Alto, Calif.), and compared with GenBank and National Biomedical Research Foundation databases for homology with DNA and amino acid sequences, respectively.

Preparation of Oligonucleotide Primers

A pair of 26-base primers and two 20-base probes homologous to the central region of the 452-base target sequence were synthesized in an Applied Biosystems (Foster City, Calif.) model 380 B DNA Synthesizer according to manufacturer's specifications.

Primers for detection of GP900, P68 or cryptopain were prepared as above and their sequences are listed in Tables 1 and 3–5.

EXAMPLE 19

Polymerase Chain Reaction for Detection of Cryptosporidium Isolates

This example describes PCR amplification procedure used for detection of Cryptosporidium isolates.

DNA sequence from GP900 P68, cryptopain or a fragment comprising approximately 400 bp was selected as the target for amplification by PCR. The PCR reaction mixture (final volume 103 μl) consisted of 68.5 μl of sterile, distilled, deionized water, 10 μl of 10×PCR reaction buffer (500 mM KCl, 100 mM Tris-HCl, pH 8.4, 15 mM $MgCl_2$, 0.1% gelatin), 10 μl of 2 mM nucleotide mix, 0.5 μl (2.5 units) of Taq DNA polymerase (Bethesda Research Laboratories, Gaithersburg, Md.), 2 μl of 100 mM primer (1 μl each of forward and reverse primer), 2 μl of dimethylsulfoxide, and 10 μl of sample DNA.

Prior to adding the DNA samples, the mixtures were irradiated for 5 min with a UV transilluminator to destroy any contaminating DNA that might have been accidentally introduced. This mixture was centrifuged at 12,000×g for 15 seconds and covered with 75 μl of mineral oil (Sigma, St. Louis, Mo.). A positive control, consisting of linearized plasmid, purified *C. parvum* DNA, or amplified product, and three negative controls, consisting of reaction mixtures minus Taq DNA polymerase, primers, or template DNA, were used in each experiment. Reactions were carried out in a Perkin-Elmer (Norwalk, Conn.) DNA Thermal Cycler. Samples were denatured at 94° C. for 1 min, annealed at 45° C. for 2 min, and extended at 72° C. for 3 min. This cycle was repeated 35 times, followed by a 9-min incubation at 72° C.

Following the PCR, DNA hybridization and detection was performed.

10-μl aliquots of product were electrophoresed on 6% polyacrylamide gels and 1.8% agarose gels. The gels were stained with ethidium bromide and viewed under ultraviolet light, and the resultant band patterns were photographed. The DNA bands in the agarose gels were then transferred to Hybond-N nylon membranes (Amersham, Arlington Heights, Ill), using a Bio-Rad (Richmond, Calif.) Model 785 vacuum blotter, with a transfer time of 90 min. Transferred DNA was alkali-fixed to the membranes by soaking them on sheets of Whatman (Waltham, Mass.) filter paper that was saturated with 0.4 M NaOH for 20 minutes, then rinsed for 1 minute in 5×SSC (1×SSC=0.15 M NaCl, 0.015 M sodium citrate).

A 20-base synthetic oligonucleotide probe corresponding to the middle portion of the target segment was 3'-end-labeled with digoxigenin-11-dUTP (Boehringer Mannheim, Indianapolis, Ind.), following the manufacturer's directions included in the Genius non-radioactive DNA labeling and detection kit. Briefly, the following components were added in order to a 500 μl reaction tube: 4 μl of 5×terminal transferase reaction buffer, 1.2 μl of $CoCl_2$, 2.5 μl of digoxigenin-11-dUTP, 1 μl of probe (35 pmoles), 1 μl of DATP (0.1 nmoles), 8.3 μl of sterile water, and 2 μl of terminal transferase. The reaction mixture was incubated at 37° C. for 5 min, precipitated with 0.4 M LiCl and ethanol, vacuum-dried, and resuspended in 20 μl of TE buffer with 0.1% SDS. Molecular size markers electrophoresed with the PCR samples consisted of a Hind III digest of λ DNA and a Hae III digest of ΦX174 RF DNA with digoxigenin-11-dUTP.

Membranes were prehybridized for 1 hr at 42° C. in 5×SSC, 5% (w/v) SDS, and 50% (v/v) formamide (hybridization solution). After prehybridization, the membranes were transferred to heat-sealable bags. Approximately 2 ml of hybridization solution was added to the bags, followed by 10 μl of digoxigenein-11-dUTP-labeled probe and 1 μl of labeled λ and ΦX174RF marker DNAs. The bags were heat-sealed and hybridized overnight in a circulating water bath at 42° C. After hybridization, the membranes were washed twice (5 min/wash) at room temperature in 50 ml of 20×SSC, 0.1% 9w/v) SDS, followed by two washes (15 min/wash) in 0.1% (w/v) SDS at 50° C. Prior to antibody labeling, the membranes were equilibrated for 1 min at room temperature in 100 mM Tris-HCl, pH 7.5, 150 mM NaCl. The membranes were then blocked in 100 mM Tris-HCl, pH 7.5, 150 mM NaCl, and 2% (w/v) blocking reagent and anti-digoxigenin alkaline phosphatase conjugate at a working concentration of 150 mU/ml, and incubated at room temperature for 30 min with gentle agitation. The membranes were then washed twice (15 min/wash) in 100 mM Tris-HCl, pH 7.5, 150 mM NaCl, at room temperature. After they were washed, the membranes were equilibrated for 2 min in 100 mM Tris-HCl, pH 9.5, 100 mM NaCl, 50 MM $MgCl_2$. Approximately 3 ml of chemiluminescent substrate, Lumi Phos 530® (Boehringer Mannheim), was added to a plastic dish. The membranes were pulled through the Lumi Phos 530® to wet them, excess liquid was allowed to drip off, and the membranes were sealed in hybridization bags. The membranes were then incubated at 37° C. for 30 min to allow light emission to reach a steady state, and then exposed to Kodak (Rochester, N.Y.) x-ray film for 5–15 min. Films were developed in a Kodak X-Omat processor.

What is claimed is:

1. A method for detection of a Cryptosporidium species or isolate in a biological and environmental sample, said method comprising steps:
   a) obtaining the biological or environmental sample;
   b) contacting the sample of step (a) with an Cryptosporidium GP900, P68 or cryptopain antigen, DNA or RNA or with a specific anti-Cryptosporidium GP900, P68 or cryptopain antibody,
      wherein said GP900 antigen is a protein comprising 1832 amino acids depicted by SEQ ID NO: 5 or a protein depicted by any of the SEQ ID NOs: 7–19, or a protein comprising 1721 amino acids depicted by SEQ ID NO: 6 or a protein depicted by SEQ ID NO: 20;
      wherein said P68 antigen is a protein comprising 503 amino acids depicted by SEQ ID NO: 66 or a protein encoded by the nucleotide sequence depicted by SEQ ID NOs: 64 and 65;
      wherein said cryptopain is a protein comprising 401 amino acids depicted by SEQ ID NO: 91 or a protein depicted by any of the SEQ ID NOs: 92, 93 or 111–113;
      wherein said GP900 DNA is a nucleotide sequence comprising 7334 base pairs, 5511 base pairs, 5318 base pairs or 5163 base pairs, depicted by SEQ ID NOs: 1–4 or a nucleotide sequence encoding a protein depicted by any of the SEQ ID NO: 7–20; and
      wherein said P68 DNA is a nucleotide sequence comprising 2380 base pairs depicted by SEQ ID NO: 65 or 1509 base pairs depicted by SEQ ID NO: 64; and
      wherein said cryptopain is a nucleotide sequence comprising 1663 base pairs, 534 base pairs, or 678 base pairs, depicted as SEQ ID NOs: 88–90 or a nucleotide sequence depicted by SEQ ID NOs: 94 and 114; and
      wherein said antibody is monoclonal or polyclonal; and
   c) detecting a formation of an antigen-antibody complex, or a presence of DNA or RNA;
      wherein a presence of said antigen-antibody complex, or a presence of DNA or RNA indicates a presence and a positive detection of Cryptosporidium in the sample and an absence of such complex, or absence of DNA or RNA indicates an absence of Cryptosporidium.

2. The method of claim 1 wherein the biological sample is blood, plasma, serum, urine, stool or saliva and wherein the environmental sample is water or soil.

3. The method of claim 2 wherein the Cryptosporidium is detected immunologically.

4. The method of claim 3 wherein the immunological detection comprises contacting the biological or environmental sample with monoclonal antibodies raised against GP900, P68 or cryptopain antigen, variant, mutant or fragment thereof.

5. The method of claims 4 wherein the presence of antigen-antibody complex in the sample is detected by immunodetection, fluorescence, staining, or radio-labeling.

6. The method of claim 5 wherein the antibody is labeled with radio-label or with fluorescence.

7. The method of claim 6 wherein the antibody is the monoclonal antibody identified as M2, M10, M15, M24, E6, 7B3 or 10C6.

8. The method of claim 3 wherein the antibody is polyclonal.

9. The method of claim 1 wherein the Cryptosporidium GP900, P68 or cryptopain antigen is detected with polymerase chain reaction (PCR) or by hybridization.

10. The method of claim 9 wherein the PCR or hybridization is performed on the sample pretreated to release a Cryptosporidium oocyst DNA.

11. The method of claim 10 wherein the hybridization is a direct hybridization with DNA and wherein PCR comprises an amplification of a specific nucleic acid sequence comprised within DNA released from the Cryptosporidium oocyst.

12. The method of claims 10 wherein the released DNA is contacted with a pair of oligonucleotide primers comprising of about 14 to about 35 base pairs flanking the GP900, P68 or cryptopain antigen.

13. The method of claims 12 wherein a primer oligonucleotide sequence for detection of GP900 is selected from the group depicted by SEQ ID NOs: 21–63, wherein a primer oligonucleotide sequence for detection of P68 is selected from the group depicted by SEQ ID NOs: 67–87, and wherein a primer oligonucleotide sequence for detection of cryptopain is selected from the group depicted by SEQ ID NOs: 95–110.

14. The method of claim 13 wherein the primers for a detection and amplification of the DNA positioned between said primers are selected to be in opposite orientations.

15. The method of claim 11 wherein the Cryptosporidium DNA is detected by the direct hybridization.

16. The method of claim 15 wherein for the hybridization, the sample is denatured and reacted with a DNA probe.

17. The method of claim 16 wherein the probe is denatured to a single stranded DNA complementary to the DNA of the GP900 depicted by SEQ ID NOs: 1–4 or to a nucleotide sequence encoding a protein depicted by SEQ ID NOs: 7–19, or to the DNA of the P68 depicted by SEQ ID NOs: 64 or 65 or a nucleotide sequence encoding a protein depicted by SEQ ID NOs: 66, or to the DNA of the cryptopain depicted by the SEQ ID NOs:88–90, 94 or 114.

18. The method of claim 17 wherein the probe is labeled.

19. The method of claim 18 wherein said probe is labeled with a radioactive phosphate, biotin or a chemical tag.

20. The method of claim 19 wherein the labeled probe is detected with exposure of radiolabel on a film, detection of radioactivity, reaction with a fluorescent or enzyme-linked streptavidin, chemiluminescence or colorimetry.

21. The method of claim 1 wherein said protein comprising 1832 amino acids depicted as SEQ ID NO: 5 or a protein depicted by any one of the SEQ ID NO: 7 through SEQ ID NO: 19 identifies GP900 antigen for Iowa isolate; and wherein said protein comprising 1721 amino acids depicted as SEQ ID NO: 6 or a protein depicted by SEQ ID NO: 20 identifies GP900 antigen for a NINC isolate.

22. The method of claim 21 wherein said detection of GP900, P68 and cryptopain species or isolates is used for diagnosis of Cryptosporidium infections in human or animal tissue samples.

23. A kit for detection of Cryptosporidium species or isolate in a biological or environmental sample consisting essentially of:

a means for contacting said sample with one of the following:

a recombinant Cryptosporidium GP900 antigen selected from a group consisting of a protein depicted by the SEQ ID NO: 5–20;

a recombinant P68 antigen selected from the group consisting of a protein depicted by the SEQ ID NO: 66; or a recombinant cryptopain antigen selected from the group consisting of a protein depicted by the SEQ ID NOs: 91–93, and 111–113;

for detection of a specific anti-Cryptosporidium GP900, anti-P68 or anti-cryptopain antibody; or an anti-Cryptosporidium GP900 antibody raised against a Cryptosporidium GP900 antigen selected from a group consisting of a protein depicted by the SEQ ID NO: 5–20 for detection of the GP900 antigen; or an anti-P68 antibody raised against a Cryptosporidium P68 antigen selected from a group consisting of a protein depicted by the SEQ ID NO: 66; or an anti-cryptopain antibody raised against a cryptopain antigen selected from a group consisting of a protein depicted by the SEQ ID NO: 91–93 and 111–113;

for detection of a presence of a Cryptosporidium GP900, P68 or cryptopain antigen; and a means for detection of a reaction between the antigen and antibody.

24. The kit of claim 23 wherein the means for contacting the sample is the antigen and said antigen is used to detect the presence of the anti-GP900, anti-P68 or anti-cryptopain antibody or wherein the means for contacting sample is the anti-Cryptosporidium antibody and said antibody is used to detect the presence of the antigen.

25. The kit of claim 24 wherein the antibody is the anti-GP900 antibody identified as M2, M10, M15, M24, E6, 7B3 or 10C6.

26. The kit of claim 23 wherein the antibody is polyclonal.

27. The kit of claim 23 wherein said means for contacting the sample is a set of primers for PCR amplification.

28. The kit of claim 27 wherein the primers for amplification are portions of GP900, P68 or cryptopain genomic DNA depicted by oligonucleotide sequence for detection of GP900 selected from the group depicted by SEQ ID NOs: 21–63, oligonucleotide sequence for detection of P68 selected from the group depicted by SEQ ID NOs: 67–87, and oligonucleotide sequence for detection of cryptopain selected from the group depicted by SEQ ID NOs 95–110.

29. A kit for detection of Cryptosporidium in a biological or environmental sample consisting essentially of:

a means for contacting said sample with an oligonucleotide probe for hybridization detection of a nucleotide sequence depicted by ID SEQ NOs: 1–4, 64, 65, 88–90, 94 and 114; or a set of primers for polymerase chain reaction (PCR) amplification and detection of a nucleotide sequence depicted ID SEQ NOs: 1–4, 64, 65, 88–90, 94 and 114 of Cryptosporidium GP900, P68 or cryptopain DNA or RNA; and a means for detection of a reaction between the probe and the nucleotide sequence for detection of DNA or RNA or for detection of amplified PCR product.

30. The kit of claim 29 wherein said means for contacting the sample is the oligonucleotide probe for hybridization with DNA or RNA, wherein said probe comprises oligonucleotide sequences complementary to Cryptosporidium GP900, P68 or cryptopain DNA or RNA.

31. A PCR primer for amplification of GP900, P68 or cryptopain DNA or RNA comprising an oligonucleotide sequence of about 14 to about 35 bp of the genomic DNA sequence of Cryptosporidium GP900, P68 or cryptopain DNA depicted by SEQ ID NOs: 1–4, 25 or 88–90.

32. The primer of claim 28 selected from the group consisting of a nucleotide sequence depicted by SEQ ID Nos: 21–63, 69–89, and 97–112.

33. The primer of claim 31 having a sense orientation and comprising an oligonucleotide sequence flanking a 5' region of a DNA sequence to be amplified.

34. The primer of claim 31 having an anti-sense orientation and comprising an oligonucleotide sequence flanking a 3' region of a DNA sequence to be amplified.

* * * * *

SEQUENCE LISTING

<160> NUMBER OF SEQ ID NOS: 115

<210> SEQ ID NO 1
<211> LENGTH: 7334
<212> TYPE: DNA
<213> ORGANISM: Cryptosporidium parvum

<400> SEQUENCE: 1

```
gatcctgcaa tgtggcaaat ggttacaact atagcagcaa tttgtagtac tgcatgccag      60
aatggtggta gaagtagtag acattgctgt agaaaacatc attctagaaa gcataaaaaa     120
gaagcagaat taaaagatac taatagcaat agcagtaaca aggaatcgag cgaccttagt     180
gaagctcaaa tagaccaaac tcccaaagaa agttccaacg acaagaacaa aaaatcaggc     240
gaaaggaagt caaaccaaaa tgataatact gttagtggaa ctaagtggca tggaatagaa     300
aaaaaaattg ctacaattag aggattgaga gacctagaaa gcactgattc gaaccttgat     360
gatgacgatg aattagctgc atctaataca ttgccacaag aataggaca tccaagatac     420 tctgatatgg tcgaatttcc gagcgaaatt tcagcattta atggtaattc aaggaataga     480
agatatttag caaaacaggg agtctgttat ggagcaaagt tttcaaagag cccatttgta     540
ggtggacttt ctgcagcaag gagaagacca tatagttgtc tcaccgaaat ggctgcctat     600 tttttctaaca ttgagcctca agaccaaaat gacgttattg ttatgcttct agcatgcaga    660
aagcttgaaa aacaaataga ggagcaacag actgtaatgc aactttttaga acatgaccta   720 aaagaagcgc agtctttatt gaggtttccc ccagaatgga ggtctcttaa taatgaagaa    780
gtattgggac attctccact tcctactgga caaattccat caaccaacga tcctccatac    840
gtctcaaacc atcccaatat tgaaccacct tgggttaaca aaagacctaa ggatggacta    900
ccttcaaggg cacctacaaa attatagatt atcaagcttt tcatagtagg ttcgaaaaaa    960
catatacttt agttcaattt aatagttaat ctcttgcatt tcgtaattaa acataatatc   1020
tattctctta gagagataca attattcata ttatttattt tatttctatt aaactctatc   1080
gaacacaaaa atataagaca tgtaagaacc gcaacactta gatctatacc acatcccccc   1140
ccaaaaactg cactagccgg taatcgaaac cgggccgacg caatgggaac gcgtcatcct   1200
accactagac tactagtgct aactgtctct cacctgtcta aattaattaa ttaattaatt   1260
aaggcggcaa aagccaatca cgcaataata acgtttttgc catttcccgc ctaaatgtgt   1320
gaggtgattt cttatgtaaa aaatgacgta tctttcaagt ctagcccgta ttgcaccccta  1380 atacatgcaa aggataatta tacgttgctg tacgcgagtg tatactctgt gaataaaaag   1440
tacatacatt agaaaatcct ggatagaaca gagaagcata ttgtgcattt tgaatgcact   1500
tgtgataact cttgttggca agtagttttt ttgtaatata ttaacgctac atcataagtt   1560
```

```
tcagcttagg aagttctttt gcacaggggtt tgagctagcc tactctagtg ataaacaaag   1620
ggtggcttgc tattgacaat tatcagagcc aaaaattata aattctaggt gaagtcaaaa   1680
atcatggtga acattaaagt gagctcatcg gcaatagccc ttgtggctgt tattatgaac   1740
ccactttttt cacttgcatt taaatcgagt aaccgattag agatgagaat tgaatcatct   1800
ggtgcagttt caaatgaaaa atttgtaatc ccatctctcc cttcagattt agacccaaca   1860
actttcttgc ttattgattc tactggcaag aaattcagtc catatactgg taaacatgct   1920
gatgcatcaa caacatctag tgcttacagt gcaccatttg agttggatgt tagcggagtt   1980
ccaatcgaac caaatacaag aagaatggtt gacccagttt ctttaatgct ttttgataat   2040
agcactggcg taatgtacga tccaaacacg aattctattt tggaaggttc aattgcaggt   2100
attagaagcg aatcttgcat tgtatctgaa ctgaactttt catctactac tggatttaca   2160
acggacacat caatgaattg gccggtaagt atcacaagtg gtgaactgaa ggatccaaac   2220
aaacaagcta ctatttctgg ttcaagatct tgtggatgga acaaggttta tagcattgat   2280
tcatccaccg ggtttagagt tgattctatc actggtctcc caactgatcc atacccctaat  2340 tgtccattca accctgtcac tggaaattta gtcagtaggt ccactggtaa aactattcca   2400
aacacttatg caggtgttta tcgttctaat gagactaaga ccactgagcc tagtgcaaac   2460
accaacttct tgttggtaga tcctaagatt aatgctcctt gtaattctga gaactctttt   2520
gaacaagtcc aaatatttga tatgggcagt aaggtataca ttccatacac taaatgtgtt   2580
ggagtgaaac acaacaacaa caacaacaaca actactacta ctactactac gacaacaaca   2640
acaacaacga caacaacaac aactactaca actactacca ctactactac gacaacaaca   2700
actactacta cgacaacaac aacaacaact actactacta ctacaaccac aacaactaca   2760
accacgacaa ctacaaccac aaccacaact accaagaaac caacaacaac aacaacaaca   2820
acaactacta ctactacaac aacaacaaca acaactacta ctactactac tactactact   2880
actactacta ctactactac cacaacaacc acaaccacaa ccacaactac caagaaacca   2940
acaacaacaa caacaacaac aacaacaact actactacaa ccacgacaac aacaaccacg   3000
acaaccacaa ccacaactac aactaccaag aaaccaacaa ctactactac tactaccaca   3060
acaacaacaa ctactactac taccacaaca acaacaacta ctactactac tacaaccaca   3120
accacaacca caaccgcaac cacaactacc aagaaaccaa caacaacaac aacaactact   3180
actactacta caaccaagaa accaacaaca actaccactg ccacaacaac aactactact   3240
tctgaaactg agagtgtaat taaacctgat gaatggtgtt ggttggaaaa gaatggcgaa   3300
tgtgaggcaa aaggagcaac ttatgttggt gttatcggaa aagatggacg tattgaaaat   3360
ggaatggcat ttacaatgat tccaaatgat gacacgcatg tccgtttcag atttaaggtt   3420
aaagatgtag ggaacactat ttcagtaaga tgcggaaaag gtgcaggtaa actcgagttc   3480
ccagatagaa gtttggattt cacaattcct ccagtagctg gccataacag ctgttcaata   3540
atagttggtg tgagcggcgg tggaaaaatt cacgtaagcc catacggttc taaggatgtc   3600
tctctaataa gtgctccaat acaaccttgt gagttattca atgaagttta ttgcgacact   3660
tgtactgcga agtatggtgc aattcactct ggatatcaaa cttcagctga tttcgtaaca   3720
acgactaccg caaaccaac aactactaca actggagccc aggacaacc aacaactact   3780 acaactggaa gtccaagcaa accaactact actaccacta ctaaggcaac aacaaccaca   3840
acaattctta atccaatcat tacaacaaca actcaaaaac caacaacaac aacaacaaca   3900
```

-continued

| | | | | |
|---|---|---|---|---|
| aaggttccag | gtaagccacc | aatagccaca | acaacaacaa | cattaaagcc aatagttaca | 3960 |
| acaacaacaa | caaaagcaac | aacaacaaca | acaacaacag | tgccaacgac aactactact | 4020 |
| accaagagag | acgaaatgac | aacaacaacg | acaccattac | ctgatatcgg tgacattgaa | 4080 |
| attacaccaa | tcccaattga | aaagatgttg | gataagtaca | caagaatgat ttatgactat | 4140 |
| aacagtggtt | tattattaga | ctctaatgat | gaaccaattc | caggttctca agcaggacaa | 4200 |
| atagctgata | caagcaattt | attcccagtt | caaactcaca | agagtactgg tttaccaatt | 4260 |
| gatccaatgg | ttggtcttcc | atttgatcca | aaatcaggta | atttagtaca tccatatacc | 4320 |
| aatcaaacaa | tgtctggttt | atcggtatca | tatcttgctg | ctaagaatt gacagttgat | 4380 |
| actgatgaaa | cctacggttt | accaattgat | acactcactg | ttacccatt ggatccagtc | 4440 |
| agtttgattc | cgttcaatcc | agaaactggt | gaattgtttg | atccaatatc agatgagata | 4500 |
| atgaatggaa | caattgcagg | tattgtttca | ggaatttctg | caagtgagtc attattatct | 4560 |
| cagaaatcag | ctccaatcga | cccagcaaca | aatatggttg | ttggagaatt tggtggattg | 4620 |
| ttgaacccag | caacaggagt | gatgattcca | ggttctttag | gtccatcaga gcaaactcca | 4680 |
| ttctcccctg | agattgaaga | tggtggtatt | attcctccag | aagtagcagc agcaaatgct | 4740 |
| gataaattca | agttatctat | tcctccaagc | gtaccagaat | caattccaga aaaggatcag | 4800 |
| aagattgatt | ctatttctga | attgatgtat | gatattgagt | caggtagact tattggtcaa | 4860 |
| gtatcaaaga | gaccaatccc | aggttcaatt | gctggtgact | gaacccaat aatgaagaca | 4920 |
| ccaacacaaa | ctgacagtgt | aactggtaaa | ccaatcgatc | caaccacagg tctgcctttc | 4980 |
| aatccaccaa | ctggtcattt | gattaaccca | acaaataata | ataccatgga ttcttcattt | 5040 |
| gctggtgcat | acaaatatgc | agtttcaaat | ggtattaaga | ctgataatgt ttatggttta | 5100 |
| ccagttgatg | aaataacagg | tttaccaaag | gatccagtgt | cagatattcc atttaactca | 5160 |
| actacaggtg | aattagttga | tccatcaaca | ggaaagccaa | ttaacaatta tactgctggt | 5220 |
| attgttagtg | gaaaacgtgg | cttaccacct | attgaagatg | aaaatggtaa tttgtttgat | 5280 |
| ccatcaacta | aattgccaat | agatggtaat | aaccaattag | ttaacccaga accaacagc | 5340 |
| actgtttcag | gatcaacttc | aggtagtaca | aaaccaaaac | caggaattcc agtcaatggt | 5400 |
| ggaggtgttg | tacctgatga | agaagctaaa | gatcaagccg | ataagggtaa ggatggatta | 5460 |
| attgttccac | caactaattc | tatcaataaa | gatccagtaa | caaatactca gtacagtaat | 5520 |
| actactggta | acattattaa | cccagaaaca | ggaaaagtta | ttccaggttc acttccaggc | 5580 |
| tctctcaact | atccatcatt | caatactcca | caacaaactg | atgagattac aggaaagcca | 5640 |
| gttgatactg | ttactggttt | gccatatgat | ccatctacag | tgaaattat cgatcctgca | 5700 |
| actaaattac | caattccagg | atcagttgca | ggtgatgaaa | tcctcactga agtattgaac | 5760 |
| attacaacag | atgaagtaac | aggtttgccg | attgatcttg | aaactggtct tccaagagat | 5820 |
| ccagtatcag | gactcccaca | acttccaaat | ggtaccttgg | ttgatccatc aaataaaaaa | 5880 |
| ccaattccag | gttcacattc | cggatttatt | aatggtacat | ctggagaaca atcacatgag | 5940 |
| aaagatccaa | gtactggtaa | gccacttgat | ccaaatacag | gtttgccatt cgatgaagat | 6000 |
| tctggtagtt | taattaaccc | agagactgga | gataaacttc | aaggatcaca ttctggtaca | 6060 |
| tttatgccag | taccaggtaa | accacaaggt | gaaaatggag | gtatcatgac acctgagcag | 6120 |
| atattggaag | cattaaataa | attgccaaca | agtaatgaag | taaatatttc accaagacca | 6180 |
| agttcagatg | ctgttccaga | tagaccaaca | aatacttggt | ggaataagat ttctggtcaa | 6240 |
| accttccagg | ttgatggaaa | gaagactatt | ccaggttctg | cagcttcagt aattcacact | 6300 |

```
gctcttggaa caccaactca aactgatcca acaacaggac ttccatctga tccatcaaca   6360
ggtttaccat tcattccagg atttaacgtg cttgtagatc ctcagactgg agagcaaatc   6420
aagggttctg ttccttatgt ttcattgtac gttaaggaaa agaatattgt aacagaagct   6480
gcttatggtc taccagttga tccaaagact ggtttcccaa ttgatccaat tagttacctc   6540
ccgtttgcta agaatggcga actaattgat cctatctctg gtaaatattt cagtggttca   6600
attgctggat tcatttctgg taaagctggt tcacaatcta aatcatctga tgaatcaggt   6660
aatccaattg atccatcaac aaatatgcct tacgatccaa aaacaggcaa attaattgat   6720
ccagaatctg gcattgctat tgataattct gtttcaggtg tgtttgcaac tgtacctggt   6780
actgctgcac cgaaaaaggg tggtgtcatt ccggagtcag ttgcagctga ggcagcaaag   6840
aaatactttg cagccaatgt tgagggagag ggagaaggag aagaagttcc accaccgcca   6900
gaatcatcta gtaacattgc aatccaagct gctggtggtc cttctgctgc tgtaggtctc   6960
gtagctgctg ttggtgcatg gtatgcaagc agaaacagac aggaaggaga agatgatgat   7020
gactatcaga tggatttgaa gcagaatatg aagaagaaga ggaagaagag ggtgatgaag   7080
cagcaaatga aactgttgtt acaattgagc gtgattcatc attctggaac gaatcttaaa   7140
cgtagaaaag atttttccaa ttcaaaaaaa tttcgaatat gaaaattaat gatttcctaa   7200
tatcaaatat tactacattt ctacatttcc tattgaaata tacgatttac taacatattg   7260
ctaattaata aatgattaat aatgacaaaa ttcaacgata tgatgaatct atcaaagcgt   7320
ttcaaatgga gaaa                                                     7334

<210> SEQ ID NO 2
<211> LENGTH: 5511
<212> TYPE: DNA
<213> ORGANISM: Cryptosporidium parvum

<400> SEQUENCE: 2
gtgaagtcaa aaatcatggt gaacattaaa gtgagctcat cggcaatagc ccttgtggct     60
gttattatga acccactttt ttcacttgca tttaaatcga gtaaccgatt agagatgaga    120
attgaatcat ctggtgcagt ttcaaatgaa aaatttgtaa tcccatctct cccttcagat    180
ttagacccaa caactttctt gcttattgat tctactggca agaaattcag tccatatact    240
ggtaaacatg ctgatgcatc aacaacatct agtgcttaca gtgcaccatt tgagttggat    300
gttagcggag ttccaatcga accaaataca agaagaatgg ttgacccagt ttctttaatg    360 cttttttgata atagcactgg cgtaatgtac gatccaaaca cgaattctat tttggaaggt    420
tcaattgcag gtattagaag cgaatcttgc attgtatctg aactgaactt tacatctact    480
actggattta caacggacac atcaatgaat tggccggtaa gtatcacaag tggtgaactg    540
aaggatccaa acaaacaagc tactatttct ggttcaagat cttgtggatg gaaacaaggt    600
tatagcattg attcatccac cgggtttaga gttgattcta tcactggtct cccaactgat    660 ccataccceta attgtccatt caaccctgtc actggaaatt tagtcagtag gtccactggt    720
aaaactattc caaacactta tgcaggtgtt tatcgttcta atgagactaa gaccactgag    780
cctagtgcaa acaccaactt cttgttggta gatcctaaga ttaatgctcc ttgtaattct    840
gagaactctt ttgaacaagt ccaaatattt gatatgggca gtaaggtata cattccatac    900
actaaatgtg ttggagtgaa acacacaaca acaacaacaa caactactac tactactact    960
acgacaacaa caacaacaac gacaacaaca acaactacta caactactac cactactact   1020
```

-continued

```
acgacaacaa caactactac tacgacaaca acaacaacaa ctactactac tactacaacc    1080
acaacaacta caaccacgac aactacaacc acaaccacaa ctaccaagaa accaacaaca    1140
acaacaacaa caacaactac tactactaca acaacaacaa caacaactac tactactact    1200
actactacta ctactactac tactactact accacaacaa ccacaaccac aaccacaact    1260
accaagaaac caacaacaac aacaacaaca acaacaacaa ctactactac aaccacgaca    1320
acaacaacca cgacaaccac aaccacaact acaactacca agaaaccaac aactactact    1380
actactacca caacaacaac aactactact actaccacaa caacaacaac tactactact    1440
actacaacca caaccacaac cacaaccgca accacaacta ccaagaaacc aacaacaaca    1500
acaacaacta ctactactac tacaaccaag aaaccaacaa caactaccac tgccacaaca    1560
acaactacta cttctgaaac tgagagtgta attaaacctg atgaatggtg ttggttggaa    1620
aagaatggcg aatgtgaggc aaaaggagca acttatgttg gtgttatcgg aaaagatgga    1680
cgtattgaaa atggaatggc atttacaatg attccaaatg atgacacgca tgtccgtttc    1740
agatttaagg ttaaagatgt agggaacact atttcagtaa gatgcggaaa aggtgcaggt    1800
aaactcgagt tcccagatag aagtttggat ttcacaattc ctccagtagc tggccataac    1860
agctgttcaa taatagttgg tgtgagcggc ggtggaaaaa ttcacgtaag cccatacggt    1920
tctaaggatg tctctctaat aagtgctcca atacaacctt gtgagttatt caatgaagtt    1980
tattgcgaca cttgtactgc gaagtatggt gcaattcact ctggatatca aacttcagct    2040
gatttcgtaa caacgactac cgcaaaacca acaactacta caactggagc cccaggacaa    2100
ccaacaacta ctacaactgg aagtccaagc aaaccaacta ctactaccac tactaaggca    2160
acaacaacca caacaattct taatccaatc attacaacaa caactcaaaa accaacaaca    2220
acaacaacaa caaaggttcc aggtaagcca ccaatagcca caacaacaac aacattaaag    2280
ccaatagtta caacaacaac aacaaaagca acaacaacaa caacaacaac agtgccaacg    2340
acaactacta ctaccaagag agacgaaatg acaacaacaa cgacaccatt acctgatatc    2400
ggtgacattg aaattacacc aatcccaatt gaaaagatgt tggataagta cacaagaatg    2460
atttatgact ataacagtgg tttattatta gactctaatg atgaaccaat tccaggttct    2520
caagcaggac aaatagctga tacaagcaat ttattcccag ttcaaactca caagagtact    2580
ggtttaccaa ttgatccaat ggttggtctt ccatttgatc caaaatcagg taatttagta    2640
catccatata ccaatcaaac aatgtctggt ttatcggtat catatcttgc tgctaagaat    2700
ttgacagttg atactgatga aacctacggt ttaccaattg atacactcac tggttaccca    2760
ttggatccag tcagtttgat tccgttcaat ccagaaactg tgaattgtt tgatccaata    2820 tcagatgaga taatgaatgg aacaattgca ggtattgttt caggaatttc tgcaagtgag    2880
tcattattat ctcagaaatc agctccaatc gacccagcaa caaatatggt tgttggagaa    2940
tttggtggat tgttgaaccc agcaacagga gtgatgattc caggttcttt aggtccatca    3000
gagcaaactc cattctcccc tgagattgaa gatggtggta ttattcctcc agaagtagca    3060
gcagcaaatg ctgataaatt caagttatct attcctccaa gcgtaccaga atcaattcca    3120
gaaaaggatc agaagattga ttctatttct gaattgatgt atgatattga gtcaggtaga    3180
cttattggtc aagtatcaaa gagaccaatc ccaggttcaa ttgctggtga cttgaaccca    3240
ataatgaaga caccaacaca aactgacagt gtaactggta aaccaatcga tccaaccaca    3300
ggtctgcctt tcaatccacc aactggtcat ttgattaacc caacaaataa taataccatg    3360
gattcttcat tgctggtgc atacaaatat gcagtttcaa atggtattaa gactgataat    3420
```

| | |
|---|---|
| gtttatggtt taccagttga tgaaataaca ggtttaccaa aggatccagt gtcagatatt | 3480 |
| ccatttaact caactacagg tgaattagtt gatccatcaa caggaaagcc aattaacaat | 3540 |
| tatactgctg gtattgttag tggaaaacgt ggcttaccac ctattgaaga tgaaaatggt | 3600 |
| aatttgtttg atccatcaac taaattgcca atagatggta ataaccaatt agttaaccca | 3660 |
| gaaaccaaca gcactgtttc aggatcaact tcaggtagta caaaaccaaa accaggaatt | 3720 |
| ccagtcaatg gtggaggtgt tgtacctgat gaagaagcta agatcaagc cgataagggt | 3780 |
| aaggatggat taattgttcc accaactaat tctatcaata aagatccagt aacaaatact | 3840 |
| cagtacagta atactactgg taacattatt aacccagaaa caggaaaagt tattccaggt | 3900 |
| tcacttccag gctctctcaa ctatccatca ttcaatactc cacaacaaac tgatgagatt | 3960 |
| acaggaaagc cagttgatac tgttactggt ttgccatatg atccatctac aggtgaaatt | 4020 |
| atcgatcctg caactaaatt accaattcca ggatcagttg caggtgatga atcctcact | 4080 |
| gaagtattga acattacaac agatgaagta acaggtttgc cgattgatct tgaaactggt | 4140 |
| cttccaagag atccagtatc aggactccca caacttccaa atggtacctt ggttgatcca | 4200 |
| tcaaataaaa aaccaattcc aggttcacat tccggattta ttaatggtac atctggagaa | 4260 |
| caatcacatg agaaagatcc aagtactggt aagccacttg atccaaatac aggtttgcca | 4320 |
| ttcgatgaag attctggtag tttaattaac ccagagactg gagataaact tcaaggatca | 4380 |
| cattctggta catttatgcc agtaccaggt aaaccacaag gtgaaaatgg aggtatcatg | 4440 |
| acacctgagc agatattgga agcattaaat aaattgccaa caagtaatga agtaaatatt | 4500 |
| tcaccaagac caagttcaga tgctgttcca gatagaccaa caaatacttg gtggaataag | 4560 |
| atttctggtc aaaccttcca ggttgatgga agaagactta ttcaggttc tgcagcttca | 4620 |
| gtaattcaca ctgctcttgg aacaccaact caaactgatc caacaacagg acttccatct | 4680 |
| gatccatcaa caggtttacc attcattcca ggatttaacg tgcttgtaga tcctcagact | 4740 |
| ggagagcaaa tcaagggttc tgttccttat gtttcattgt acgttaagga aaagaatatt | 4800 |
| gtaacagaag ctgcttatgg tctaccagtt gatccaaaga ctggtttccc aattgatcca | 4860 |
| attagttacc tcccgtttgc taagaatggc gaactaattg atcctatctc tggtaaaatat | 4920 |
| ttcagtggtt caattgctgg attcatttct ggtaaagctg gttcacaatc taaatcatct | 4980 |
| gatgaatcag gtaatccaat tgatccatca acaaatatgc cttacgatcc aaaaacaggc | 5040 |
| aaattaattg atccagaatc tggcattgct attgataatt ctgtttcagg tgtgtttgca | 5100 |
| actgtacctg gtactgctgc accgaaaaag ggtggtgtca ttccggagtc agttgcagct | 5160 |
| gaggcagcaa agaaatactt tgcagccaat gttgaggag agggagaagg agaagaagtt | 5220 |
| ccaccaccgc cagaatcatc tagtaacatt gcaatccaag ctgctggtgg tgcttctgct | 5280 |
| gctgtaggtc tcgtagctgc tgttggtgca tggtatgcaa gcagaaacag acaggaagga | 5340 |
| gaagatgatg atgactatca gatggatttg aagcagaata tgaagaagaa gaggaagaag | 5400 |
| agggtgatga agcagcaaat gaaactgttg ttacaattga gcgtgattca tcattctgga | 5460 |
| acgaatctta aacgtagaaa agatttttcc aattcaaaaa aatttcgaat a | 5511 |

<210> SEQ ID NO 3
<211> LENGTH: 5318
<212> TYPE: DNA
<213> ORGANISM: Cryptosporidium parvum

<400> SEQUENCE: 3

-continued

| | | | | |
|---|---|---|---|---|
| attttggaag | gttcaattgc | aggtattaga | agcgaatctt | gcattgtatc | tgaactgaac | 60 |
| tttacatcta | ctactggatt | tacaacggac | acatcaatga | attggccggt | aagtatcaca | 120 |
| agtggtgaac | tgaaggatcc | aaacaaacaa | gctactattt | ctggttcaag | atcttgtgga | 180 |
| tggaaacaag | gttatagcat | tgattcatcc | accgggttta | gagttgattc | tatcactggt | 240 |
| ctcccaactg | atccatactc | taattgtcca | ttcaaccctg | tcactggaaa | tttagtcagt | 300 |
| aggtccactg | gtaaaactat | tccaaacact | tatgcaggtg | tttatcgttc | taatgagact | 360 |
| aagaccactg | agcctagtgc | aaacacttat | gcaggtgttt | atcgttctaa | tgagactaag | 420 |
| accactgagc | ctagtgcaaa | caccaacttc | ttgttggtag | atcctaagat | taatgctcct | 480 |
| tgtaattctg | agaactcttt | tgaacaaggt | caaatatttg | atatgggcag | taaggtatac | 540 |
| attccataca | ctaaatgtgt | tggagtgaaa | cacacaacaa | caacaacaac | aactactact | 600 |
| actactacta | cgacaacaac | aacaacaacg | acaacaacaa | caactactac | aactactacc | 660 |
| actactacta | cgacaacaac | aacaacaaca | acaacaacaa | caacaacaac | aacaacaaca | 720 |
| acaacaacaa | caacgactac | tactactact | actactacta | ctactactac | tactactaca | 780 |
| accacaacaa | ctacaaccac | aactacaacc | acaacaacta | caaccacaac | aacaacaacc | 840 |
| acaacaacta | caaccacaac | tacaaccaca | acaactacaa | ccacaacaac | cacaaccaca | 900 |
| accacaacta | ccaagaaacc | aacaacaaca | actacaacaa | caacaacaac | aacaacaact | 960 |
| actactacaa | ccaccacaac | aacaacaaca | acaacaacta | caactaccaa | gaaaccaaca | 1020 |
| actactacta | ctactaccac | aacaacaaca | actactacta | ctaccacaac | aacaacaact | 1080 |
| actactacta | ctacaacaac | aacaacaaca | acaacaacaa | caacaactac | cacgaaacca | 1140 |
| acaacaacaa | caacaactac | tactactact | acaaccaaga | aaccaacaac | aactaccact | 1200 |
| gccacaacaa | caactactac | ttctgaaact | gagagtgtaa | ttaaacctga | tgaatggtgt | 1260 |
| tggttggaaa | agaatggcga | atgtgaggca | aaggagcaa | cttatgttgg | tgttatcgga | 1320 |
| aaagatggac | gtattgaaaa | tggaatggca | tttacaatga | ttccaaatga | tgacacgcat | 1380 |
| gtccgcttca | gatttaaggt | taagatgta | gggaacacta | tttcagtaag | atgcagaaaa | 1440 |
| ggtgcaggta | aactcgagtt | cccagataga | agtttggatt | tcacaattcc | tccagtagct | 1500 |
| ggccataaca | gctgttcaat | aatagttggt | gtgagcggcg | atggaaaaat | tcacgtaagc | 1560 |
| ccatacggtt | ctaaggatgt | ctctctaata | agtgctccaa | tacaaccttc | tgagttattc | 1620 |
| aatgaagttt | attgcgacac | ttgtactgcg | aagtatggtg | caattcactc | tggatatcaa | 1680 |
| acttcagctg | atttcgtaac | aacgactacc | gcaaaaccaa | caactactac | aactggagcc | 1740 |
| ccaggacaac | caacaactac | tacaactgga | agtccaagca | aaccaactac | tactaccact | 1800 |
| actaaggcaa | caacaaccac | aacaactctt | aatccaatca | ttacaacaac | aactcaaaaa | 1860 |
| ccaacaacaa | caacaacaac | aaaggttcca | ggtaagccac | aatagccac | aacaacaaca | 1920 |
| acattaaagc | caatagttac | aacaacaaca | acaaaagcaa | caacaacaac | aacaacaaca | 1980 |
| gtgccaacga | caactactac | taccaagaga | gacgaaatga | caacaacaac | gacaccatta | 2040 |
| cctgatatcg | gtgacattga | aattacacca | atcccaattg | aaaagatgtt | ggataagtac | 2100 |
| acaagaatga | tttatgacta | taacagtggt | ttattattag | actctaatga | tgaaccaatt | 2160 |
| ccaggttctc | aagcaggaca | aatagctgat | acaagcaatt | tattcccagt | tcaaactcac | 2220 |
| aagagtactg | gtttaccaat | tgatccaatg | gttggtcttc | catttgatcc | aaaatcaggt | 2280 |
| aatttagtac | atccatatac | caatcaaaca | atgtctggtt | tatcggtatc | atatcttgct | 2340 |
| gctaagaatt | tgacagttga | tactgatgaa | acctacggtt | taccaattga | tacactcact | 2400 |

```
ggttacccat tggatccagt cagtttgatt ccgttcaatc cagaaactgg tgaattgttt      2460
gatccaatat cagatgagat aatgaatgga acaattgcag gtattgtttc aggaatttct      2520
gcaagtgagt cattattatc tcagaaatca gctctaatcg acccagcaac aaatatggtt      2580
gttggagaat tggtggatt gttgaaccca gcaacaggag tgatgattcc aggtttttta      2640
ggtccatcag agcaaactca attctcccct gagattaag atggtggtat tattcctcca      2700
gaagtagcag cagcaaatgc tgataaattc aagttatcta ttcctccaag cgtaccagaa      2760
tcaattccag aaaaggatca aagattgat tctatttctg aattgatgta tgatattgag      2820
tcaggtagac ttattggtca agtatcaaag agaccaatcc caggttcaat tgctggtgac      2880
ttgaacccaa taatgaagac accaacacaa actgacagtg taactggtaa accaatcgat      2940
ccaaccacag gtctgccttt caatccacca actggtcatt tgattaaccc aacaaataat      3000
aataccatgg attcttcatt tgctggtgca tacaaatatg cagtttcaaa tggtattaag      3060
actgataatg tttatggttt accagttggt gaaataacag gtttaccaaa ggatccaggc      3120
tcagatattc catttaactc aactacaggt gaattagttg atccatcaac aggaaagcca      3180
attaacaatt ctactgctgg tattgttagt ggaaaacctg gcttaccacc tattgaagat      3240
gaaaatggta atttgtttga tccatcaact aacttgccaa tagatggtaa taccaatta      3300 gttaacccag aaaccaacag cactgtctca ggatcaactt caggtactac aaaaccaaaa      3360
ccaggaattc cagtcaatgg tggaggtgtt gtacctgatg aagaagctaa agatcaagcc      3420
gataagggta aggatggatt aattgttcca ccaactaatt ctatcaataa agatccagta      3480
acaaatactc agtacagtaa tactactggt aacattatta acccgaaaac aggaaaagtt      3540
attccaggtt cacttccagg ctctctcaac tatccatcat tcaatactcc acaacaaact      3600
gatgagatta caggaaagcc agttgatact gttactggtt tgccatatga tccatctaca      3660
ggtgaaatta tcgatcctgc aactaaatta ccaattccag gatcagttgc aggtgatgaa      3720
atcctcactg aagtattgaa cattacaaca gatgaagtaa caggtttgcc aattgatctt      3780
gaaactggtc ttccaagaga tccagtatca ggactccac aacttccaaa tggtaccttg      3840
gttgatccat caaataaaaa accaattcca ggttcacatt ccggatttat taatggtaca      3900
tctggagaac aatcacatga gaaagatcca agtactggta agccacttga tccaaataca      3960
ggtttgcacc cattcgatga agattcaggt agtttaatta acccagagac tggagataaa      4020
cttcaaggat cacattctgg tacatttatg ccagtaccag gtaaaccaca aggtgaaaat      4080
ggaggtatca tgacacctga gcagatattg gaagcattaa ataaattgcc aacaagtaat      4140
gaagtaaata tttcaccaag accaagttca gatgctgttc cagatagacc aacaaatact      4200
tggtggaata agattttctgg tcaaacctac caggttgatg gaaagaagac tattccaggt      4260
tctgcagctt cagtaattca cactgctctt ggaacaccaa ctcaaactga tccaacaaca      4320
ggacttccat ctgatccatc aacaggttta ccattcattc caggatttaa cgtgcttgta      4380
gatcctcaga ctggagagca aatcaagggt tctgttcctt atgtttcatt gtacgttaag      4440
gaaaagaata ttgtaacaga agctgcttat ggtctaccag ttgatccaaa gactggtttc      4500
ccaattgatc caattagtta cctcccgttt gctaagaatg cgaactaat tgatcctatc      4560 tctggtaaat atttcagtgg ttcaattgct ggattcattt ctggtaaagc tggttcacaa      4620
tctaaatcat ctgatgaatc aggtaatcca attgatccat caacaaatat gccttacgat      4680
ccaaaaggcg gcaaattaat tgatccagaa tctggcattg ctattgataa ttctgtttca      4740
```

| | |
|---|---:|
| ggtgtgtttg caactgtacc tggtactgct gcaccgaaaa agggtggtgt cattccggag | 4800 |
| tcagttgcag ctgaggcagc aaagaaatac tttgcagcca atgttgaggg agagggagaa | 4860 |
| ggagaagaag ttccaccacc gccagaatca tctagtaaca ttgcaatcca agctgctggt | 4920 |
| ggtgcttctg ctgctgtagg tctcgtagct gctgttggtg catggtatgc aagcagaaac | 4980 |
| agacaggaag gagaagatga tgatgactat cagatggatt tgaagcagaa tatgaagaag | 5040 |
| aagaggaaga agagggtgat gaagcagcaa atgaaactgt tgttacaatt gagcgtgatt | 5100 |
| catcattctg gaacgaatct taaacgtaga aaagattttt ccaattcaaa aaatttcga | 5160 |
| atatgaaaat taatgatttc ctaatatcaa atattactac atttctacat ttcctattga | 5220 |
| aatatacgat ttactaacat attgctaatt aataaatgat taataatgac aaaattcaac | 5280 |
| gatatgatga atctatcaaa gcgtttcaaa tggagaaa | 5318 |

<210> SEQ ID NO 4
<211> LENGTH: 5163
<212> TYPE: DNA
<213> ORGANISM: Cryptosporidium parvum

<400> SEQUENCE: 4

| | |
|---|---:|
| attttggaag gttcaattgc aggtattaga agcgaatctt gcattgtatc tgaactgaac | 60 |
| tttacatcta ctactggatt tacaacggac acatcaatga attggccggt aagtatcaca | 120 |
| agtggtgaac tgaaggatcc aaacaaacaa gctactattt ctggttcaag atcttgtgga | 180 |
| tggaaacaag gttatagcat tgattcatcc accgggttta gagttgattc tatcactggt | 240 |
| ctcccaactg atccatactc taattgtcca ttcaaccctg tcactggaaa tttagtcagt | 300 |
| aggtccactg gtaaaactat tccaaacact tatgcaggtg tttatcgttc taatgagact | 360 |
| aagaccactg agcctagtgc aaacacttat gcaggtgttt atcgttctaa tgagactaag | 420 |
| accactgagc ctagtgcaaa caccaacttc ttgttggtag atcctaagat taatgctcct | 480 |
| tgtaattctg agaactcttt tgaacaaggt caaatatttg atatgggcag taaggtatac | 540 |
| attccataca ctaaatgtgt tggagtgaaa cacacaacaa caacaacaac aactactact | 600 |
| actactacta cgacaacaac aacaacaacg acaacaacaa caactactac aactactacc | 660 |
| actactacta cgacaacaac aacaacaaca acaacaacaa caacaacaac aacaacaaca | 720 |
| acaacaacaa caacgactac tactactact actactacta ctactactac tactactaca | 780 |
| accacaacaa ctacaaccac aactacaacc acaacaacta caaccacaac aacaacaacc | 840 |
| acaacaacta caaccacaac tacaaccaca acaactacaa ccacaacaac cacaaccaca | 900 |
| accacaacta ccaagaaacc aacaacaaca actacaacaa caacaacaac aacaacaact | 960 |
| actactacaa ccaccacaac aacaacaaca acaacaacta caactaccaa gaaaccaaca | 1020 |
| actactacta ctactaccac aacaacaaca actactacta ctaccacaac aacaacaact | 1080 |
| actactacta ctacaacaac aacaacaaca acaacaacaa caacaactac cacgaaacca | 1140 |
| acaacaacaa caacaactac tactactact acaaccaaga aaccaacaac aactaccact | 1200 |
| gccacaacaa caactactac ttctgaaact gagagtgtaa ttaaacctga tgaatggtgt | 1260 |
| tggttggaaa agaatggcga atgtgaggca aaaggagcaa cttatgttgg tgttatcgga | 1320 |
| aaagatggac gtattgaaaa tggaatggca tttacaatga ttccaaatga tgacacgcat | 1380 |
| gtccgcttca gatttaaggt taaagatgta gggaacacta tttcagtaag atgcagaaaa | 1440 |
| ggtgcaggta aactcgagtt cccagataga agtttggatt tcacaattcc tccagtagct | 1500 |
| ggccataaca gctgttcaat aatagttggt gtgagcggcg atggaaaaat tcacgtaagc | 1560 |

```
ccatacggtt ctaaggatgt ctctctaata agtgctccaa tacaaccttc tgagttattc   1620
aatgaagttt attgcgacac ttgtactgcg aagtatggtg caattcactc tggatatcaa   1680
acttcagctg atttcgtaac aacgactacc gcaaaaccaa caactactac aactggagcc   1740
ccaggacaac caacaactac tacaactgga agtccaagca aaccaactac tactaccact   1800
actaaggcaa caacaaccac aacaactctt aatccaatca ttacaacaac aactcaaaaa   1860
ccaacaacaa caacaacaac aaaggttcca ggtaagccac caatagccac aacaacaaca   1920
acattaaagc caatagttac aacaacaaca acaaagcaa caacaacaac aacaacaaca    1980
gtgccaacga caactactac taccaagaga gacgaaatga caacaacaac gacaccatta   2040
cctgatatcg gtgacattga aattacacca atcccaattg aaaagatgtt ggataagtac   2100
acaagaatga tttatgacta taacagtggt ttattattag actctaatga tgaaccaatt   2160
ccaggttctc aagcaggaca aatagctgat acaagcaatt tattcccagt tcaaactcac   2220
aagagtactg gtttaccaat tgatccaatg gttggtcttc catttgatcc aaaatcaggt   2280
aatttagtac atccatatac caatcaaaca atgtctggtt tatcggtatc atatcttgct   2340
gctaagaatt tgacagttga tactgatgaa acctacggtt taccaattga tacactcact   2400
ggttacccat tggatccagt cagtttgatt ccgttcaatc cagaaactgg tgaattgttt   2460
gatccaatat cagatgagat aatgaatgga acaattgcag gtattgtttc aggaatttct   2520
gcaagtgagt cattattatc tcagaaatca gctctaatcg acccagcaac aaatatggtt   2580
gttggagaat tggtggatt gttgaaccca gcaacaggag tgatgattcc aggtttttta   2640
ggtccatcag agcaaactca attctcccct gagattgaag atggtggtat tattcctcca   2700
gaagtagcag cagcaaatgc tgataaattc aagttatcta ttcctccaag cgtaccagaa   2760
tcaattccag aaaaggatca gaagattgat tctatttctg aattgatgta tgatattgag   2820
tcaggtagac ttattggtca agtatcaaag agaccaatcc caggttcaat tgctggtgac   2880
ttgaacccaa taatgaagac accaacacaa actgacagtg taactggtaa accaatcgat   2940
ccaaccacag gtctgccttt caatccacca actggtcatt tgattaaccc aacaaataat   3000
aataccatgg attcttcatt tgctggtgca tacaaatatg cagtttcaaa tggtattaag   3060
actgataatg tttatggttt accagttggt gaaataacag gtttaccaaa ggatccaggc   3120
tcagatattc catttaactc aactacaggt gaattagttg atccatcaac aggaaagcca   3180
attaacaatt ctactgctgg tattgttagt ggaaaacctg gcttaccacc tattgaagat   3240
gaaaatggta atttgtttga tccatcaact aacttgccaa tagatggtaa taaccaatta   3300
gttaacccag aaaccaacag cactgtctca ggatcaactt caggtactac aaaaccaaaa   3360
ccaggaattc cagtcaatgg tggaggtgtt gtacctgatg aagaagctaa agatcaagcc   3420
gataagggta aggatggatt aattgttcca ccaactaatt ctatcaataa agatccagta   3480
acaaatactc agtacagtaa tactactggt aacattatta acccagaaac aggaaaagtt   3540
attccaggtt cacttccagg ctctctcaac tatccatcat tcaatactcc acaacaaact   3600
gatgagatta caggaaagcc agttgatact gttactggtt tgccatatga tccatctaca   3660
ggtgaaatta tcgatcctgc aactaaatta ccaattccag gatcagttgc aggtgatgaa   3720
atcctcactg aagtattgaa cattacaaca gatgaagtaa caggtttgcc aattgatctt   3780
gaaactggtc ttccaagaga tccagtatca ggactcccac aacttccaaa tggtaccttg   3840
gttgatccat caaataaaaa accaattcca ggttcacatt ccggattta taatggtaca   3900
```

```
tctggagaac aatcacatga gaaagatcca agtactggta agccacttga tccaaataca    3960
ggtttgcacc cattcgatga agattcaggt agtttaatta acccagagac tggagataaa    4020
cttcaaggat cacattctgg tacatttatg ccagtaccag gtaaaccaca aggtgaaaat    4080
ggaggtatca tgacacctga gcagatattg gaagcattaa ataaattgcc aacaagtaat    4140
gaagtaaata tttcaccaag accaagttca gatgctgttc cagatagacc aacaaatact    4200
tggtggaata agatttctgg tcaaacctac caggttgatg gaaagaagac tattccaggt    4260
tctgcagctt cagtaattca cactgctctt ggaacaccaa ctcaaactga tccaacaaca    4320
ggacttccat ctgatccatc aacaggttta ccattcattc aggatttaa cgtgcttgta    4380
gatcctcaga ctggagagca aatcaagggt tctgttcctt atgtttcatt gtacgttaag    4440
gaaaagaata ttgtaacaga agctgcttat ggtctaccag ttgatccaaa gactggtttc    4500
ccaattgatc caattagtta cctcccgttt gctaagaatg gcgaactaat tgatcctatc    4560
tctggtaaat atttcagtgg ttcaattgct ggattcattt ctggtaaagc tggttcacaa    4620
tctaaatcat ctgatgaatc aggtaatcca attgatccat caacaaatat gccttacgat    4680
ccaaaaggcg gcaaattaat tgatccagaa tctggcattg ctattgataa ttctgtttca    4740
ggtgtgtttg caactgtacc tggtactgct gcaccgaaaa agggtggtgt cattccggag    4800
tcagttgcag ctgaggcagc aaagaaatac tttgcagcca atgttgaggg agagggagaa    4860
ggagaagaag ttccaccacc gccagaatca tctagtaaca ttgcaatcca agctgctggt    4920
ggtgcttctg ctgctgtagg tctcgtagct gctgttggtg catggtatgc aagcagaaac    4980
agacaggaag gagaagatga tgatgactat cagatggatt tgaagcagaa atgaagaag    5040
aagaggaaga agagggtgat gaagcagcaa atgaaactgt tgttacaatt gagcgtgatt    5100
catcattctg gaacgaatct taaacgtaga aaagattttt ccaattcaaa aaatttcga    5160
ata                                                                  5163
```

<210> SEQ ID NO 5
<211> LENGTH: 1837
<212> TYPE: PRT
<213> ORGANISM: Cryptosporidium parvum

<400> SEQUENCE: 5

```
Val Lys Ser Lys Ile Met Val Asn Ile Lys Val Ser Ser Ser Ala Ile
  1               5                  10                  15

Ala Leu Val Ala Val Ile Met Asn Pro Leu Phe Ser Leu Ala Phe Lys
             20                  25                  30

Ser Ser Asn Arg Leu Glu Met Arg Ile Glu Ser Ser Gly Ala Val Ser
         35                  40                  45

Asn Glu Lys Phe Val Ile Pro Ser Leu Pro Ser Asp Leu Asp Pro Thr
     50                  55                  60

Thr Phe Leu Leu Ile Asp Ser Thr Gly Lys Lys Phe Ser Pro Tyr Thr
 65                  70                  75                  80

Gly Lys His Ala Asp Ala Ser Thr Thr Ser Ser Ala Tyr Ser Ala Pro
                 85                  90                  95

Phe Glu Leu Asp Val Ser Gly Val Pro Ile Glu Pro Asn Thr Arg Arg
            100                 105                 110

Met Val Asp Pro Val Ser Leu Met Leu Phe Asp Asn Ser Thr Gly Val
        115                 120                 125

Met Tyr Asp Pro Asn Thr Asn Ser Ile Leu Glu Gly Ser Ile Ala Gly
    130                 135                 140
```

-continued

```
Ile Arg Ser Glu Ser Cys Ile Val Ser Glu Leu Asn Phe Thr Ser Thr
145                 150                 155                 160

Thr Gly Phe Thr Thr Asp Thr Ser Met Asn Trp Pro Val Ser Ile Thr
                165                 170                 175

Ser Gly Glu Leu Lys Asp Pro Asn Lys Gln Ala Thr Ile Ser Gly Ser
            180                 185                 190

Arg Ser Cys Gly Trp Lys Gln Gly Tyr Ser Ile Asp Ser Ser Thr Gly
        195                 200                 205

Phe Arg Val Asp Ser Ile Thr Gly Leu Pro Thr Asp Pro Tyr Pro Asn
    210                 215                 220

Cys Pro Phe Asn Pro Val Thr Gly Asn Leu Val Ser Arg Ser Thr Gly
225                 230                 235                 240

Lys Thr Ile Pro Asn Thr Tyr Ala Gly Val Tyr Arg Ser Asn Glu Thr
                245                 250                 255

Lys Thr Thr Glu Pro Ser Ala Asn Thr Asn Phe Leu Leu Val Asp Pro
            260                 265                 270

Lys Ile Asn Ala Pro Cys Asn Ser Glu Asn Ser Phe Glu Gln Val Gln
        275                 280                 285

Ile Phe Asp Met Gly Ser Lys Val Tyr Ile Pro Tyr Thr Lys Cys Val
    290                 295                 300

Gly Val Lys His Thr Thr Thr Thr Thr Thr Thr Thr Thr Thr Thr Thr
305                 310                 315                 320

Thr Thr Thr Thr Thr Thr Thr Thr Thr Thr Thr Thr Thr Thr Thr Thr
                325                 330                 335

Thr Thr Thr Thr Thr Thr Thr Thr Thr Thr Thr Thr Thr Thr Thr Thr
            340                 345                 350

Thr Thr Thr Thr Thr Thr Thr Thr Thr Thr Thr Thr Thr Thr Thr Thr
        355                 360                 365

Thr Thr Thr Thr Thr Thr Lys Lys Pro Thr Thr Thr Thr Thr Thr Thr
    370                 375                 380

Thr Thr Thr Thr Thr Thr Thr Thr Thr Thr Thr Thr Thr Thr Thr Thr
385                 390                 395                 400

Thr Thr Thr Thr Thr Thr Thr Thr Thr Thr Thr Thr Thr Thr Thr Thr
                405                 410                 415

Thr Thr Thr Thr Lys Lys Pro Thr Thr Thr Thr Thr Thr Thr Thr Thr
            420                 425                 430

Thr Thr Thr Thr Thr Thr Thr Thr Thr Thr Thr Thr Thr Thr Thr Thr
        435                 440                 445

Thr Thr Thr Thr Lys Lys Pro Thr Thr Thr Thr Thr Thr Thr Thr Thr
    450                 455                 460

Thr Thr Thr Thr Thr Thr Thr Thr Thr Thr Thr Thr Thr Thr Thr Thr
465                 470                 475                 480

Thr Thr Thr Thr Thr Thr Thr Thr Ala Thr Thr Thr Thr Lys Lys
                485                 490                 495

Pro Thr Thr Thr Thr Thr Thr Thr Thr Thr Thr Thr Lys Lys Pro
            500                 505                 510

Thr Thr Thr Thr Thr Ala Thr Thr Thr Thr Thr Ser Glu Thr Glu
        515                 520                 525

Ser Val Ile Lys Pro Asp Glu Trp Cys Trp Leu Glu Lys Asn Gly Glu
    530                 535                 540

Cys Glu Ala Lys Gly Ala Thr Tyr Val Gly Val Ile Gly Lys Asp Gly
545                 550                 555                 560

Arg Ile Glu Asn Gly Met Ala Phe Thr Met Ile Pro Asn Asp Asp Thr
```

```
                      565                 570                 575
His Val Arg Phe Arg Phe Lys Val Lys Asp Val Gly Asn Thr Ile Ser
                580                 585                 590

Val Arg Cys Gly Lys Gly Ala Gly Lys Leu Glu Phe Pro Asp Arg Ser
            595                 600                 605

Leu Asp Phe Thr Ile Pro Pro Val Ala Gly His Asn Ser Cys Ser Ile
        610                 615                 620

Ile Val Gly Val Ser Gly Gly Lys Ile His Val Ser Pro Tyr Gly
625                 630                 635                 640

Ser Lys Asp Val Ser Leu Ile Ser Ala Pro Ile Gln Pro Cys Glu Leu
                645                 650                 655

Phe Asn Glu Val Tyr Cys Asp Thr Cys Thr Ala Lys Tyr Gly Ala Ile
            660                 665                 670

His Ser Gly Tyr Gln Thr Ser Ala Asp Phe Val Thr Thr Thr Ala
        675                 680                 685

Lys Pro Thr Thr Thr Thr Gly Ala Pro Gly Gln Pro Thr Thr Thr
        690                 695                 700

Thr Thr Gly Ser Pro Ser Lys Pro Thr Thr Thr Thr Thr Lys Ala
705                 710                 715                 720

Thr Thr Thr Thr Thr Ile Leu Asn Pro Ile Ile Thr Thr Thr Gln
                725                 730                 735

Lys Pro Thr Thr Thr Thr Thr Lys Val Pro Gly Lys Pro Pro Ile
            740                 745                 750

Ala Thr Thr Thr Thr Leu Lys Pro Ile Val Thr Thr Thr Thr
        755                 760                 765

Lys Ala Thr Thr Thr Thr Thr Thr Val Pro Thr Thr Thr Thr Thr
770                 775                 780

Thr Lys Arg Asp Glu Met Thr Thr Thr Thr Pro Leu Pro Asp Ile
785                 790                 795                 800

Gly Asp Ile Glu Ile Thr Pro Ile Pro Ile Glu Lys Met Leu Asp Lys
                805                 810                 815

Tyr Thr Arg Met Ile Tyr Asp Tyr Asn Ser Gly Leu Leu Leu Asp Ser
            820                 825                 830

Asn Asp Glu Pro Ile Pro Gly Ser Gln Ala Gly Gln Ile Ala Asp Thr
        835                 840                 845

Ser Asn Leu Phe Pro Val Gln Thr His Lys Ser Thr Gly Leu Pro Ile
850                 855                 860

Asp Pro Met Val Gly Leu Pro Phe Asp Pro Lys Ser Gly Asn Leu Val
865                 870                 875                 880

His Pro Tyr Thr Asn Gln Thr Met Ser Gly Leu Ser Val Ser Tyr Leu
                885                 890                 895

Ala Ala Lys Asn Leu Thr Val Asp Thr Asp Glu Thr Tyr Gly Leu Pro
            900                 905                 910

Ile Asp Thr Leu Thr Gly Tyr Pro Leu Asp Pro Val Ser Leu Ile Pro
        915                 920                 925

Phe Asn Pro Glu Thr Gly Glu Leu Phe Asp Pro Ile Ser Asp Glu Ile
    930                 935                 940

Met Asn Gly Thr Ile Ala Gly Ile Val Ser Gly Ile Ser Ala Ser Glu
945                 950                 955                 960

Ser Leu Leu Ser Gln Lys Ser Ala Pro Ile Asp Pro Ala Thr Asn Met
                965                 970                 975

Val Val Gly Glu Phe Gly Gly Leu Leu Asn Pro Ala Thr Gly Val Met
            980                 985                 990
```

-continued

```
Ile Pro Gly Ser Leu Gly Pro Ser Glu Gln Thr Pro Phe Ser Pro Glu
            995                 1000                1005
Ile Glu Asp Gly Gly Ile Ile Pro Pro Glu Val Ala Ala Ala Asn Ala
    1010                1015                1020
Asp Lys Phe Lys Leu Ser Ile Pro Pro Ser Val Pro Glu Ser Ile Pro
1025            1030                1035                1040
Glu Lys Asp Gln Lys Ile Asp Ser Ile Ser Glu Leu Met Tyr Asp Ile
                1045                1050                1055
Glu Ser Gly Arg Leu Ile Gly Gln Val Ser Lys Arg Pro Ile Pro Gly
            1060                1065                1070
Ser Ile Ala Gly Asp Leu Asn Pro Ile Met Lys Thr Pro Thr Gln Thr
        1075                1080                1085
Asp Ser Val Thr Gly Lys Pro Ile Asp Pro Thr Thr Gly Leu Pro Phe
    1090                1095                1100
Asn Pro Pro Thr Gly His Leu Ile Asn Pro Thr Asn Asn Thr Met
1105                1110                1115                1120
Asp Ser Ser Phe Ala Gly Ala Tyr Lys Tyr Ala Val Ser Asn Gly Ile
                1125                1130                1135
Lys Thr Asp Asn Val Tyr Gly Leu Pro Val Asp Glu Ile Thr Gly Leu
            1140                1145                1150
Pro Lys Asp Pro Val Ser Asp Ile Pro Phe Asn Ser Thr Thr Gly Glu
        1155                1160                1165
Leu Val Asp Pro Ser Thr Gly Lys Pro Ile Asn Asn Tyr Thr Ala Gly
    1170                1175                1180
Ile Val Ser Gly Lys Arg Gly Leu Pro Pro Ile Glu Asp Glu Asn Gly
1185                1190                1195                1200
Asn Leu Phe Asp Pro Ser Thr Lys Leu Pro Ile Asp Gly Asn Asn Gln
                1205                1210                1215
Leu Val Asn Pro Glu Thr Asn Ser Thr Val Ser Gly Ser Thr Ser Gly
            1220                1225                1230
Ser Thr Lys Pro Lys Pro Gly Ile Pro Val Asn Gly Gly Gly Val Val
        1235                1240                1245
Pro Asp Glu Glu Ala Lys Asp Gln Ala Asp Lys Gly Lys Asp Gly Leu
    1250                1255                1260
Ile Val Pro Pro Thr Asn Ser Ile Asn Lys Asp Pro Val Thr Asn Thr
1265                1270                1275                1280
Gln Tyr Ser Asn Thr Thr Gly Asn Ile Ile Asn Pro Glu Thr Gly Lys
                1285                1290                1295
Val Ile Pro Gly Ser Leu Pro Gly Ser Leu Asn Tyr Pro Ser Phe Asn
            1300                1305                1310
Thr Pro Gln Gln Thr Asp Glu Ile Thr Gly Lys Pro Val Asp Thr Val
        1315                1320                1325
Thr Gly Leu Pro Tyr Asp Pro Ser Thr Gly Glu Ile Ile Asp Pro Ala
    1330                1335                1340
Thr Lys Leu Pro Ile Pro Gly Ser Val Ala Gly Asp Glu Ile Leu Thr
1345                1350                1355                1360
Glu Val Leu Asn Ile Thr Thr Asp Glu Val Thr Gly Leu Pro Ile Asp
                1365                1370                1375
Leu Glu Thr Gly Leu Pro Arg Asp Pro Val Ser Gly Leu Pro Gln Leu
            1380                1385                1390
Pro Asn Gly Thr Leu Val Asp Pro Ser Asn Lys Pro Ile Pro Gly
        1395                1400                1405
```

```
Ser His Ser Gly Phe Ile Asn Gly Thr Ser Gly Glu Gln Ser His Glu
    1410                1415                1420

Lys Asp Pro Ser Thr Gly Lys Pro Leu Asp Pro Asn Thr Gly Leu Pro
1425                1430                1435                1440

Phe Asp Glu Asp Ser Gly Ser Leu Ile Asn Pro Glu Thr Gly Asp Lys
                1445                1450                1455

Leu Gln Gly Ser His Ser Gly Thr Phe Met Pro Val Pro Gly Lys Pro
            1460                1465                1470

Gln Gly Glu Asn Gly Gly Ile Met Thr Pro Glu Gln Ile Leu Glu Ala
        1475                1480                1485

Leu Asn Lys Leu Pro Thr Ser Asn Glu Val Asn Ile Ser Pro Arg Pro
    1490                1495                1500

Ser Ser Asp Ala Val Pro Asp Arg Pro Thr Asn Thr Trp Trp Asn Lys
1505                1510                1515                1520

Ile Ser Gly Gln Thr Phe Gln Val Asp Gly Lys Lys Thr Ile Pro Gly
                1525                1530                1535

Ser Ala Ala Ser Val Ile His Thr Ala Leu Gly Thr Pro Thr Gln Thr
            1540                1545                1550

Asp Pro Thr Thr Gly Leu Pro Ser Asp Pro Ser Thr Gly Leu Pro Phe
        1555                1560                1565

Ile Pro Gly Phe Asn Val Leu Val Asp Pro Gln Thr Gly Glu Gln Ile
    1570                1575                1580

Lys Gly Ser Val Pro Tyr Val Ser Leu Tyr Val Lys Glu Lys Asn Ile
1585                1590                1595                1600

Val Thr Glu Ala Ala Tyr Gly Leu Pro Val Asp Pro Lys Thr Gly Phe
                1605                1610                1615

Pro Ile Asp Pro Ile Ser Tyr Leu Pro Phe Ala Lys Asn Gly Glu Leu
            1620                1625                1630

Ile Asp Pro Ile Ser Gly Lys Tyr Phe Ser Gly Ser Ile Ala Gly Phe
        1635                1640                1645

Ile Ser Gly Lys Ala Gly Ser Gln Ser Lys Ser Ser Asp Glu Ser Gly
    1650                1655                1660

Asn Pro Ile Asp Pro Ser Thr Asn Met Pro Tyr Asp Pro Lys Thr Gly
1665                1670                1675                1680

Lys Leu Ile Asp Pro Glu Ser Gly Ile Ala Ile Asp Asn Ser Val Ser
                1685                1690                1695

Gly Val Phe Ala Thr Val Pro Gly Thr Ala Ala Pro Lys Lys Gly Gly
            1700                1705                1710

Val Ile Pro Glu Ser Val Ala Ala Glu Ala Lys Lys Tyr Phe Ala
        1715                1720                1725

Ala Asn Val Glu Gly Glu Gly Glu Gly Glu Glu Val Pro Pro Pro
    1730                1735                1740

Glu Ser Ser Ser Asn Ile Ala Ile Gln Ala Ala Gly Gly Ala Ser Ala
1745                1750                1755                1760

Ala Val Gly Leu Val Ala Ala Val Gly Ala Trp Tyr Ala Ser Arg Asn
                1765                1770                1775

Arg Gln Glu Gly Glu Asp Asp Asp Tyr Gln Met Asp Leu Lys Gln
            1780                1785                1790

Asn Met Lys Lys Lys Arg Lys Lys Arg Val Met Lys Gln Gln Met Lys
        1795                1800                1805

Leu Leu Leu Gln Leu Ser Val Ile His His Ser Gly Thr Asn Leu Lys
    1810                1815                1820

Arg Arg Lys Asp Phe Ser Asn Ser Lys Lys Phe Arg Ile
```

1825            1830            1835

<210> SEQ ID NO 6
<211> LENGTH: 1721
<212> TYPE: PRT
<213> ORGANISM: Cryptosporidium parvum

<400> SEQUENCE: 6

Ile Leu Glu Gly Ser Ile Ala Gly Ile Arg Ser Glu Ser Cys Ile Val
 1               5                  10                  15

Ser Glu Leu Asn Phe Thr Ser Thr Thr Gly Phe Thr Thr Asp Thr Ser
                20                  25                  30

Met Asn Trp Pro Val Ser Ile Thr Ser Gly Glu Leu Lys Asp Pro Asn
            35                  40                  45

Lys Gln Ala Thr Ile Ser Gly Ser Arg Ser Cys Gly Trp Lys Gln Gly
        50                  55                  60

Tyr Ser Ile Asp Ser Ser Thr Gly Phe Arg Val Asp Ser Ile Thr Gly
 65                  70                  75                  80

Leu Pro Thr Asp Pro Tyr Ser Asn Cys Pro Phe Asn Pro Val Thr Gly
                85                  90                  95

Asn Leu Val Ser Arg Ser Thr Gly Lys Thr Ile Pro Asn Thr Tyr Ala
            100                 105                 110

Gly Val Tyr Arg Ser Asn Glu Thr Lys Thr Thr Glu Pro Ser Ala Asn
        115                 120                 125

Thr Tyr Ala Gly Val Tyr Arg Ser Asn Glu Thr Lys Thr Thr Glu Pro
    130                 135                 140

Ser Ala Asn Thr Asn Phe Leu Leu Val Asp Pro Lys Ile Asn Ala Pro
145                 150                 155                 160

Cys Asn Ser Glu Asn Ser Phe Glu Gln Gly Gln Ile Phe Asp Met Gly
                165                 170                 175

Ser Lys Val Tyr Ile Pro Tyr Thr Lys Cys Val Gly Val Lys His Thr
            180                 185                 190

Thr Thr Thr Thr Thr Thr Thr Thr Thr Thr Thr Thr Thr Thr Thr Thr
        195                 200                 205

Thr Thr Thr Thr Thr Thr Thr Thr Thr Thr Thr Thr Thr Thr Thr Thr
    210                 215                 220

Thr Thr Thr Thr Thr Thr Thr Thr Thr Thr Thr Thr Thr Thr Thr Thr
225                 230                 235                 240

Thr Thr Thr Thr Thr Thr Thr Thr Thr Thr Thr Thr Thr Thr Thr Thr
                245                 250                 255

Thr Thr Thr Thr Thr Thr Thr Thr Thr Thr Thr Thr Thr Thr Thr Thr
            260                 265                 270

Thr Thr Thr Thr Thr Thr Thr Thr Thr Thr Thr Thr Thr Thr Thr Thr
        275                 280                 285

Thr Thr Thr Thr Thr Thr Thr Thr Thr Thr Thr Thr Thr Thr Thr Thr
    290                 295                 300

Lys Lys Pro Thr Thr Thr Thr Thr Thr Thr Thr Thr Thr Thr Thr Thr
305                 310                 315                 320

Thr Thr Thr Thr Thr Thr Thr Thr Thr Thr Thr Thr Thr Thr Thr Thr
                325                 330                 335

Lys Lys Pro Thr Thr Thr Thr Thr Thr Thr Thr Thr Thr Thr Thr Thr
            340                 345                 350

Thr Thr Thr Thr Thr Thr Thr Thr Thr Thr Thr Thr Thr Thr Thr Thr
        355                 360                 365

```
Thr Thr Thr Thr Thr Thr Thr Thr Thr Thr Lys Pro Thr Thr Thr Thr
    370                 375                 380

Thr Thr Thr Thr Thr Thr Thr Thr Lys Lys Pro Thr Thr Thr Thr Thr
385                 390                 395                 400

Ala Thr Thr Thr Thr Thr Thr Ser Glu Thr Glu Ser Val Ile Lys Pro
                    405                 410                 415

Asp Glu Trp Cys Trp Leu Glu Lys Asn Gly Glu Cys Glu Ala Lys Gly
                420                 425                 430

Ala Thr Tyr Val Gly Val Ile Gly Lys Asp Gly Arg Ile Glu Asn Gly
            435                 440                 445

Met Ala Phe Thr Met Ile Pro Asn Asp Asp Thr His Val Arg Phe Arg
450                 455                 460

Phe Lys Val Lys Asp Val Gly Asn Thr Ile Ser Val Arg Cys Arg Lys
465                 470                 475                 480

Gly Ala Gly Lys Leu Glu Phe Pro Asp Arg Ser Leu Asp Phe Thr Ile
                485                 490                 495

Pro Pro Val Ala Gly His Asn Ser Cys Ser Ile Ile Val Gly Val Ser
                500                 505                 510

Gly Asp Gly Lys Ile His Val Ser Pro Tyr Gly Ser Lys Asp Val Ser
            515                 520                 525

Leu Ile Ser Ala Pro Ile Gln Pro Ser Glu Leu Phe Asn Glu Val Tyr
530                 535                 540

Cys Asp Thr Cys Thr Ala Lys Tyr Gly Ala Ile His Ser Gly Tyr Gln
545                 550                 555                 560

Thr Ser Ala Asp Phe Val Thr Thr Thr Ala Lys Pro Thr Thr Thr
                565                 570                 575

Thr Thr Gly Ala Pro Gly Gln Pro Thr Thr Thr Thr Gly Ser Pro
                580                 585                 590

Ser Lys Pro Thr Thr Thr Thr Thr Lys Ala Thr Thr Thr Thr
            595                 600                 605

Thr Leu Asn Pro Ile Ile Thr Thr Thr Gln Lys Pro Thr Thr Thr
    610                 615                 620

Thr Thr Thr Lys Val Pro Gly Lys Pro Pro Ile Ala Thr Thr Thr Thr
625                 630                 635                 640

Thr Leu Lys Pro Ile Val Thr Thr Thr Thr Lys Ala Thr Thr Thr
                645                 650                 655

Thr Thr Thr Thr Val Pro Thr Thr Thr Thr Thr Lys Arg Asp Glu
                660                 665                 670

Met Thr Thr Thr Thr Pro Leu Pro Asp Ile Gly Asp Ile Glu Ile
                675                 680                 685

Thr Pro Ile Pro Ile Glu Lys Met Leu Asp Lys Tyr Thr Arg Met Ile
690                 695                 700

Tyr Asp Tyr Asn Ser Gly Leu Leu Leu Asp Ser Asn Asp Glu Pro Ile
705                 710                 715                 720

Pro Gly Ser Gln Ala Gly Gln Ile Ala Asp Thr Ser Asn Leu Phe Pro
                725                 730                 735

Val Gln Thr His Lys Ser Thr Gly Leu Pro Ile Asp Pro Met Val Gly
            740                 745                 750

Leu Pro Phe Asp Pro Lys Ser Gly Asn Leu Val His Pro Tyr Thr Asn
            755                 760                 765

Gln Thr Met Ser Gly Leu Ser Val Ser Tyr Leu Ala Ala Lys Asn Leu
770                 775                 780

Thr Val Asp Thr Asp Glu Thr Tyr Gly Leu Pro Ile Asp Thr Leu Thr
```

```
                785                 790                 795                 800
Gly Tyr Pro Leu Asp Pro Val Ser Leu Ile Pro Phe Asn Pro Glu Thr
                805                 810                 815

Gly Glu Leu Phe Asp Pro Ile Ser Asp Glu Ile Met Asn Gly Thr Ile
                820                 825                 830

Ala Gly Ile Val Ser Gly Ile Ser Ala Ser Glu Ser Leu Leu Ser Gln
                835                 840                 845

Lys Ser Ala Leu Ile Asp Pro Ala Thr Asn Met Val Val Gly Glu Phe
                850                 855                 860

Gly Gly Leu Leu Asn Pro Ala Thr Gly Val Met Ile Pro Gly Phe Leu
865                 870                 875                 880

Gly Pro Ser Glu Gln Thr Gln Phe Ser Pro Glu Ile Glu Asp Gly Gly
                885                 890                 895

Ile Ile Pro Pro Glu Val Ala Ala Ala Asn Ala Asp Lys Phe Lys Leu
                900                 905                 910

Ser Ile Pro Pro Ser Val Pro Glu Ser Ile Pro Glu Lys Asp Gln Lys
                915                 920                 925

Ile Asp Ser Ile Ser Glu Leu Met Tyr Asp Ile Glu Ser Gly Arg Leu
                930                 935                 940

Ile Gly Gln Val Ser Lys Arg Pro Ile Pro Gly Ser Ile Ala Gly Asp
945                 950                 955                 960

Leu Asn Pro Ile Met Lys Thr Pro Thr Gln Thr Asp Ser Val Thr Gly
                965                 970                 975

Lys Pro Ile Asp Pro Thr Thr Gly Leu Pro Phe Asn Pro Thr Gly
                980                 985                 990

His Leu Ile Asn Pro Thr Asn Asn Thr Met Asp Ser Ser Phe Ala
                995                1000                1005

Gly Ala Tyr Lys Tyr Ala Val Ser Asn Gly Ile Lys Thr Asp Asn Val
                1010                1015                1020

Tyr Gly Leu Pro Val Gly Glu Ile Thr Gly Leu Pro Lys Asp Pro Gly
1025                1030                1035                1040

Ser Asp Ile Pro Phe Asn Ser Thr Thr Gly Glu Leu Val Asp Pro Ser
                1045                1050                1055

Thr Gly Lys Pro Ile Asn Asn Ser Thr Ala Gly Ile Val Ser Gly Lys
                1060                1065                1070

Pro Gly Leu Pro Pro Ile Glu Asp Glu Asn Gly Asn Leu Phe Asp Pro
                1075                1080                1085

Ser Thr Asn Leu Pro Ile Asp Gly Asn Asn Gln Leu Val Asn Pro Glu
                1090                1095                1100

Thr Asn Ser Thr Val Ser Gly Ser Thr Ser Gly Thr Thr Lys Pro Lys
1105                1110                1115                1120

Pro Gly Ile Pro Val Asn Gly Gly Val Val Pro Asp Glu Glu Ala
                1125                1130                1135

Lys Asp Gln Ala Asp Lys Gly Lys Asp Gly Leu Ile Val Pro Pro Thr
                1140                1145                1150

Asn Ser Ile Asn Lys Asp Pro Val Thr Asn Thr Gln Tyr Ser Asn Thr
                1155                1160                1165

Thr Gly Asn Ile Ile Asn Pro Glu Thr Gly Lys Val Ile Pro Gly Ser
                1170                1175                1180

Leu Pro Gly Ser Leu Asn Tyr Pro Ser Phe Asn Thr Pro Gln Gln Thr
1185                1190                1195                1200

Asp Glu Ile Thr Gly Lys Pro Val Asp Thr Val Thr Gly Leu Pro Tyr
                1205                1210                1215
```

-continued

```
Asp Pro Ser Thr Gly Glu Ile Ile Asp Pro Ala Thr Lys Leu Pro Ile
        1220                1225                1230
Pro Gly Ser Val Ala Gly Asp Glu Ile Leu Thr Glu Val Leu Asn Ile
    1235                1240                1245
Thr Thr Asp Glu Val Thr Gly Leu Pro Ile Asp Leu Glu Thr Gly Leu
    1250                1255                1260
Pro Arg Asp Pro Val Ser Gly Leu Pro Gln Leu Pro Asn Gly Thr Leu
1265                1270                1275                1280
Val Asp Pro Ser Asn Lys Lys Pro Ile Pro Gly Ser His Ser Gly Phe
            1285                1290                1295
Ile Asn Gly Thr Ser Gly Glu Gln Ser His Glu Lys Asp Pro Ser Thr
            1300                1305                1310
Gly Lys Pro Leu Asp Pro Asn Thr Gly Leu His Pro Phe Asp Glu Asp
        1315                1320                1325
Ser Gly Ser Leu Ile Asn Pro Glu Thr Gly Asp Lys Leu Gln Gly Ser
    1330                1335                1340
His Ser Gly Thr Phe Met Pro Val Pro Gly Lys Pro Gln Gly Glu Asn
1345                1350                1355                1360
Gly Gly Ile Met Thr Pro Glu Gln Ile Leu Glu Ala Leu Asn Lys Leu
        1365                1370                1375
Pro Thr Ser Asn Glu Val Asn Ile Ser Pro Arg Pro Ser Ser Asp Ala
    1380                1385                1390
Val Pro Asp Arg Pro Thr Asn Thr Trp Trp Asn Lys Ile Ser Gly Gln
            1395                1400                1405
Thr Tyr Gln Val Asp Gly Lys Lys Thr Ile Pro Gly Ser Ala Ala Ser
    1410                1415                1420
Val Ile His Thr Ala Leu Gly Thr Pro Thr Gln Thr Asp Pro Thr Thr
1425                1430                1435                1440
Gly Leu Pro Ser Asp Pro Ser Thr Gly Leu Pro Phe Ile Pro Gly Phe
            1445                1450                1455
Asn Val Leu Val Asp Pro Gln Thr Gly Glu Gln Ile Lys Gly Ser Val
            1460                1465                1470
Pro Tyr Val Ser Leu Tyr Val Lys Glu Lys Asn Ile Val Thr Glu Ala
        1475                1480                1485
Ala Tyr Gly Leu Pro Val Asp Pro Lys Thr Gly Phe Pro Ile Asp Pro
    1490                1495                1500
Ile Ser Tyr Leu Pro Phe Ala Lys Asn Gly Glu Leu Ile Asp Pro Ile
1505                1510                1515                1520
Ser Gly Lys Tyr Phe Ser Gly Ser Ile Ala Gly Phe Ile Ser Gly Lys
            1525                1530                1535
Ala Gly Ser Gln Ser Lys Ser Ser Asp Glu Ser Gly Asn Pro Ile Asp
            1540                1545                1550
Pro Ser Thr Asn Met Pro Tyr Asp Pro Lys Gly Gly Lys Leu Ile Asp
        1555                1560                1565
Pro Glu Ser Gly Ile Ala Ile Asp Asn Ser Val Ser Gly Val Phe Ala
    1570                1575                1580
Thr Val Pro Gly Thr Ala Ala Pro Lys Lys Gly Gly Val Ile Pro Glu
1585                1590                1595                1600
Ser Val Ala Ala Glu Ala Ala Lys Lys Tyr Phe Ala Ala Asn Val Glu
            1605                1610                1615
Gly Glu Gly Glu Gly Glu Val Pro Pro Pro Glu Ser Ser Ser
            1620                1625                1630
```

```
Asn Ile Ala Ile Gln Ala Ala Gly Gly Ala Ser Ala Ala Val Gly Leu
        1635                1640                1645

Val Ala Ala Val Gly Ala Trp Tyr Ala Ser Arg Asn Arg Gln Glu Gly
    1650                1655                1660

Glu Asp Asp Asp Tyr Gln Met Asp Leu Lys Gln Asn Met Lys Lys
1665                1670                1675                1680

Lys Arg Lys Lys Arg Val Met Lys Gln Gln Met Lys Leu Leu Leu Gln
            1685                1690                1695

Leu Ser Val Ile His His Ser Gly Thr Asn Leu Lys Arg Arg Lys Asp
                1700                1705                1710

Phe Ser Asn Ser Lys Lys Phe Arg Ile
            1715                1720

<210> SEQ ID NO 7
<211> LENGTH: 303
<212> TYPE: PRT
<213> ORGANISM: Cryptosporidium parvum

<400> SEQUENCE: 7

Met Val Asn Ile Lys Val Ser Ser Ala Ile Ala Leu Val Ala Val
  1               5                  10                  15

Ile Met Asn Pro Leu Phe Ser Leu Ala Phe Lys Ser Ser Asn Arg Leu
                20                  25                  30

Glu Met Arg Ile Glu Ser Ser Gly Ala Val Ser Asn Glu Lys Phe Val
            35                  40                  45

Ile Pro Ser Leu Pro Ser Asp Leu Asp Pro Thr Thr Phe Leu Leu Ile
        50                  55                  60

Asp Ser Thr Gly Lys Lys Phe Ser Pro Tyr Thr Gly Lys His Ala Asp
 65                  70                  75                  80

Ala Ser Thr Thr Ser Ser Ala Tyr Ser Ala Pro Phe Glu Leu Asp Val
                85                  90                  95

Ser Gly Val Pro Ile Glu Pro Asn Thr Arg Arg Met Val Asp Pro Val
            100                 105                 110

Ser Leu Met Leu Phe Asp Asn Ser Thr Gly Val Met Tyr Asp Pro Asn
        115                 120                 125

Thr Asn Ser Ile Leu Glu Gly Ser Ile Ala Gly Ile Arg Ser Glu Ser
130                 135                 140

Cys Ile Val Ser Glu Leu Asn Phe Thr Ser Thr Thr Gly Phe Thr Thr
145                 150                 155                 160

Asp Thr Ser Met Asn Trp Pro Val Ser Ile Thr Ser Gly Glu Leu Lys
                165                 170                 175

Asp Pro Asn Lys Gln Ala Thr Ile Ser Gly Ser Arg Ser Cys Gly Trp
            180                 185                 190

Lys Gln Gly Tyr Ser Ile Asp Ser Ser Thr Gly Phe Arg Val Asp Ser
        195                 200                 205

Ile Thr Gly Leu Pro Thr Asp Pro Tyr Pro Asn Cys Pro Phe Asn Pro
    210                 215                 220

Val Thr Gly Asn Leu Val Ser Arg Ser Thr Gly Lys Thr Ile Pro Asn
225                 230                 235                 240

Thr Tyr Ala Gly Val Tyr Arg Ser Asn Glu Thr Lys Thr Thr Glu Pro
                245                 250                 255

Ser Ala Asn Thr Asn Phe Leu Leu Val Asp Pro Lys Ile Asn Ala Pro
            260                 265                 270

Cys Asn Ser Glu Asn Ser Phe Glu Gln Val Gln Ile Phe Asp Met Gly
        275                 280                 285
```

Ser Lys Val Tyr Ile Pro Tyr Thr Lys Cys Val Gly Val Lys His
        290                 295                 300

<210> SEQ ID NO 8
<211> LENGTH: 216
<212> TYPE: PRT
<213> ORGANISM: Cryptosporidium parvum

<400> SEQUENCE: 8

Thr Thr Thr Thr Thr Thr Thr Thr Thr Thr Thr Thr Thr Thr Thr Thr
  1               5                  10                  15

Thr Thr Thr Thr Thr Thr Thr Thr Thr Thr Thr Thr Thr Thr Thr Thr
                 20                  25                  30

Thr Thr Thr Thr Thr Thr Thr Thr Thr Thr Thr Thr Thr Thr Thr Thr
             35                  40                  45

Thr Thr Thr Thr Thr Thr Thr Thr Thr Thr Thr Thr Thr Thr Thr Thr
         50                  55                  60

Thr Thr Thr Lys Lys Pro Thr Thr Thr Thr Thr Thr Thr Thr Thr Thr
 65                  70                  75                  80

Thr Thr Thr Thr Thr Thr Thr Thr Thr Thr Thr Thr Thr Thr Thr Thr
                 85                  90                  95

Thr Thr Thr Thr Thr Thr Thr Thr Thr Thr Thr Thr Thr Thr Thr Thr
            100                 105                 110

Thr Lys Lys Pro Thr Thr Thr Thr Thr Thr Thr Thr Thr Thr Thr Thr
        115                 120                 125

Thr Thr Thr Thr Thr Thr Thr Thr Thr Thr Thr Thr Thr Thr Thr Thr
    130                 135                 140

Thr Lys Lys Pro Thr Thr Thr Thr Thr Thr Thr Thr Thr Thr Thr Thr
145                 150                 155                 160

Thr Thr Thr Thr Thr Thr Thr Thr Thr Thr Thr Thr Thr Thr Thr Thr
                165                 170                 175

Thr Thr Thr Thr Thr Ala Thr Thr Thr Lys Lys Pro Thr Thr Thr
            180                 185                 190

Thr Thr Thr Thr Thr Thr Thr Thr Lys Lys Pro Thr Thr Thr Thr
        195                 200                 205

Thr Ala Thr Thr Thr Thr Thr Thr
    210                 215

<210> SEQ ID NO 9
<211> LENGTH: 159
<212> TYPE: PRT
<213> ORGANISM: Cryptosporidium parvum

<400> SEQUENCE: 9

Ser Glu Thr Glu Ser Val Ile Lys Pro Asp Glu Trp Cys Trp Leu Glu
  1               5                  10                  15

Lys Asn Gly Glu Cys Glu Ala Lys Gly Ala Thr Tyr Val Gly Val Ile
                 20                  25                  30

Gly Lys Asp Gly Arg Ile Glu Asn Gly Met Ala Phe Thr Met Ile Pro
             35                  40                  45

Asn Asp Asp Thr His Val Arg Phe Arg Phe Lys Val Lys Asp Val Gly
         50                  55                  60

Asn Thr Ile Ser Val Arg Cys Gly Lys Gly Ala Gly Lys Leu Glu Phe
 65                  70                  75                  80

Pro Asp Arg Ser Leu Asp Phe Thr Ile Pro Pro Val Ala Gly His Asn
                 85                  90                  95

-continued

Ser Cys Ser Ile Ile Val Gly Val Ser Gly Gly Lys Ile His Val
            100                 105                 110

Ser Pro Tyr Gly Ser Lys Asp Val Ser Leu Ile Ser Ala Pro Ile Gln
        115                 120                 125

Pro Cys Glu Leu Phe Asn Glu Val Tyr Cys Asp Thr Cys Thr Ala Lys
    130                 135                 140

Tyr Gly Ala Ile His Ser Gly Tyr Gln Thr Ser Ala Asp Phe Val
145                 150                 155

<210> SEQ ID NO 10
<211> LENGTH: 112
<212> TYPE: PRT
<213> ORGANISM: Cryptosporidium parvum

<400> SEQUENCE: 10

Thr Thr Thr Thr Ala Lys Pro Thr Thr Thr Thr Gly Ala Pro Gly
  1               5                  10                  15

Gln Pro Thr Thr Thr Thr Thr Gly Ser Pro Ser Lys Pro Thr Thr Thr
             20                  25                  30

Thr Thr Thr Lys Ala Thr Thr Thr Thr Ile Leu Asn Pro Ile Ile
         35                  40                  45

Thr Thr Thr Gln Lys Pro Thr Thr Thr Thr Thr Lys Val Pro
     50                  55                  60

Gly Lys Pro Pro Ile Ala Thr Thr Thr Thr Leu Lys Pro Ile Val
 65                  70                  75                  80

Thr Thr Thr Thr Thr Lys Ala Thr Thr Thr Thr Thr Thr Val Pro
                 85                  90                  95

Thr Thr Thr Thr Thr Thr Lys Arg Asp Glu Met Thr Thr Thr Thr
                100                 105                 110

<210> SEQ ID NO 11
<211> LENGTH: 1042
<212> TYPE: PRT
<213> ORGANISM: Cryptosporidium parvum

<400> SEQUENCE: 11

Pro Leu Pro Asp Ile Gly Asp Ile Glu Ile Thr Pro Ile Pro Ile Glu
  1               5                  10                  15

Lys Met Leu Asp Lys Tyr Thr Arg Met Ile Tyr Asp Tyr Asn Ser Gly
             20                  25                  30

Leu Leu Leu Asp Ser Asn Asp Glu Pro Ile Pro Gly Ser Gln Ala Gly
         35                  40                  45

Gln Ile Ala Asp Thr Ser Asn Leu Phe Pro Val Gln Thr His Lys Ser
     50                  55                  60

Thr Gly Leu Pro Ile Asp Pro Met Val Gly Leu Pro Phe Asp Pro Lys
 65                  70                  75                  80

Ser Gly Asn Leu Val His Pro Tyr Thr Asn Gln Thr Met Ser Gly Leu
                 85                  90                  95

Ser Val Ser Tyr Leu Ala Ala Lys Asn Leu Thr Val Asp Thr Asp Glu
                100                 105                 110

Thr Tyr Gly Leu Pro Ile Asp Thr Leu Thr Gly Tyr Pro Leu Asp Pro
            115                 120                 125

Val Ser Leu Ile Pro Phe Asn Pro Glu Thr Gly Glu Leu Phe Asp Pro
    130                 135                 140

Ile Ser Asp Glu Ile Met Asn Gly Thr Ile Ala Gly Ile Val Ser Gly

-continued

```
                145                 150                 155                 160
Ile Ser Ala Ser Glu Ser Leu Leu Ser Gln Lys Ser Ala Pro Ile Asp
                165                 170                 175
Pro Ala Thr Asn Met Val Val Gly Glu Phe Gly Gly Leu Leu Asn Pro
                180                 185                 190
Ala Thr Gly Val Met Ile Pro Gly Ser Leu Gly Pro Ser Glu Gln Thr
                195                 200                 205
Pro Phe Ser Pro Glu Ile Glu Asp Gly Gly Ile Ile Pro Pro Glu Val
                210                 215                 220
Ala Ala Ala Asn Ala Asp Lys Phe Lys Leu Ser Ile Pro Pro Ser Val
225                 230                 235                 240
Pro Glu Ser Ile Pro Glu Lys Asp Gln Lys Ile Asp Ser Ile Ser Glu
                245                 250                 255
Leu Met Tyr Asp Ile Glu Ser Gly Arg Leu Ile Gly Gln Val Ser Lys
                260                 265                 270
Arg Pro Ile Pro Gly Ser Ile Ala Gly Asp Leu Asn Pro Ile Met Lys
                275                 280                 285
Thr Pro Thr Gln Thr Asp Ser Val Thr Gly Lys Pro Ile Asp Pro Thr
                290                 295                 300
Thr Gly Leu Pro Phe Asn Pro Pro Thr Gly His Leu Ile Asn Pro Thr
305                 310                 315                 320
Asn Asn Asn Thr Met Asp Ser Ser Phe Ala Gly Ala Tyr Lys Tyr Ala
                325                 330                 335
Val Ser Asn Gly Ile Lys Thr Asp Asn Val Tyr Gly Leu Pro Val Asp
                340                 345                 350
Glu Ile Thr Gly Leu Pro Lys Asp Pro Val Ser Asp Ile Pro Phe Asn
                355                 360                 365
Ser Thr Thr Gly Glu Leu Val Asp Pro Ser Thr Gly Lys Pro Ile Asn
                370                 375                 380
Asn Tyr Thr Ala Gly Ile Val Ser Gly Lys Arg Gly Leu Pro Pro Ile
385                 390                 395                 400
Glu Asp Glu Asn Gly Asn Leu Phe Asp Pro Ser Thr Lys Leu Pro Ile
                405                 410                 415
Asp Gly Asn Asn Gln Leu Val Asn Pro Glu Thr Asn Ser Thr Val Ser
                420                 425                 430
Gly Ser Thr Ser Gly Ser Thr Lys Pro Lys Pro Gly Ile Pro Val Asn
                435                 440                 445
Gly Gly Gly Val Val Pro Asp Glu Ala Lys Asp Gln Ala Asp Lys
                450                 455                 460
Gly Lys Asp Gly Leu Ile Val Pro Pro Thr Asn Ser Ile Asn Lys Asp
465                 470                 475                 480
Pro Val Thr Asn Thr Gln Tyr Ser Asn Thr Gly Asn Ile Ile Asn
                485                 490                 495
Pro Glu Thr Gly Lys Val Ile Pro Gly Ser Leu Pro Gly Ser Leu Asn
                500                 505                 510
Tyr Pro Ser Phe Asn Thr Pro Gln Gln Thr Asp Glu Ile Thr Gly Lys
                515                 520                 525
Pro Val Asp Thr Val Thr Gly Leu Pro Tyr Asp Pro Ser Thr Gly Glu
                530                 535                 540
Ile Ile Asp Pro Ala Thr Lys Leu Pro Ile Pro Gly Ser Val Ala Gly
545                 550                 555                 560
Asp Glu Ile Leu Thr Glu Val Leu Asn Ile Thr Thr Asp Glu Val Thr
                565                 570                 575
```

-continued

```
Gly Leu Pro Ile Asp Leu Glu Thr Gly Leu Pro Arg Asp Pro Val Ser
                580                 585                 590
Gly Leu Pro Gln Leu Pro Asn Gly Thr Leu Val Asp Pro Ser Asn Lys
            595                 600                 605
Lys Pro Ile Pro Gly Ser His Ser Gly Phe Ile Asn Gly Thr Ser Gly
        610                 615                 620
Glu Gln Ser His Glu Lys Asp Pro Ser Thr Gly Lys Pro Leu Asp Pro
625                 630                 635                 640
Asn Thr Gly Leu Pro Phe Asp Glu Asp Ser Gly Ser Leu Ile Asn Pro
                645                 650                 655
Glu Thr Gly Asp Lys Leu Gln Gly Ser His Ser Gly Thr Phe Met Pro
            660                 665                 670
Val Pro Gly Lys Pro Gln Gly Glu Asn Gly Gly Ile Met Thr Pro Glu
        675                 680                 685
Gln Ile Leu Glu Ala Leu Asn Lys Leu Pro Thr Ser Asn Glu Val Asn
                690                 695                 700
Ile Ser Pro Arg Pro Ser Ser Asp Ala Val Pro Asp Arg Pro Thr Asn
705                 710                 715                 720
Thr Trp Trp Asn Lys Ile Ser Gly Gln Thr Phe Gln Val Asp Gly Lys
                725                 730                 735
Lys Thr Ile Pro Gly Ser Ala Ala Ser Val Ile His Thr Ala Leu Gly
            740                 745                 750
Thr Pro Thr Gln Thr Asp Pro Thr Thr Gly Leu Pro Ser Asp Pro Ser
        755                 760                 765
Thr Gly Leu Pro Phe Ile Pro Gly Phe Asn Val Leu Val Asp Pro Gln
    770                 775                 780
Thr Gly Glu Gln Ile Lys Gly Ser Val Pro Tyr Val Ser Leu Tyr Val
785                 790                 795                 800
Lys Glu Lys Asn Ile Val Thr Glu Ala Ala Tyr Gly Leu Pro Val Asp
                805                 810                 815
Pro Lys Thr Gly Phe Pro Ile Asp Pro Ile Ser Tyr Leu Pro Phe Ala
            820                 825                 830
Lys Asn Gly Glu Leu Ile Asp Pro Ile Ser Gly Lys Tyr Phe Ser Gly
        835                 840                 845
Ser Ile Ala Gly Phe Ile Ser Gly Lys Ala Gly Ser Gln Ser Lys Ser
    850                 855                 860
Ser Asp Glu Ser Gly Asn Pro Ile Asp Pro Ser Thr Asn Met Pro Tyr
865                 870                 875                 880
Asp Pro Lys Thr Gly Lys Leu Ile Asp Pro Glu Ser Gly Ile Ala Ile
                885                 890                 895
Asp Asn Ser Val Ser Gly Val Phe Ala Thr Val Pro Gly Thr Ala Ala
            900                 905                 910
Pro Lys Lys Gly Gly Val Ile Pro Glu Ser Val Ala Ala Glu Ala Ala
        915                 920                 925
Lys Lys Tyr Phe Ala Ala Asn Val Glu Gly Glu Gly Glu Gly Glu Glu
    930                 935                 940
Val Pro Pro Pro Glu Ser Ser Asn Ile Ala Ile Gln Ala Ala
945                 950                 955                 960
Gly Gly Ala Ser Ala Ala Val Gly Leu Val Ala Ala Val Gly Ala Trp
                965                 970                 975
Tyr Ala Ser Arg Asn Arg Gln Gly Gly Glu Asp Asp Asp Tyr Gln
            980                 985                 990
```

```
Met Asp Leu Lys Gln Asn Met Lys Lys Arg Lys Lys Arg Val Met
        995                 1000                1005
Lys Gln Gln Met Lys Leu Leu Leu Gln Leu Ser Val Ile His His Ser
   1010                1015                1020
Gly Thr Asn Leu Lys Arg Arg Lys Asp Phe Ser Asn Ser Lys Lys Phe
1025                1030                1035                1040
Arg Ile

<210> SEQ ID NO 12
<211> LENGTH: 128
<212> TYPE: PRT
<213> ORGANISM: Cryptosporidium parvum

<400> SEQUENCE: 12

Met Gly Ser Lys Val Tyr Ile Pro Tyr Thr Lys Cys Val Gly Val Lys
  1               5                  10                  15
His Thr Thr Thr Thr Thr Thr Thr Thr Thr Thr Thr Thr Thr Thr Thr
             20                  25                  30
Thr Thr Thr Thr Thr Thr Thr Thr Thr Thr Thr Thr Thr Thr Thr Thr
         35                  40                  45
Thr Thr Thr Thr Thr Thr Thr Thr Thr Thr Thr Thr Thr Thr Thr Thr
     50                  55                  60
Thr Thr Thr Thr Thr Thr Thr Thr Thr Thr Thr Thr Thr Thr Thr Thr
 65                  70                  75                  80
Thr Thr Lys Lys Pro Thr Thr Thr Thr Thr Thr Thr Thr Thr Thr Thr
                 85                  90                  95
Thr Lys Lys Pro Thr Thr Thr Thr Thr Ala Thr Thr Thr Thr Thr Thr
             100                 105                 110
Ser Glu Thr Glu Ser Val Ile Lys Pro Asp Glu Trp Cys Trp Leu Glu
         115                 120                 125

<210> SEQ ID NO 13
<211> LENGTH: 130
<212> TYPE: PRT
<213> ORGANISM: Cryptosporidium parvum

<400> SEQUENCE: 13

Met Gly Ser Lys Val Tyr Ile Pro Tyr Thr Lys Cys Val Gly Val Lys
  1               5                  10                  15
His Thr Thr Thr Thr Thr Thr Thr Thr Thr Thr Thr Thr Thr Thr Thr
             20                  25                  30
Thr Thr Thr Thr Thr Thr Thr Thr Thr Thr Thr Thr Thr Thr Thr Thr
         35                  40                  45
Thr Thr Thr Thr Thr Thr Thr Thr Thr Thr Thr Thr Thr Thr Thr Thr
     50                  55                  60
Thr Thr Thr Thr Thr Thr Thr Thr Thr Thr Thr Thr Thr Thr Thr Thr
 65                  70                  75                  80
Thr Thr Thr Thr Lys Lys Pro Thr Thr Thr Thr Thr Thr Thr Thr Thr
                 85                  90                  95
Thr Thr Thr Lys Lys Pro Thr Thr Thr Thr Thr Ala Thr Thr Thr Thr
             100                 105                 110
Thr Thr Ser Glu Thr Glu Ser Val Ile Lys Pro Asp Glu Trp Cys Trp
         115                 120                 125
Leu Glu
    130
```

-continued

```
<210> SEQ ID NO 14
<211> LENGTH: 130
<212> TYPE: PRT
<213> ORGANISM: Cryptosporidium parvum

<400> SEQUENCE: 14

Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Lys Pro
        35                  40                  45

Thr Thr Thr Thr Thr Thr Thr Thr Thr Thr Thr Thr Thr Thr Thr
    50                  55                  60

Thr Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr Thr
                85                  90                  95

Thr Thr Thr Lys Lys Pro Thr Thr Thr Thr Ala Thr Thr Thr Thr
            100                 105                 110

Thr Thr Ser Glu Thr Glu Ser Val Ile Lys Pro Asp Glu Trp Cys Trp
        115                 120                 125

Leu Glu
    130

<210> SEQ ID NO 15
<211> LENGTH: 138
<212> TYPE: PRT
<213> ORGANISM: Cryptosporidium parvum

<400> SEQUENCE: 15

Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr Thr
    50                  55                  60

Thr Thr Thr Thr Thr Thr Thr Thr Thr Thr Thr Thr Thr Thr Thr
65                  70                  75                  80

Thr Thr Thr Thr Thr Thr Thr Thr Thr Thr Thr Lys Lys Pro Thr
                85                  90                  95

Thr Thr Thr Thr Thr Thr Thr Thr Thr Lys Lys Pro Thr Thr
            100                 105                 110

Thr Thr Thr Ala Thr Thr Thr Thr Thr Ser Glu Thr Glu Ser Val
        115                 120                 125

Ile Lys Pro Asp Glu Trp Cys Trp Leu Glu
    130                 135

<210> SEQ ID NO 16
<211> LENGTH: 124
<212> TYPE: PRT
<213> ORGANISM: Cryptosporidium parvum

<400> SEQUENCE: 16

Met Gly Ser Lys Val Tyr Ile Pro Tyr Thr Lys Cys Val Gly Val Lys
 1               5                  10                  15
```

His Thr Thr Thr Thr Thr Thr Thr Thr Thr Thr Thr Thr Thr
        20                  25                  30

Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr
        50                  55                  60

Thr Thr Thr Thr Thr Thr Thr Thr Thr Thr Thr Thr Lys Glu
65                  70                  75                  80

Pro Thr Thr Thr Thr Thr Thr Thr Thr Thr Thr Thr Lys Lys Pro
                85                  90                  95

Thr Thr Thr Thr Thr Ala Thr Thr Thr Thr Thr Ser Glu Thr Glu
            100                 105                 110

Ser Val Ile Lys Pro Asp Glu Trp Cys Trp Leu Glu
            115                 120

<210> SEQ ID NO 17
<211> LENGTH: 175
<212> TYPE: PRT
<213> ORGANISM: Cryptosporidium parvum

<400> SEQUENCE: 17

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr
        20                  25                  30

Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr
                85                  90                  95

Thr Thr Thr Thr Thr Thr Thr Thr Thr Thr Thr Thr Thr Thr
            100                 105                 110

Thr Thr Thr Thr Thr Thr Thr Thr Thr Thr Thr Thr Thr Thr
            115                 120                 125

Thr Lys Lys Pro Thr Thr Thr Thr Thr Thr Thr Thr Thr Thr
130                 135                 140

Lys Lys Pro Thr Thr Thr Thr Ala Thr Thr Thr Thr Thr Ser
145                 150                 155                 160

Glu Thr Glu Ser Val Ile Lys Pro Asp Glu Trp Cys Trp Leu Glu
                165                 170                 175

<210> SEQ ID NO 18
<211> LENGTH: 150
<212> TYPE: PRT
<213> ORGANISM: Cryptosporidium parvum

<400> SEQUENCE: 18

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr
        20                  25                  30

Thr Thr Thr Thr Thr Thr Thr Thr Thr Thr Thr Thr Thr Thr
        35                  40                  45

-continued

Thr Thr Thr Thr Thr Thr Thr Thr Thr Thr Ala Thr Thr Thr
        50                  55                  60

Thr Thr Thr Thr Thr Thr Thr Thr Thr Thr Thr Thr Thr Thr
 65                  70                  75                  80

Thr Thr Thr Thr Thr Thr Thr Thr Thr Thr Thr Thr Thr Thr
            85                  90                  95

Thr Thr Thr Thr Thr Thr Thr Lys Lys Pro Thr Thr Thr Thr
           100                 105                 110

Thr Thr Thr Thr Thr Thr Lys Lys Pro Thr Thr Thr Thr Ala
       115                 120                 125

Thr Thr Thr Thr Thr Ser Glu Thr Glu Ser Val Ile Lys Pro Asp
    130                 135                 140

Glu Trp Cys Trp Leu Glu
145                 150

<210> SEQ ID NO 19
<211> LENGTH: 91
<212> TYPE: PRT
<213> ORGANISM: Cryptosporidium parvum

<400> SEQUENCE: 19

Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
            20                  25                  30

Thr Thr Thr Thr Thr Thr Thr Thr Thr Thr Thr Thr Thr Thr Thr
        35                  40                  45

Thr Thr Thr Thr Thr Thr Thr Thr Thr Thr Thr Lys Lys Pro Thr
    50                  55                  60

Thr Thr Thr Thr Ala Thr Thr Thr Thr Thr Ser Glu Thr Glu Ser
 65                  70                  75                  80

Val Ile Lys Pro Asp Glu Trp Cys Trp Leu Glu
            85                  90

<210> SEQ ID NO 20
<211> LENGTH: 249
<212> TYPE: PRT
<213> ORGANISM: Cryptosporidium parvum

<400> SEQUENCE: 20

Met Gly Ser Lys Val Tyr Ile Pro Tyr Thr Lys Cys Val Gly Val Lys
 1               5                  10                  15

His Thr Thr Thr Thr Thr Thr Thr Thr Thr Thr Thr Thr Thr Thr
            20                  25                  30

Thr Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr Thr
    50                  55                  60

Thr Thr Thr Thr Thr Thr Thr Thr Thr Thr Thr Thr Thr Thr Thr
 65                  70                  75                  80

Thr Thr Thr Thr Thr Thr Thr Thr Thr Thr Thr Thr Thr Thr Thr
            85                  90                  95

Thr Thr Thr Thr Thr Thr Thr Thr Thr Thr Thr Thr Thr Thr Thr
           100                 105                 110

Thr Thr Thr Thr Thr Thr Thr Thr Thr Thr Thr Thr Thr Thr Thr
       115                 120                 125

```
Thr Thr Thr Thr Thr Thr Thr Thr Thr Thr Thr Thr Thr Thr Thr
    130                 135                 140
Thr Thr Thr Thr Thr Thr Thr Thr Thr Thr Thr Thr Thr Thr Thr
145                 150                 155                 160
Thr Thr Lys Lys Pro Thr Thr Thr Thr Thr Thr Thr Thr Thr Thr
            165                 170                 175
Thr Thr Thr Thr Thr Thr Thr Thr Thr Thr Thr Thr Thr Thr Thr
            180                 185                 190
Thr Thr Thr Thr Thr Thr Thr Thr Thr Thr Thr Lys Pro Thr Thr
            195                 200                 205
Thr Thr Thr Thr Thr Thr Thr Thr Thr Lys Lys Pro Thr Thr Thr
    210                 215                 220
Thr Thr Ala Thr Thr Thr Thr Thr Thr Ser Glu Thr Glu Ser Val Ile
225                 230                 235                 240

Lys Pro Asp Glu Trp Cys Trp Leu Glu
                245

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 21
caggtaccca tgaattggcc ggtaagtatc                                    30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
caggtaccct ctgaaactga gagtgtaatt                                    30

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 23
ggaaggttca attgcagg                                                 18

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 24
ccattcaacc ctgtcactgg aa                                            22

<210> SEQ ID NO 25
<211> LENGTH: 16
<212> TYPE: DNA
<213> ORGANISM: Artificial Sequence
<220> FEATURE:
```

```
<223> OTHER INFORMATION: Description of Artificial Sequence: Primer

<400> SEQUENCE: 25
gtccattcaa cctgtc                                                    16

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
caacttatgt tggtgttatc gg                                             22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 27
cactctggat atcaaacttc a                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
ggttccaggt aagccaccaa t                                              21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
caggaatttc tgcaagtgag tc                                             22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 30
atgatattga gtcaggtaga ct                                             22

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
cccaataatg aagacacc                                                  18
```

```
<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 32
tcaatccacc aactggc                                                    17

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 33
ccaacagcac tgtctcagga tc                                              22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 34
aacttcaggt actacaaaac c                                               21

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 35
cagtcaatgg tggaggtg                                                   18

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 36
ctactggtaa cattattaac cc                                              22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
aactaattac caattccagg                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer
```

<400> SEQUENCE: 38
cagatgaagt aacaggtttg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
caagagatcc agtatcagga                                              20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
caattccagg ttcacattc                                               19

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 41
gatcacattc tggtacatta t                                            21

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 42
ggtcaaacct accagg                                                  16

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 43
ccaattgatc caattagtta c                                            21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 44
gactataaca gtggtttatt a                                            21

<210> SEQ ID NO 45
<211> LENGTH: 29

<212> TYPE: DNA
<213> ORGANISM: Artificial Sequence
<220> FEATURE:
<223> OTHER INFORMATION: Description of Artificial Sequence: Primer

<400> SEQUENCE: 45
cctctagatt agtgtttcac tccaacaca                                29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 46
cctctagatt atacgaaatc agctgaagt                                29

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 47
gatacaatgc aagattcgct tctaatacct gc                            32

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 48
ccacaagatc ttgaaccaga aat                                      23

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 49
atagtgacca gagggttg                                            18

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 50
cactaggctc agtggtctta gt                                       22

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 51

```
atgtgtgcct tgctgccc                                              18

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 52
aaatccaaac ttctatctgg g                                          21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 53
agttggtttg cttggacttc c                                          21

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 54
tttcgtctct cttggta                                               17

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 55
accgataaac cagacattgt t                                          21

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 56
agtctacctg actcaatatc at                                         22

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 57
attggctttc ctgttgat                                              18

<210> SEQ ID NO 58
<211> LENGTH: 22
<212> TYPE: DNA
<213> ORGANISM: Artificial Sequence
```

-continued

<220> FEATURE:
<223> OTHER INFORMATION: Description of Artificial Sequence: Primer

<400> SEQUENCE: 58
tgggttaata atgttaccag ta 22

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 59
ggatcatatg gcaaaccag 19

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 60
aatgtgaacc tggaattggt t 21

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 61
cttcattact tgttggc 17

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 62
gtcctgttgt tggatcag 18

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 63
cactgaaata tttaccagag 20

<210> SEQ ID NO 64
<211> LENGTH: 1509
<212> TYPE: DNA
<213> ORGANISM: Cryptosporidium parvum

<400> SEQUENCE: 64
agtaagggtc aattatttaa cccagtaagt aagttgtgtg tacgacttaa agacaatgtt 60
gtaggtggag gagctctggt tttggatgat tgtcgtaaag ctagtgatgg aagtggatta 120

-continued

```
ttcgaattaa tgccaaacaa tcagctcaga ttagctagag gtggaaatct atgcttaaca      180
agtccaggag ataagccagg agtcgcgaat gttgcattaa actcagcagc cagttccaca      240
agtgtggtta gaacaggtat tgagaatggt ccagcaatgg ctgttgatgg aaaggataca      300
tcatattggt tgtcagattc ttcaactcct ggtaaagatt ctgcaaatgt taacttttg       360 agtgataccg gttcagttac aaaacttaaa gatatcttta ttgagtggaa atatcctgcc      420 attgactta atattgattt aagtgaaaat ggaaaggaat atcaaaccca gtttctgtg        480 aataataatg gattaatgtc aaccacttat tcattagaag gaaagaaagc aagatatgtc      540
aaaattcaaa tgacaattcc aagccaagat gagacaggga aatatgtgta tggtatcaaa      600
caggtgagaa tattcagtaa tactatgaga agtactgttg aggattgtag tagtgttaaa      660
caacataatg atggtagaga caaaatattc ccactcccat ataatggtga taattttgca      720
cccggattat tgttaaaggc tcacggaatt agtgtaaaga atagattaaa tgaattacaa      780
gagctttctg gtaaggtaac ttcaatatta ccaaatttgg atgcatgtag aaagacttct      840 gatggaaagag ataacacatt aaagatgcag gcaaccaaat taggattttt gtcagaaaaa      900
ttggagaaat taacttccga ctataatctc gagtataagt ttacgaagcc agctttagga      960
ggttccgagt tatatccagg ggaagattgt gttgctatta agaatgataa gactcaggaa      1020
gccattagtg gttttttatta tgttagacca ttctgttcaa ccaaaccatt gagagtttac     1080
tgtgatatga acactggaaa tacaatctat ccaatggaaa tgagtgttca ttcttccaga     1140
gcagcttctt cagcatgtgc aactgttgga ttaaaaccat tattgttaag ggacaaaaag     1200
gaatctgttg taggtattaa gaagatgttg aatatgatga atattaatga aatagaaga      1260 gttattcctt tgactcacga ctttggttgt gataatccta aaggatgcaa ttcacaattt     1320
acacagttag gcagtggtgt tgaagaattt gttgctgcat ctcctcaggc agcagcttca     1380
aactctacat ctggagcact tccagaactg gttctttgca gtacaaatac caatttgaag     1440
catgaaagca atgcaattc cttgtcttgt gaaagcagat tctctgatat gaaggtattt     1500
catttggat                                                             1509
```

<210> SEQ ID NO 65
<211> LENGTH: 2380
<212> TYPE: DNA
<213> ORGANISM: Cryptosporidium parvum

<400> SEQUENCE: 65

```
agtaagggtc aattatttaa cccagtaagt aagttgtgtg tacgacttaa agacaatgtt      60
gtaggtggag gagctctggt tttggatgat tgtcgtaaag ctagtgatgg aagtggatta      120
ttcgaattaa tgccaaacaa tcagctcaga ttagctagag gtggaaatct atgcttaaca      180
agtccaggag ataagccagg agtcgcgaat gttgcattaa actcagcagc cagttccaca      240
agtgtggtta gaacaggtat tgagaatggt ccagcaatgg ctgttgatgg aaaggataca      300
tcatattggt tgtcagattc ttcaactcct ggtaaagatt ctgcaaatgt taacttttg       360 agtgataccg gttcagttac aaaacttaaa gatatcttta ttgagtggaa atatcctgcc      420 attgactta atattgattt aagtgaaaat ggaaaggaat atcaaaccca gtttctgtg        480 aataataatg gattaatgtc aaccacttat tcattagaag gaaagaaagc aagatatgtc      540
aaaattcaaa tgacaattcc aagccaagat gagacaggga aatatgtgta tggtatcaaa      600
caggtgagaa tattcagtaa tactatgaga agtactgttg aggattgtag tagtgttaaa      660
caacataatg atggtagaga caaaatattc ccactcccat ataatggtga taattttgca      720
```

-continued

```
cccggattat tgttaaaggc tcacggaatt agtgtaaaga atagattaaa tgaattacaa    780
gagctttctg gtaaggtaac ttcaatatta ccaaatttgg atgcatgtag aaagacttct    840
gatggaagag ataacacatt aaagatgcag gcaaccaaat taggattttt gtcagaaaaa    900
ttggagaaat taacttccga ctataatctc gagtataagt ttacgaagcc agctttagga    960
ggttccgagt tatatccagg ggaagattgt gttgctatta agaatgataa gactcaggaa   1020
gccattagtg gttttattta tgttagacca ttctgttcaa ccaaaccatt gagagtttac   1080
tgtgatatga acactggaaa tacaatctat ccaatgaaaa tgagtgttca ttcttccaga   1140
gcagcttctt cagcatgtgc aactgttgga ttaaaaccat tattgttaag ggacaaaaag   1200
gaatctgttg taggtattaa gaagatgttg aatatgatga atattaatga taatagaaga   1260
gttattcctt tgactcacga ctttggttgt gataatccta aaggatgcaa ttcacaattt   1320
acacagttag gcagtggtgt tgaagaattt gttgctgcat ctcctcaggc agcagcttca   1380
aactctacat ctggagcact tccagaactg gttctttgca gtacaaatac caatttgaag   1440
catgaaagca atgcaatttc cttgtcttgt gaaagcagat tctctgatat gaaggtattt   1500
catttggatt agtaacctga attaaatgat gtagaagaga tctaatagct ttagtatgtt   1560
gcaaaaattc gttagaaagt tcaaggaact caagcttaaa cttctttgtt ttctttctcc   1620
atgattttt cttgttatac ttctctgcaa ccctaagtgt ttcttgccca aaattgatta   1680
attctctgat cttgggccta tatttggtga actcattaat aaatgtttca gtaacgacac   1740
tatttgggtt ttctgttaaa tctagtccaa agttaacagt tttgatcttc tttgccttat   1800
tataacaaac attaatctcc ttttcttgtt caggagatag ttcaacgtct tttgagtatg   1860
aaatacttgc ttctttatta taattcggat attcgctttg atcagtttgg ccttctgatc   1920
cgtcaatttg tgatctacgt tctataatag cttctggaat atctgtagca ggagcatctt   1980
gcggctttaa tccaacagga agctccttta ctgtattaat ataggagaac ggcatatttc   2040
caaagccatt agtatttaat tcgccattat tctgagtacc cttgggagaa ttatcgctaa   2100
tagaatcccc ttcagccttt tgaaggttga aattcagctg agtttcatcc atactacttg   2160
gatcagaatc ttcaaatcca gtagctagtc ttctagagaa agactcagca tcactatatc   2220
cttcattagt tgtttcctca gattctagaa tcttctccgt gatactttca gtaggatttg   2280
atgcgcgtaa atacagggct ttcctgcttg ttgaaatggc cagtttctgt aatttgagtt   2340
ttttcctcac tttcagactg ttctggataa tccggaattt                         2380
```

<210> SEQ ID NO 66  
<211> LENGTH: 503  
<212> TYPE: PRT  
<213> ORGANISM: Cryptosporidium parvum

<400> SEQUENCE: 66

```
Ser Lys Gly Gln Leu Phe Asn Pro Val Ser Lys Leu Cys Val Arg Leu
  1               5                  10                  15

Lys Asp Asn Val Val Gly Gly Ala Leu Val Leu Asp Asp Cys Arg
             20                  25                  30

Lys Ala Ser Asp Gly Ser Gly Leu Phe Glu Leu Met Pro Asn Asn Gln
         35                  40                  45

Leu Arg Leu Ala Arg Gly Gly Asn Leu Cys Leu Thr Ser Pro Gly Asp
     50                  55                  60

Lys Pro Gly Val Ala Asn Val Ala Leu Asn Ser Ala Ala Ser Ser Thr
 65                  70                  75                  80
```

```
Ser Val Val Arg Thr Gly Ile Glu Asn Gly Pro Ala Met Ala Val Asp
                 85                  90                  95

Gly Lys Asp Thr Ser Tyr Trp Leu Ser Asp Ser Ser Thr Pro Gly Lys
            100                 105                 110

Asp Ser Ala Asn Val Asn Phe Leu Ser Asp Thr Gly Ser Val Thr Lys
            115                 120                 125

Leu Lys Asp Ile Phe Ile Glu Trp Lys Tyr Pro Ala Ile Asp Phe Asn
            130                 135                 140

Ile Asp Leu Ser Glu Asn Gly Lys Glu Tyr Gln Thr Gln Val Ser Val
145                 150                 155                 160

Asn Asn Asn Gly Leu Met Ser Thr Thr Tyr Ser Leu Glu Gly Lys Lys
                165                 170                 175

Ala Arg Tyr Val Lys Ile Gln Met Thr Ile Pro Ser Gln Asp Glu Thr
            180                 185                 190

Gly Lys Tyr Val Tyr Gly Ile Lys Gln Val Arg Ile Phe Ser Asn Thr
            195                 200                 205

Met Arg Ser Thr Val Glu Asp Cys Ser Ser Val Lys Gln His Asn Asp
            210                 215                 220

Gly Arg Asp Lys Ile Phe Pro Leu Pro Tyr Asn Gly Asp Asn Phe Ala
225                 230                 235                 240

Pro Gly Leu Leu Leu Lys Ala His Gly Ile Ser Val Lys Asn Arg Leu
                245                 250                 255

Asn Glu Leu Gln Glu Leu Ser Gly Lys Val Thr Ser Ile Leu Pro Asn
            260                 265                 270

Leu Asp Ala Cys Arg Lys Thr Ser Asp Gly Arg Asp Asn Thr Leu Lys
            275                 280                 285

Met Gln Ala Thr Lys Leu Gly Phe Leu Ser Glu Lys Leu Glu Lys Leu
            290                 295                 300

Thr Ser Asp Tyr Asn Leu Glu Tyr Lys Phe Thr Lys Pro Ala Leu Gly
305                 310                 315                 320

Gly Ser Glu Leu Tyr Pro Gly Glu Asp Cys Val Ala Ile Lys Asn Asp
            325                 330                 335

Lys Thr Gln Glu Ala Ile Ser Gly Phe Tyr Tyr Val Arg Pro Phe Cys
            340                 345                 350

Ser Thr Lys Pro Leu Arg Val Tyr Cys Asp Met Asn Thr Gly Asn Thr
            355                 360                 365

Ile Tyr Pro Met Glu Met Ser Val His Ser Ser Arg Ala Ala Ser Ser
            370                 375                 380

Ala Cys Ala Thr Val Gly Leu Lys Pro Leu Leu Leu Arg Asp Lys Lys
385                 390                 395                 400

Glu Ser Val Val Gly Ile Lys Lys Met Leu Asn Met Met Asn Ile Asn
                405                 410                 415

Asp Asn Arg Arg Val Ile Pro Leu Thr His Asp Phe Gly Cys Asp Asn
            420                 425                 430

Pro Lys Gly Cys Asn Ser Gln Phe Thr Gln Leu Gly Ser Gly Val Glu
            435                 440                 445

Glu Phe Val Ala Ala Ser Pro Gln Ala Ala Ser Asn Ser Thr Ser
            450                 455                 460

Gly Ala Leu Pro Glu Leu Val Leu Cys Ser Thr Asn Thr Asn Leu Lys
465                 470                 475                 480

His Glu Ser Asn Ala Ile Ser Leu Ser Cys Glu Ser Arg Phe Ser Asp
                485                 490                 495
```

Met Lys Val Phe His Leu Asp
            500

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 67
taagggtcaa ttatttaacc c                                              21

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 68
taatccactt ccatcactag                                                20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 69
ctaattccgt gagcctttaa c                                              21

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 70
cctggacttg ttaagcatag at                                             22

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
taatccactt ccatcactag                                                20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 72
cccagtaagt aagttgtgtg                                                20

<210> SEQ ID NO 73
<211> LENGTH: 22
<212> TYPE: DNA

```
<213> ORGANISM: Artificial Sequence
<220> FEATURE:
<223> OTHER INFORMATION: Description of Artificial Sequence: Primer

<400> SEQUENCE: 73
cacattaaag atgcaggcaa cc                                              22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 74
cagcatgtgc aactgttgga                                                 20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 75
tcagcatgtg caactgttgg at                                              22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 76
tctagaagac tagctactgg                                                 20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 77
ttatgatgat gagataatta t                                               21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 78
agaagcaagt atttcatact c                                               21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 79
gaaagcagat tctctgatat                                                 20
```

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
attagatctc ttctacatca                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 81
cctaagtgtt tcttgcccaa                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 82
ccagttctgg aagtgctcca                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 83
cttgcttctt tattataatt                                               20

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 84
catcttctta atacctacaa ca                                            22

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 85
aatccccttc agccttttg                                                19

<210> SEQ ID NO 86
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 86
caatggtttg gttgaacaga                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 87
agtaggattt gatgcgcgta                                                    20

<210> SEQ ID NO 88
<211> LENGTH: 1663
<212> TYPE: DNA
<213> ORGANISM: Cryptosporidium parvum

<400> SEQUENCE: 88
caaaacttcc taatttctca atgtattact aattaataga aagtttgttt tattttcatg        60
tggataaatg aattattttc tctataccgg catttgcatg caattttgta tgactaaaat       120
gtaaataatt atttgcatgc aattatgtgg gcatgtcata gttttttcaag aataataata      180 agatgacatg acaagatatt caaaaaaatt tgatgattat atgttgaagt taattgaact       240
aaaaagtaat taagtaaaat ggacatagga acaacgtgg aagaacatca ggaatatatt        300
tctggaccat acattgcatt aattaatggc actaatcaac aaagggaacc gaataaaaag       360
ttgaaaaaca taataattgc aacgttgatt gcaatcttta tagttttggt tgttactgta       420
tctttgtata ttactaataa caccagtgac aaaattgacg atttcgtacc tggtgattat       480
gttgatccag caactaggga gtatagaaag agttttgagg agttcaaaaa gaaataccac       540
aaagtatata gctctatgga ggaggaaaat caaagatttg aaatttataa gcaaaatatg       600
aactttatta aaacaacaaa tagccaagga ttcagttatg tgttagaaat gaatgaattt       660
ggtgatttgt cgaaagaaga gtttatggca agattcacag gatatataaa agattccaaa       720
gatgatgaaa gggtatttaa gtcaagtaga gtctcagcaa gcgaatcaga agaggaattt       780
gttcccccaa attctattaa ttgggtggaa gctggatgcg tgaacccaat aagaaatcaa       840
aagaattgtg ggtcatgttg ggctttctct gctgttgcag ctttggaggg agcaacgtgt       900
gctcaaacaa accgaggatt accaagcttg agtgaacagc aatttgttga ttgcagtaaa       960
caaaatggca actttggatg tgatggagga acaatgggat tggcttttca gtatgcaatt      1020
aagaacaaat atttatgtac taatgatgat taccttact ttgctgagga aaaacatgt        1080 atggattcat tttgcgagaa ttatatagag attcctgtaa aagcctacaa atatgtattt      1140
ccgagaaata ttaatgcatt aaagactgct ttggctaagt atggaccaat ttcagttgca      1200
attcaggccg atcaaacccc tttccagttt tataaaagtg gagtattcga tgctccttgt      1260
ggaaccaagg ttaatcatgg agttgttcta gttgaatatg atatggatga agatactaat      1320
aaagaatatt ggctagtaag aaatagctgg ggtgaagcgt gggagagaa aggatacatc       1380 aaactagctc ttcattctgg aaagaaggga acatgtggta tattggttga gccagtgtat      1440
ccagtgatta atcaatcaat ataagcattt cagtgtttga ctaagtaatt ctaatatatt      1500
tcagcattct cagagataat tttagttcaa atgaacaatc tattcatata tataagcatt      1560
ccatacttaa ttatttattg attttaataa aatgtttggc taaagaaagc aatcaagata      1620

```
atttatggac gttctattgt tcttacttca ataataatcc ttt                      1663
```

<210> SEQ ID NO 89
<211> LENGTH: 534
<212> TYPE: DNA
<213> ORGANISM: Cryptosporidium parvum

<400> SEQUENCE: 89

```
ttaagtaaaa tggacatagg aaacaacgtg gaagaacatc aggatatatt ttctggacca     60
tacattgcat taattaatgg cactaatcaa caaagggaac cgaataaaaa gttgaaaaac    120
ataataattg caacgttgat tgcaatcttt atagttttgg ttgttactgt atctttgtat    180
attactaata acaccagtga caaaattgac gatttcgtac ctggtgatta tgttgatcca    240
gcaactaggg agtatagaaa gagttttgag gagttcaaaa agaaatacca caaagtatat    300
agctctatgg aggaggaaaa tcaaagattt gaaatttata agcaaaatat gaactttatt    360
aaaacaacaa atagccaagg attcagttat gtgttagaaa tgaatgaatt tggtgatttg    420
tcgaaagaag agtttatggc aagattcaca ggatatataa aagattccaa agatgatgaa    480
agggtattta agtcaagtag agtctcagca agcgaatcag aagaggaatt tgtt          534
```

<210> SEQ ID NO 90
<211> LENGTH: 678
<212> TYPE: DNA
<213> ORGANISM: Cryptosporidium parvum

<400> SEQUENCE: 90

```
cccccaaatt ctattaattg ggtggaagct ggatgcgtga acccaataag aaatcaaaag     60
aattgtgggt catgttgggc tttctctgct gttgcagctt tggagggagc aacgtgtgct    120
caaacaaacc gaggattacc aagcttgagt gaacagcaat tgttgattg cagtaaacaa     180
aatggcaact ttggatgtga tggaggaaca atgggattgg cttttcagta tgcaattaag    240
aacaaatatt tatgtactaa tgatgattac ccttactttg ctgaggaaaa acatgtatg     300
gattcatttt gcgagaatta tatagagatt cctgtaaaag cctacaaata tgtatttccg    360
agaaatatta atgcattaaa gactgctttg gctaagtatg gaccaatttc agttgcaatt    420
caggccgatc aaaccccttt ccagttttat aaaagtggag tattcgatgc tccttgtgga    480
accaaggtta atcatggagt tgttctagtt gaatatgata tggatgaaga tactaataaa    540
gaatattggc tagtaagaaa tagctggggt gaagcgtggg gagagaaagg atacatcaaa    600
ctagctcttc attctggaaa gaagggaaca tgtggtatat tggttgagcc agtgtatcca    660
gtgattaatc aatcaata                                                  678
```

<210> SEQ ID NO 91
<211> LENGTH: 401
<212> TYPE: PRT
<213> ORGANISM: Cryptosporidium parvum

<400> SEQUENCE: 91

```
Met Asp Ile Gly Asn Asn Val Glu Glu His Gln Glu Tyr Ile Ser Gly
 1               5                  10                  15

Pro Tyr Ile Ala Leu Ile Asn Gly Thr Asn Gln Gln Arg Glu Pro Asn
            20                  25                  30

Lys Lys Leu Lys Asn Ile Ile Ala Thr Leu Ile Ala Ile Phe Ile
        35                  40                  45

Val Leu Val Val Thr Val Ser Leu Tyr Ile Thr Asn Asn Thr Ser Asp
```

```
                50                      55                      60
Lys Ile Asp Asp Phe Val Pro Gly Asp Tyr Val Asp Pro Ala Thr Arg
 65                      70                      75                      80

Glu Tyr Arg Lys Ser Phe Glu Glu Phe Lys Lys Tyr His Lys Val
                         85                      90                      95

Tyr Ser Ser Met Glu Glu Glu Asn Gln Arg Phe Glu Ile Tyr Lys Gln
                        100                     105                     110

Asn Met Asn Phe Ile Lys Thr Thr Asn Ser Gln Gly Phe Ser Tyr Val
                        115                     120                     125

Leu Glu Met Asn Glu Phe Gly Asp Leu Ser Lys Glu Glu Phe Met Ala
                        130                     135                     140

Arg Phe Thr Gly Tyr Ile Lys Asp Ser Lys Asp Asp Glu Arg Val Phe
145                     150                     155                     160

Lys Ser Ser Arg Val Ser Ala Ser Glu Ser Glu Glu Phe Val Pro
                        165                     170                     175

Pro Asn Ser Ile Asn Trp Val Glu Ala Gly Cys Val Asn Pro Ile Arg
                        180                     185                     190

Asn Gln Lys Asn Cys Gly Ser Cys Trp Ala Phe Ser Ala Val Ala Ala
                        195                     200                     205

Leu Glu Gly Ala Thr Cys Ala Gln Thr Asn Arg Gly Leu Pro Ser Leu
                        210                     215                     220

Ser Glu Gln Gln Phe Val Asp Cys Ser Lys Gln Asn Gly Asn Phe Gly
225                     230                     235                     240

Cys Asp Gly Gly Thr Met Gly Leu Ala Phe Gln Tyr Ala Ile Lys Asn
                        245                     250                     255

Lys Tyr Leu Cys Thr Asn Asp Asp Tyr Pro Tyr Phe Ala Glu Glu Lys
                        260                     265                     270

Thr Cys Met Asp Ser Phe Cys Glu Asn Tyr Ile Glu Ile Pro Val Lys
                        275                     280                     285

Ala Tyr Lys Tyr Val Phe Pro Arg Asn Ile Asn Ala Leu Lys Thr Ala
                        290                     295                     300

Leu Ala Lys Tyr Gly Pro Ile Ser Val Ala Ile Gln Ala Asp Gln Thr
305                     310                     315                     320

Pro Phe Gln Phe Tyr Lys Ser Gly Val Phe Asp Ala Pro Cys Gly Thr
                        325                     330                     335

Lys Val Asn His Gly Val Val Leu Val Glu Tyr Asp Met Asp Glu Asp
                        340                     345                     350

Thr Asn Lys Glu Tyr Trp Leu Val Arg Asn Ser Trp Gly Glu Ala Trp
                        355                     360                     365

Gly Glu Lys Gly Tyr Ile Lys Leu Ala Leu His Ser Gly Lys Lys Gly
                        370                     375                     380

Thr Cys Gly Ile Leu Val Glu Pro Val Tyr Pro Val Ile Asn Gln Ser
385                     390                     395                     400

Ile

<210> SEQ ID NO 92
<211> LENGTH: 175
<212> TYPE: PRT
<213> ORGANISM: Cryptosporidium parvum

<400> SEQUENCE: 92

Met Asp Ile Gly Asn Asn Val Glu Glu His Gln Glu Tyr Ile Ser Gly
 1               5                      10                      15

Pro Tyr Ile Ala Leu Ile Asn Gly Thr Asn Gln Gln Arg Glu Pro Asn
```

```
                      20                  25                  30
Lys Lys Leu Lys Asn Ile Ile Ala Thr Leu Ile Ala Ile Phe Ile
                35                  40                  45

Val Leu Val Val Thr Val Ser Leu Tyr Ile Thr Asn Asn Thr Ser Asp
 50                  55                  60

Lys Ile Asp Asp Phe Val Pro Gly Asp Tyr Val Asp Pro Ala Thr Arg
 65                  70                  75                  80

Glu Tyr Arg Lys Ser Phe Glu Phe Lys Lys Tyr His Lys Val
                85                  90                  95

Tyr Ser Ser Met Glu Glu Asn Gln Arg Phe Glu Ile Tyr Lys Gln
               100                 105                 110

Asn Met Asn Phe Ile Lys Thr Thr Asn Ser Gln Gly Phe Ser Tyr Val
               115                 120                 125

Leu Glu Met Asn Glu Phe Gly Asp Leu Ser Lys Glu Glu Phe Met Ala
 130                 135                 140

Arg Phe Thr Gly Tyr Ile Lys Asp Ser Lys Asp Asp Glu Arg Val Phe
 145                 150                 155                 160

Lys Ser Ser Arg Val Ser Ala Ser Glu Ser Glu Glu Phe Val
               165                 170                 175

<210> SEQ ID NO 93
<211> LENGTH: 226
<212> TYPE: PRT
<213> ORGANISM: Cryptosporidium parvum

<400> SEQUENCE: 93

Pro Pro Asn Ser Ile Asn Trp Val Glu Ala Gly Cys Val Asn Pro Ile
 1                   5                  10                  15

Arg Asn Gln Lys Asn Cys Gly Ser Cys Trp Ala Phe Ser Ala Val Ala
                20                  25                  30

Ala Leu Glu Gly Ala Thr Cys Ala Gln Thr Asn Arg Gly Leu Pro Ser
            35                  40                  45

Leu Ser Glu Gln Gln Phe Val Asp Cys Ser Lys Gln Asn Gly Asn Phe
 50                  55                  60

Gly Cys Asp Gly Gly Thr Met Gly Leu Ala Phe Gln Tyr Ala Ile Lys
 65                  70                  75                  80

Asn Lys Tyr Leu Cys Thr Asn Asp Asp Tyr Pro Tyr Phe Ala Glu Glu
                85                  90                  95

Lys Thr Cys Met Asp Ser Phe Cys Glu Asn Tyr Ile Glu Ile Pro Val
               100                 105                 110

Lys Ala Tyr Lys Tyr Val Phe Pro Arg Asn Ile Asn Ala Leu Lys Thr
               115                 120                 125

Ala Leu Ala Lys Tyr Gly Pro Ile Ser Val Ala Ile Gln Ala Asp Gln
 130                 135                 140

Thr Pro Phe Gln Phe Tyr Lys Ser Gly Val Phe Asp Ala Pro Cys Gly
 145                 150                 155                 160

Thr Lys Val Asn His Gly Val Val Leu Val Glu Tyr Asp Met Asp Glu
               165                 170                 175

Asp Thr Asn Lys Glu Tyr Trp Leu Val Arg Asn Ser Trp Gly Glu Ala
               180                 185                 190

Trp Gly Glu Lys Gly Tyr Ile Lys Leu Ala Leu His Ser Gly Lys Lys
               195                 200                 205

Gly Thr Cys Gly Ile Leu Val Glu Pro Val Tyr Pro Val Ile Asn Gln
 210                 215                 220
```

Ser Ile
225

<210> SEQ ID NO 94
<211> LENGTH: 457
<212> TYPE: DNA
<213> ORGANISM: Cryptosporidium parvum

<400> SEQUENCE: 94

| | | | | | |
|---|---|---|---|---|---|
| tgctgttgca | gctttggagg | g

<213> ORGANISM: Artificial Sequence
<220> FEATURE:
<223> OTHER INFORMATION: Description of Artificial Sequence: Primer

<400> SEQUENCE: 99
gagactctac ttgacttaaa tacc                                    24

<210> SEQ ID NO 100
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 100
acaaaccgag gattacc                                            17

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 101
aacaaattgc tgttcactca agc                                     23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 102
actcgtttgg ctaagtatgg acc                                     23

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 103
atgctccttg tggaaccaag                                         20

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 104
gctagtttga tgtatcc                                            17

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 105
gattgattaa tcactggata c                                       21

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 106
ggtatattgg ttgagcc                                                17

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (15)
<223> OTHER INFORMATION: i
<221> NAME/KEY: modified_base
<222> LOCATION: (18)
<223> OTHER INFORMATION: i
<221> NAME/KEY: modified_base
<222> LOCATION: (27)
<223> OTHER INFORMATION: i

<400> SEQUENCE: 107
aaaggatcct gyggnwsntg ytgggcntt                                   29

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (13)
<223> OTHER INFORMATION: i
<221> NAME/KEY: modified_base
<222> LOCATION: (19)
<223> OTHER INFORMATION: i
<221> NAME/KEY: modified_base
<222> LOCATION: (22)
<223> OTHER INFORMATION: i

<400> SEQUENCE: 108
tttgaattcc canswrttny knaynatcca rta                              33

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 109
ccaggtacca tggacatagg aaac                                        24

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 110
cctctagatg cttatattga ttg                                         23

<210> SEQ ID NO 111
<211> LENGTH: 7
<212> TYPE: PRT
<213> ORGANISM: Cryptosporidium parvum

<400> SEQUENCE: 111

Cys Gly Ser Cys Trp Ala Phe
 1               5

<210> SEQ ID NO 112
<211> LENGTH: 8
<212> TYPE: PRT
<213> ORGANISM: Cryptosporidium parvum
<220> FEATURE:
<221> NAME/KEY: MOD_RES
<222> LOCATION: (3)
<223> OTHER INFORMATION: L or I

<400> SEQUENCE: 112

Tyr Trp Xaa Val Arg Asn Ser Trp
 1               5

<210> SEQ ID NO 113
<211> LENGTH: 5
<212> TYPE: PRT
<213> ORGANISM: Cryptosporidium parvum

<400> SEQUENCE: 113

Val Arg Asn Ser Trp
 1               5

<210> SEQ ID NO 114
<211> LENGTH: 1203
<212> TYPE: DNA
<213> ORGANISM: Cryptosporidium parvum

<400> SEQUENCE: 114

| | | | | | |
|---|---|---|---|---|---|
| atggacatag | gaaacaacgt | ggaagaacat | caggaatata | tttctggacc | atacattgca | 60 |
| ttaattaatg | gcactaatca | acaaagggaa | ccgaataaaa | agttgaaaaa | cataataatt | 120 |
| gcaacgttga | ttgcaatctt | tatagttttg | gttgttactg | tatctttgta | tattactaat | 180 |
| aacaccagtg | acaaaattga | cgatttcgta | cctggtgatt | atgttgatcc | agcaactagg | 240 |
| gagtatagaa | agagttttga | ggagttcaaa | agaaatacc | acaaagtata | tagctctatg | 300 |
| gaggaggaaa | atcaaagatt | tgaaatttat | aagcaaaata | tgaactttat | taaacaaca | 360 |
| aatagccaag | gattcagtta | tgtgttagaa | atgaatgaat | ttggtgattt | gtcgaaagaa | 420 |
| gagtttatgg | caagattcac | aggatatata | aaagattcca | aagatgatga | aagggtattt | 480 |
| aagtcaagta | gagtctcagc | aagcgaatca | gaagaggaat | ttgttccccc | aaattctatt | 540 |
| aattgggtgg | aagctggatg | cgtgaaccca | ataagaaatc | aaaagaattg | tgggtcatgt | 600 |
| tgggctttct | ctgctgttgc | agctttggag | ggagcaacgt | gtgctcaaac | aaaccgagga | 660 |
| ttaccaagct | tgagtgaaca | gcaatttgtt | gattgcagta | aacaaatgg | caactttgga | 720 |
| tgtgatggag | gaacaatggg | attggctttt | cagtatgcaa | ttaagaacaa | atatttatgt | 780 |
| actaatgatg | attacccta | ctttgctgag | gaaaaaacat | gtatggattc | attttgcgag | 840 |
| aattatatag | agattcctgt | aaaagcctac | aaatatgtat | tccgagaaa | tattaatgca | 900 |
| ttaaagactg | ctttggctaa | gtatggacca | atttcagttg | caattcaggc | cgatcaaaacc | 960 |
| cctttccagt | tttataaaag | tggagtattc | gatgctcctt | gtggaaccaa | ggttaatcat | 1020 |

```
ggagttgttc tagttgaata tgatatggat gaagatacta ataaagaata ttggctagta    1080
agaaatagct ggggtgaagc gtggggagag aaaggataca tcaaactagc tcttcattct    1140
ggaaagaagg gaacatgtgg tatattggtt gagccagtgt atccagtgat taatcaatca    1200
ata                                                                  1203
```

<210> SEQ ID NO 115
<211> LENGTH: 540
<212> TYPE: PRT
<213> ORGANISM: Cryptosporidium parvum

<400> SEQUENCE: 115

```
Gln Asn Phe Leu Ile Ser Gln Cys Ile Thr Asn Lys Val Cys Phe Ile
  1               5                  10                  15

Phe Met Trp Ile Asn Glu Leu Phe Ser Leu Tyr Arg His Leu His Ala
             20                  25                  30

Ile Leu Tyr Asp Asn Val Asn Asn Tyr Leu His Ala Ile Met Trp Ala
         35                  40                  45

Cys His Ser Phe Ser Arg Ile Ile Ile Arg His Asp Lys Ile Phe Lys
     50                  55                  60

Lys Ile Leu Tyr Val Glu Val Asn Thr Lys Lys Leu Ser Lys Met Asp
 65                  70                  75                  80

Ile Gly Asn Asn Val Glu Glu His Gln Glu Tyr Ile Ser Gly Pro Tyr
                 85                  90                  95

Ile Ala Leu Ile Asn Gly Thr Asn Gln Gln Arg Glu Pro Asn Lys Lys
            100                 105                 110

Leu Lys Asn Ile Ile Ile Ala Thr Leu Ile Ala Ile Phe Ile Val Leu
        115                 120                 125

Val Val Thr Val Ser Leu Tyr Ile Thr Asn Asn Thr Ser Asp Lys Ile
130                 135                 140

Asp Asp Phe Val Pro Gly Asp Tyr Val Asp Pro Ala Thr Arg Glu Tyr
145                 150                 155                 160

Arg Lys Ser Phe Glu Glu Phe Lys Lys Lys Tyr His Lys Val Tyr Ser
                165                 170                 175

Ser Met Glu Glu Glu Asn Gln Arg Phe Glu Ile Tyr Lys Gln Asn Met
            180                 185                 190

Asn Phe Ile Lys Thr Thr Asn Ser Gln Gly Phe Ser Tyr Val Leu Glu
        195                 200                 205

Met Asn Glu Phe Gly Asp Leu Ser Lys Glu Glu Phe Met Ala Arg Phe
    210                 215                 220

Thr Gly Tyr Ile Lys Asp Ser Lys Asp Asp Glu Arg Val Phe Lys Ser
225                 230                 235                 240

Ser Arg Val Ser Ala Ser Glu Ser Glu Glu Phe Val Pro Pro Asn
                245                 250                 255

Ser Ile Asn Trp Val Glu Ala Gly Cys Val Asn Pro Ile Arg Asn Gln
            260                 265                 270

Lys Asn Cys Gly Ser Cys Trp Ala Phe Ser Ala Val Ala Ala Leu Glu
        275                 280                 285

Gly Ala Thr Cys Ala Gln Thr Asn Arg Gly Leu Pro Ser Leu Ser Glu
    290                 295                 300

Gln Gln Phe Val Asp Cys Ser Lys Gln Asn Gly Asn Phe Gly Cys Asp
305                 310                 315                 320

Gly Gly Thr Met Gly Leu Ala Phe Gln Tyr Ala Ile Lys Asn Lys Tyr
                325                 330                 335
```

-continued

```
Leu Cys Thr Asn Asp Asp Tyr Pro Tyr Phe Ala Glu Glu Lys Thr Cys
            340             345             350

Met Asp Ser Phe Cys Glu Asn Tyr Ile Glu Ile Pro Val Lys Ala Tyr
            355             360             365

Lys Tyr Val Phe Pro Arg Asn Ile Asn Ala Leu Lys Thr Ala Leu Ala
    370             375             380

Lys Tyr Gly Pro Ile Ser Val Ala Ile Gln Ala Asp Gln Thr Pro Phe
385             390             395             400

Gln Phe Tyr Lys Ser Gly Val Phe Asp Ala Pro Cys Gly Thr Lys Val
            405             410             415

Asn His Gly Val Val Leu Val Glu Tyr Asp Met Asp Glu Asp Thr Asn
            420             425             430

Lys Glu Tyr Trp Leu Val Arg Asn Ser Trp Gly Glu Ala Trp Gly Glu
        435             440             445

Lys Gly Tyr Ile Lys Leu Ala Leu His Ser Gly Lys Lys Gly Thr Cys
    450             455             460

Gly Ile Leu Val Glu Pro Val Tyr Pro Val Ile Asn Gln Ser Ile Ala
465             470             475             480

Phe Gln Cys Leu Thr Lys Phe Tyr Ile Ser Ala Phe Ser Glu Ile Ile
            485             490             495

Leu Val Gln Met Asn Asn Leu Phe Ile Tyr Ile Ser Ile Pro Tyr Leu
            500             505             510

Ile Ile Tyr Phe Asn Val Trp Leu Lys Lys Ala Ile Lys Ile Ile Tyr
        515             520             525

Gly Arg Ser Ile Val Leu Thr Ser Ile Ile Ile Leu
530             535             540
```